(12) United States Patent
Viti et al.

(10) Patent No.: US 12,012,418 B2
(45) Date of Patent: Jun. 18, 2024

(54) ARYL RECEPTOR MODULATORS AND METHODS OF MAKING AND USING THE SAME

(71) Applicant: Nogra Pharma Limited, Dublin (IE)

(72) Inventors: Francesca Viti, Salorino (CH); Salvatore Bellinvia, Mendrisio (CH); Salvatore Demartis, Milan (IT)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 17/859,505

(22) Filed: Jul. 7, 2022

(65) Prior Publication Data

US 2023/0234963 A1 Jul. 27, 2023

Related U.S. Application Data

(63) Continuation of application No. 15/321,967, filed as application No. PCT/EP2015/064613 on Jun. 26, 2015, now Pat. No. 11,427,600.

(60) Provisional application No. 62/056,054, filed on Sep. 26, 2014, provisional application No. 62/017,959, filed on Jun. 27, 2014.

(51) Int. Cl.
| | | |
|---|---|---|
| C07D 495/14 | (2006.01) | |
| C07C 233/29 | (2006.01) | |
| C07C 233/73 | (2006.01) | |
| C07C 235/38 | (2006.01) | |
| C07C 235/46 | (2006.01) | |
| C07D 209/08 | (2006.01) | |
| C07D 209/14 | (2006.01) | |
| C07D 209/86 | (2006.01) | |
| C07D 209/94 | (2006.01) | |
| C07D 213/75 | (2006.01) | |
| C07D 235/30 | (2006.01) | |
| C07D 277/64 | (2006.01) | |
| C07D 277/82 | (2006.01) | |
| C07D 333/36 | (2006.01) | |
| C07D 471/04 | (2006.01) | |
| C07D 487/04 | (2006.01) | |
| C07D 495/04 | (2006.01) | |

(52) U.S. Cl.
CPC .......... *C07D 495/14* (2013.01); *C07C 233/29* (2013.01); *C07C 233/73* (2013.01); *C07C 235/38* (2013.01); *C07C 235/46* (2013.01); *C07D 209/08* (2013.01); *C07D 209/14* (2013.01); *C07D 209/86* (2013.01); *C07D 209/94* (2013.01); *C07D 213/75* (2013.01); *C07D 235/30* (2013.01); *C07D 277/64* (2013.01); *C07D 277/82* (2013.01); *C07D 333/36* (2013.01); *C07D 471/04* (2013.01); *C07D 487/04* (2013.01); *C07D 495/04* (2013.01)

(58) Field of Classification Search
CPC ..................................................... C07D 495/14
USPC ......................................................... 514/406
See application file for complete search history.

(56) References Cited

U.S. PATENT DOCUMENTS

| | | |
|---|---|---|
| 3,345,376 A | 10/1967 | Hester et al. |
| 6,069,150 A | 5/2000 | Spinelli et al. |
| 6,436,925 B1 | 8/2002 | Lubisch et al. |
| 6,720,331 B2 | 4/2004 | Yeh et al. |
| 7,138,529 B2 | 11/2006 | Erickson et al. |
| 7,375,131 B2 | 5/2008 | Callahan et al. |
| 7,524,878 B2 | 4/2009 | Whitehouse et al. |
| 7,767,689 B2 | 8/2010 | Moon et al. |
| 7,884,124 B2 | 2/2011 | Heffernan et al. |
| 7,981,925 B2 | 7/2011 | Velicelebi et al. |
| 8,058,271 B2 | 11/2011 | Green et al. |
| 8,278,306 B2 | 10/2012 | Green et al. |
| 8,372,860 B2 | 2/2013 | Moon et al. |
| 8,372,991 B2 | 2/2013 | Velicelebi et al. |
| 8,440,711 B2 | 5/2013 | Allegretti et al. |
| 9,216,180 B2 | 12/2015 | Gardner et al. |
| 9,980,947 B2 | 5/2018 | Labadie et al. |
| 2002/0151534 A1 | 10/2002 | Ries et al. |
| 2003/0040527 A1 | 2/2003 | Yeh et al. |
| 2003/0195240 A1 | 10/2003 | Kalindjian et al. |
| 2005/0282849 A1 | 12/2005 | Moon et al. |
| 2007/0249670 A1 | 10/2007 | Evans et al. |
| 2007/0254878 A1 | 11/2007 | Cao et al. |
| 2008/0103164 A1 | 5/2008 | Gudmundsson et al. |
| 2008/0200468 A1 | 8/2008 | Simpson et al. |
| 2008/0207741 A1 | 8/2008 | Aydt et al. |
| 2008/0249180 A1 | 10/2008 | Gobbi et al. |

(Continued)

FOREIGN PATENT DOCUMENTS

| | | |
|---|---|---|
| CN | 103864779 A | 6/2014 |
| CN | 107880040 A | 4/2018 |

(Continued)

OTHER PUBLICATIONS

Kawashima et al., Chem Pharm Bull (1995) 43(5), pp. 783-787. Filed by applicant in U.S. Appl. No. 15/321,967.*

(Continued)

*Primary Examiner* — Taofiq A Solola
(74) *Attorney, Agent, or Firm* — Goodwin Procter LLP

(57) ABSTRACT

The present invention is generally directed towards compounds capable of binding the aryl hydrocarbon receptor and modulating its activity, methods of treating inflammatory conditions such as Crohn's disease using such compounds, and pharmaceutical compositions comprising such compounds. Also provided are methods of increasing levels of IL-22 in a subject and/or decreasing levels of IFN-γ in a subject.

3 Claims, 37 Drawing Sheets
Specification includes a Sequence Listing.

(56) References Cited

U.S. PATENT DOCUMENTS

| | | | |
|---|---|---|---|
| 2009/0053192 | A1 | 2/2009 | Millan et al. |
| 2009/0163545 | A1 | 6/2009 | Goldfarb |
| 2013/0171103 | A1 | 7/2013 | Davis et al. |
| 2015/0005275 | A1 | 1/2015 | Plas et al. |
| 2015/0119426 | A1 | 4/2015 | Marugan et al. |
| 2015/0299218 | A1 | 10/2015 | Ambroise et al. |
| 2016/0030389 | A1 | 2/2016 | Duncan et al. |
| 2018/0021273 | A1 | 1/2018 | O'Connor et al. |
| 2018/0193309 | A1 | 7/2018 | Duncan et al. |

FOREIGN PATENT DOCUMENTS

| | | |
|---|---|---|
| JP | H03287586 | 12/1991 |
| KR | 101453413 B1 | 11/2014 |
| WO | WO-1998/045268 A1 | 10/1998 |
| WO | WO-2001/025190 A1 | 4/2001 |
| WO | WO-2001/087882 A2 | 11/2001 |
| WO | WO-2001/098290 A2 | 12/2001 |
| WO | WO-2002/062778 A2 | 8/2002 |
| WO | WO-2005/089764 A1 | 9/2005 |
| WO | WO-2006/058088 A2 | 6/2006 |
| WO | WO-2007/087129 A2 | 8/2007 |
| WO | WO-2007/100657 A2 | 9/2007 |
| WO | WO-2007/118137 A1 | 10/2007 |
| WO | WO-2007/087130 A3 | 12/2007 |
| WO | WO-2007/087429 A3 | 6/2008 |
| WO | WO-2008/110488 A1 | 9/2008 |
| WO | WO-2008/111299 A1 | 9/2008 |
| WO | WO-2008/111300 A1 | 9/2008 |
| WO | WO-2008/127714 A1 | 10/2008 |
| WO | WO-2009/073620 A2 | 6/2009 |
| WO | WO-2010/138758 A1 | 12/2010 |
| WO | WO-2010/148350 A1 | 12/2010 |
| WO | WO-2011/150162 A1 | 12/2011 |
| WO | WO-2012/088420 A1 | 6/2012 |
| WO | WO-2014/008214 A1 | 1/2014 |
| WO | WO-2015/162216 A1 | 10/2015 |
| WO | WO-2015/197861 A1 | 12/2015 |
| WO | WO-2017/073743 A1 | 5/2017 |
| WO | WO-2018/110669 A1 | 6/2018 |

OTHER PUBLICATIONS

"Palladium-Catalyzed Intramolecular Cyclization of Nitroalkenes: Synthesis of Thienopyrroles" European Journal of Organic Chemistry (2017), 2017(14), 1902-1910.

Abou-Gharbia et al., (1987) "Antipsychotic Activity of Substituted γ-Carbolines" *J. Med. Chem.* 30(10):1818-23.

Alam et al., (2010), 'Notch Signaling Drives IL-22 Secretion in CD4+ T Cells by Stimulating the Aryl Hydrocarbon Receptor,' Proc Natl Acad Sci USA, 107(13):5943-8.

Audia et al., "Potent, Selective Tetrahydro-β-carboline Antagonists of the Serotonin 2B (5HT2B) Contractile Receptor in the Rat Stomach Fundus" Journal of Medicinal Chemistry (1996), 39(14), 2773-2780.

CAS Registry No. 1002531-50-1; STN entry date: Feb. 10, 2008; chemical name: 2-Thiophenecarboxylic acid, 3-methyl-5-[[2-(3,4,5-trimethoxyphenyl)acetyl]amino]-, ethyl ester.

CAS Registry No. 1061690-71-8; STN entry date: Oct. 15, 2008; chemical name: 3-Thiophenecarboxylic acid, 5-ethyl-2-[[2-(3,4,5-trimethoxyphenyl]acetyllamino]-, ethyl ester.

CAS Registry No. 1286986-56-8; STN entry date: Apr. 28, 2011; chemical name: 3-Thiophenecarboxylic acid, 4-cyclopropyl-2-[[2-(3,4,5-trimethoxyphenyl)acetyl]amino]-, ethyl ester.

CAS Registry No. 1287113-22-7; STN entry date: Apr. 28, 2011; chemical name: Benzeneacetamide, N-(3-cyano-2-thienyl)-3,4,5-trimethoxy-.

CAS Registry No. 1828225-26-8; STN entry date: Dec. 13, 2015; chemical name: 3-Thiophenecarboxylic acid, 5-[[2-(3,4,5-trimethoxyphenyl)acetyl]amino]-.

CAS Registry No. 528525-03-3; STN entry date: Jun. 10, 2003; chemical name: 1H-Pyrido[3,4-b]indole, 2,3,4,9-tetrahydro-1-[3-methoxy-4-(phenylmethoxy)phenyl]-6-methyl-.

CAS Registry No. 529476-20-8; STN entry date: Jun. 12, 2003; chemical name: 1H-Pyrido[3,4-b]indole, 1-(3,4-dimethoxyphenyl)-2,3,4,9-tetrahydro-6-methyl-.

CAS Registry No. 529476-21-9; STN entry date: Jun. 12, 2003; chemical name: 1H-Pyrido[3,4-b]indole, 1-(3,4-dimethoxyphenyl)-6-ethoxy-2,3,4,9-tetrahydro-.

CAS Registry No. 529476-23-1; STN entry date: Jun. 12, 2003; chemical name: 1H-Pyrido[3,4-b]indole, 6-bromo-1-(3,4-dimethoxyphenyl)-2,3,4,9-tetrahydro-.

CAS Registry No. 529476-24-2; STN entry date: Jun. 12, 2003; chemical name: 1H-Pyrido[3,4-b]indole, 1-(3,4-dimethoxyphenyl)-6-fluoro-2,3,4,9-tetrahydro-.

CAS Registry No. 532924-61-1; STN entry date: Jun. 18, 2003; chemical name: 1H-Pyrido[3,4-b]indole, 2,3,4,9-tetrahydro-1-[3-methoxy-4-(2-methylpropoxy)phenyl]-6-methyl-.

CAS Registry No. 532924-81-5; STN entry date: Jun. 18, 2003; chemical name: 1H-Pyrido[3,4-b]indole, 2,3,4,9-tetrahydro-1-[3-methoxy-4-(3-methylbutoxy)phenyl]-6-methyl-.

CAS Registry No. 532924-91-7; STN entry date: Jun. 18, 2003; chemical name: 1H-Pyrido[3,4-b]indole, 2,3,4,9-tetrahydro-1-[3-methoxy-4-(2-phenylethoxy)phenyl]-6-methyl-.

CAS Registry No. 533864-22-1; STN entry date: Jun. 19, 2003; chemical name: Phenol, 2-methoxy-4-(2,3,4,9-tetrahydro-6-methyl-1H-pyrido[3,4-b]indol-1-yl)-.

Chauhan et al. "Iodine-Catalyzed Metal-Free Oxidative Ring Opening of 1-Aryltetrahydro-?-carbolines: Facile Synthesisof C-2 Aroyl and Aryl Methanimino Indole Derivatives" European Journal of Organic Chemistry (2018), 2018(34), 4776-4786.

CHEMCATS file: CAS Registry No. 1003752-91-7; STN entry date: Feb. 15, 2008; chemical name: Benzeneacetamide, 3,4,5-trimethoxy-N-[4-(trifluoromethyl)phenyl]-.

CHEMCATS file: CAS Registry No. 1030235-12-1; STN entry date: Jun. 24, 2008; chemical name: 3-Thiophenecarboxylic acid, 4-ethyl-5-methyl-2-[[2-(3,4,5-trimethoxyphenyl)acetyl]amino]-, ethyl ester.

CHEMCATS file: CAS Registry No. 1059182-77-2; STN entry date: Oct. 10, 2008; chemical name: Benzeneacetamide, N-(3,4-dimethoxyphenyl)-4-(trifluoromethyl)-.

CHEMCATS file: CAS Registry No. 1180442-67-4; STN entry date: Sep. 4, 2009; chemical name: Benzeneacetamide, 3,4,5-trimethoxy-N-phenyl-.

CHEMCATS file: CAS Registry No. 1323740-17-5; STN entry date: Aug. 26, 2011; chemical name: Benzeneacetamide, 3,4,5-trimethoxy-N-4-pyridinyl-.

CHEMCATS file: CAS Registry No. 639790-82-2; STN entry date: Jan. 21, 2004; chemical name: Benzeneacetamide, 3,4-dimethoxy-N-[4-(trifluoromethyl)phenyl]-.

CHEMCATS file; CAS Registry No. 1043293-02-2; STN entry date: Aug. 24, 2008; chemical name: 2-Thiophenecarboxylic acid, 5-[[2-(3,4,5-trimethoxyphenyl)acetyl]amino]-, methyl ester.

CHEMCATS file; CAS Registry No. 2094381-45-8; STN entry date: May 2, 2017; chemical name: 3-Thiophenecarboxylic acid, 5-(trifluoromethyl)-2-[[2-(3,4,5-trimethoxyphenyl)acetyl]amino]- ethyl ester.

CHEMCATS file; CAS Registry No. 2104951-19-9; STN entry date: Jul. 30, 2017; chemical name: Ethanone, 1-[5-(phenylmethyl)-4H-thieno[3,2-b]pyrrol-2-yl]-.

CHEMCATS file; CAS Registry No. 2105082-48-0; STN entry date: Jul. 30, 2017; chemical name: 4H-Thieno[3,2-b]pyrrole-2-carboxylic acid, 5-(phenylmethyl)-.

CHEMCATS file; CAS Registry No. 2106222-37-9; STN entry date: Aug. 1, 2017; chemical name: 4H-Thieno[3,2-b]pyrrole-2-carboxylic acid, 5-(phenylmethyl)-, methyl ester.

CHEMCATS file; CAS Registry No. 2106711-61-7; STN entry date: Aug. 1, 2017; chemical name: 4H-Thieno[3,2-b]pyrrole-2-carboxaldehyde, 5-[(3-fluorophenyl)methyl]-.

CHEMCATS file; CAS Registry No. 2107477-24-5; STN entry date: Aug. 3, 2017; chemical name: 4H-Thieno[3,2-b]pyrrole-2-carbonitrile, 5-(phenylmethyl)-.

(56) References Cited

OTHER PUBLICATIONS

CHEMCATS file; CAS Registry No. 2110143-04-7; STN entry date: Aug. 8, 2017; chemical name: 4H-Thieno[3,2-b]pyrrole-2-carboxylic acid, 5-(phenylmethyl)-, ethyl ester.
CHEMCATS file; CAS Registry No. 2111665-32-6; STN entry date: Aug. 10, 2017; chemical name: 4H-Thieno[3,2-b]pyrrole-2-carboxaldehyde, 5-(phenylmethyl)-.
CHEMCATS file; CAS Registry No. 529476-26-4; STN entry date: Jun. 12, 2003; chemical name: 1H-Pyrido[3,4-b]indole, 1-(3,4-dimethoxyphenyl)-2,3,4,9-tetrahydro-6-(phenylmethoxy)-.
De, Surya K., et al. "Design, synthesis, and structure-activity relationship studies of thiophene-3-carboxamide derivatives as dual inhibitors of the c-Jun N-terminal kinase." Bioorganic & medicinal chemistry 19.8 (2011): 2582-2588.
DeGraw JI et al., (1967), 'Substituted 1,2,3,4-tetrahydro-ß-Carbolines. II.,' J Med Chem, 10(1):127-8.
Denison and Nagy, (2003), 'Activation of the Aryl Hydrocarbon Receptor by Structurally Diverse Exogenous and Endogenous Chemicals,' Annu Rev Pharmacol Toxicol, 43:309-34.
Desroses et al., (2013) "A facile and efficient synthesis of tetrahydro-β-carbolines," Tetrahedron Letters 54:3554-7.
Dong et al., "Study on the Pictet-Spengler Reaction of Tryptamine Hydrohalide with Aldehyde" Chinese Journ. of Synthetic Chemistry, Hecheng Huaxue (2009), 17(5), 544-547.
Fodor et al., "Comparative evaluation of a Pictet-Spengler protocol in microwave-assisted conversions of tryptamine with aryl- and carboxyaryl aldehydes: role of ring strain in cyclocondensation of the primarily formed carboxyaryl-substituted ß-carbolines" Monatshefte fuer Chemie (2013), 144(9), 1381-1387.
Gellis et al., "Preparation and antiprotozoal evaluation of promising ß-carboline alkaloids" Biomedicine & Pharmacotherapy (2012), 66(5), 339-347.
Gu et al., (2000) 'The PAS Superfamily: Sensors of Environmental and Developmental Signals,' Annu Rev Pharmacol Toxicol, 40:519-61.
Hadjaz F et al., (2008), 'A Mild and Efficient Route to 2-Benzyl Tryptamine Derivatives via Ring- Opening of β-Carbolines,' Tetrahedron, 64(42):10004-8.
Hadjaz F et al., (2011), 'Antioxydant Activity of β-Carboline Derivatives in the LDL Oxidation Model,' Eur J Med Chem, 46(6):2575-85.
International Search Report for International Application No. PCT/EP2015/064613, mailed Nov. 25, 2015 (8 pages).
Ivanov et al., "A simple method for the synthesis of 1-substituted ß-carboline derivatives from tryptamine and carboxylic acids in polyphosphoric acid" Heterocycles (2005), 65(10), 2483-2492.
Jiang et al., "Furoyl and Benzofuroyl Pyrroloquinolones as Potent and Selective PDE5 Inhibitors for Treatment of Erectile Dysfunction" Journal of Medicinal Chemistry (2003), 46(3), 441-444.
Kawashima et al., "Synthesis and Pharmacological Evaluation of 1,2,3,4-Tetrahydro-β-carboline Derivatives" Chemical & Pharmaceutical Bulletin (1995), 43(5),783-7.
King, (1994) "Bioisosteres, Conformational Restriction, and Prodrugs—Case History: An Example of a Conformational Restriction Approach," Med. Chem., Principle and Practice 206-208.
Kranich, et al., (2007) "Rational Design of Novel, Potent Small Molecule Pan-Selectiv Antagonists," J. Med. Chem, 50(6):1101-15.
Lindh et al. "Toward a Benchmarking Data Set Able to Evaluate Ligand—and Structure-based Virtual Screening Using Public HTS Data", Journal of Chemical Information and Modeling, (2015), 55(2), 343-353.
Lipka et al., (2012) "Analytical and Preparative Chiral Separation of ß-Carboline Derivatives, LDL Oxidation Inhibitors, Using HPLC and CE Methodologies: Determination of Enantiomeric Purity," Chromatographia 75:337-45.
Marafini, I. et al., "NPD-0414-2 and NPD-0414-24, Two Chemical Entities Designed as Aryl Hydrocarbon Receptor (AhR) Ligands, Inhibit Gut Inflammatory Signals." Front. Pharmacol. 2019, 10, 380.

Monteleone et al., (2011), 'Aryl Hydrocarbon Receptor-Induced Signals Up-Regulate IL-22 Production and Inhibit Inflammation in the Gastrointestinal Tract,' Gastroenterology, 141(1):237-48.
Murray et al., (2010), 'Development of a Selective Modulator of Aryl Hydrocarbon (Ah) Receptor Activity that Exhibits Anti-Inflammatory Properties,' Chem Res Toxicol, 23(5):955-66 (NIH Public Access Author Manuscript).
Muscia et al., "Ultrasound Assisted Pictet-Spengler Synthesis of Tetrahydro-ß-Carboline Derivatives" Journal of Heterocyclic Chemistry (2016), 53(2),647-650.
Natarajan et al. (2003) "Highly efficient Lewis acid-catalysed Pictet-Spengler reactions discovered by parallel screening" Chem Commun., 7:916-17.
Negishi et al., (2005), 'Effects of Aryl Hydrocarbon Receptor Signaling on the Modulation of TH1/TH2 Balance,' J Immunol, 175(11):7348-56.
Nguyen and Bradfield, (2008), 'The Search for Endogenous Activators of the Aryl Hydrocarbon Receptor,' Chem Res Toxicol, 21(1): 102-16 [NIH Public Access Author Manuscript].
O'Donnell et al., (2010), 'The Anti-Inflammatory Drug Leflunomide is an Agonist of the Aryl Hydrocarbon Receptor,' PLoS One, 5(10):e13128 (13 pages).
Peng et al., "Design, synthesis and antidiabetic activity of novel tetrahydrocarboline PPAR regulators," Acta Pharmaceutica Sinica, Yaoxue Xuebao (2014), 49(4), 490-496.
Quintana et al., (2012), 'Aiolos Promotes TH17 Differentiation by Directly Silencing Il2 Expression,' Nat Immunol, 13(8):770-7 [NIH Public Access Author Manuscript].
Rannug et al., (1995), 'Structure Elucidation of Two Tryptophan-Derived, High Affinity Ah Receptor Ligands,' Chem Biol, 2(12):841-5.
Rieder, et al., Animal Models of Intestinal Fibrosis: New Tools for the Understanding of Pathogenesis and Therapy of Human Disease. American Journal of Physciology, Oct. 1, 2012; 303(7): G786-G801. Published online Aug. 9, 2012; https://www.ncbi.nlm.nih.gov/pmc/articles/PMC4073977/?report=printable.
Rodriguez-Sosa et al., (2005), 'Over-Production of IFN-γ and IL-12 in AhR-Null Mice,' FEBS Lett, 579(28):6403-10.
Shen et al., "The preparation and evaluation of 1-substituted 1,2,3,4-tetrahydro- and 3,4-dihydro-ß-carboline derivatives as potential antitumor agents," Chemical & Pharmaceutical Bulletin (2005), 53(1), 32-36.
Skinner et al., "Synthesis of 1-Aryl Substituted 9H-pyrido[3,4-b]indoles" Canadian Journal of Chemistry (1965), 43(8), 2251-3.
Somei M et al., (2001), 'The Chemistry of Indoles. CVII. A Novel Synthesis of 3,4,5,6,-tetrahydro-7-hydroxy-1H-azepino[5,4,3-cd]Indoles and a New Finding on Pictet-Spengler Reaction,' Chem Pharm Bull (Tokyo), 49(9):1159-65.
Spindler et al. "Synthesis and Investigation of Tetrahydro-ß-carboline Derivatives as Inhibitors of the Breast Cancer Resistance Protein (ABCG2)" Journal of Medicinal Chemistry (2016), 59(13), 6121-6135.
Stockringer B et al., (2011), 'External Influences on the Immune System via Activation of the Aryl Hydrocarbon Receptor,' Semin Immunol, 23(2):99-105.
Sugimoto et al., (2008), 'IL-22 Ameliorates Intestinal Inflammation in a Mouse Model of Ulcerative Colitis,' J Clin Invest, 118(2):534-44.
Sui et al., "Pyrimidinylpyrroloquinolones as Highly Potent and Selective PDE5 Inhibitors for Treatment of Erectile Dysfunction" Journal of Medicinal Chemistry (2002), 45(19), 4094-4096.
Sui et al., "Synthesis and biological activities of novel ß-Carbolines as PDE5 Inhibitors" Bioorganic & Medicinal Chemistry Letters (2003), 13(4), 761-765.
Tailleux A et al., (2005), 'Increased Susceptibility of Low-Density Lipoprotein to ex vivo Oxidation in Mice Transgenic for Human Apolipoprotein B Treated with 1 Melatonin-Related Compound is not Associated with Atherosclerosis Progression,' J Cardiovasc Pharmacol, 46(3):241-9.
Trifari et al., (2009), 'Identification of a Human Helper T Cell Population that has Abundant Production of Interleukin 22 and is Distinct from T(H)-17, T(H) 1 and T(H)2 Cells,' Nat Immunol, 10(8):864-71.

(56) References Cited

OTHER PUBLICATIONS

Veldhoen et al., (2008), 'The Aryl Hydrocarbon Receptor Links TH17-Cell-Mediated Autoimmunity to Environmental Toxins,' Nature, 453(7191):106-9.
Written Opinion of the International Searching Authority for International Application No. PCT/EP2015/064613, mailed Nov. 25, 2015 (9 pages).

* cited by examiner

Fig. 1

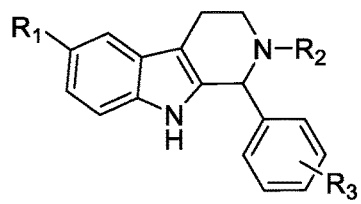

| N° | Compound | $R_1$ | $R_2$ | $R_3$ |
|---|---|---|---|---|
| 1 | CTL 01-07-L-A03 | H | H | H |
| 2 | CTL 01 07-L-A04 | H | H | 3 OCH₃ |
| 3 | CTL 01-07-L-A05 | OCH₃ | H | H |
| 4 | CTL 01-07-LA06 | OCH₃ | H | 3 OCH₃ |
| 5 | CTL 01-07-L-A07 | C₂H₅ | H | H |
| 6 | CTL 0107-L-A08 | C₂H₅ | H | 3 OCH₃ |
| 7 | CTL 01-07-L-A09 | OCH₃ | COCH₃ | H |
| 8 | CTL 0107-L-A10 | OCH₃ | COCH₃ | 3 OCH₃ |
| 9 | CTL 01-07-L-A11 | C₂H₅ | COCH₃ | H |
| 10 | CTL 01-07-L-B02 | C₂H₅ | COCH₃ | 3 OCH₃ |
| 11 | CTL 0107-L-B03 | H | C₃H₇ | 3 OCH₃ |
| 12 | CTL 01-07-L-B04 | OCH₃ | C₃H₇ | 3 OCH₃ |
| 13 | CTL 0107-L-B05 | C₂H₅ | C₃H₇ | 3 OCH₃ |
| 14 | CTL 10-26-L-A05 | OH | C₃H₇ | 3 OCH₃ |
| 15 | CTL 10-26-L-A06 | OBz | H | 3 OCH₃ |
| 16 | CTL 10-26-L-A07 | OBz | C₃H₇ | 3 OCH₃ |
| 17 | CTL 10-26-L-A11 | H | H | 4 COOCH₃ |
| 18 | CTL 10-26-L-E02 | H | H | 3 OH, 4 NO₂ |
| 19 | CTL 10-26-L-B03 | H | H | 4 CH₃ |
| 20 | CTL 10-26-L-B04 | H | H | 3 OCOCH₃ |
| 21 | CTL 10-26-L-B05 | H | H | 3 NO₂ |
| 22 | CTL 10-26-L-B08 | OBz | H | 3 OCOCH₃ |
| 23 | CTL 10-26-L-C06 | C₂H₅ | H | 3,4,5 OCH₃ |
| 24 | CTL 10-26-L-C07 | H | H | 3,5 C(CH₃)₃ 4 OCH₃ |
| 25 | CTL 10-26-L-C08 | C₂H₅ | H | 3,4 OCH₃ |
| 26 | CTL 10-26-L-C09 | H | H | 3,4,5 OCH₃ |
| 27 | CTL 10-26-L-C10 | C₂H₅ | H | 2 OCH₃ |
| 28 | CTL 10-26-L-D11 | C₂H₅ | H | 3,4 OBz |
| 29 | CTL 10-26-L-F07 | C₂H₅ | H | 4 OCH₃ |
| 30 | CTL 10-26-L-F09 | C₂H₅ | C₃H₇ | 2 OCH₃ |
| 31 | CTL 10-26-L-G09 | H | COCH₃ | H |
| 32 | CTL 10-26-L-G10 | C₂H₅ | H | 3,4,5 OCH₃ |
| 33 | CTL 10-26-L-G11 | H | H | 3 NH₂ |
| 34 | CTL 10-26-L-H02 | C₂H₅ | C₅H₁₁ | 3 OCH₃ |

Fig. 1 (Continued)

| N° | Compound | $R_1$ | $R_2$ | $R_3$ |
|---|---|---|---|---|
| 35 | CTL 10-26-L-H03 | $C_2H_5$ | $C_3H_7$ | $OB_z$ |
| 36 | CTL 10-26-L-H04 | $C_2H_5$ | $C_3H_7$ | 3,4 $OCH_3$ |
| 37 | CTL 10 26-L-H05 | $C_2H_5$ | $C_3H_7$ | 4 $OCH_3$ |
| 38 | CTL 10-26-L-H06 | H | H | 3,4 $OCH_3$ |
| 39 | CTL 10-26-L-H07 | H | H | 3 $OB_z$ |
| 40 | CTL 10-26-L-H08 | H | H | 3 OH |
| 41 | CTL 10-26-L-H09 | $C_2H_5$ | $COOB_z$ | 3,4 $OB_z$ |
| 42 | CTL 10-26-L-H10 | $C_2H_5$ | H | 3 $OB_z$ |
| 43 | CTL 10-26-L-H11 | H | H | 3,5 $C(CH_3)_3$ 4 OH |
| 44 | CTL 10-29-L-A02 | H | $COOB_z$ | 3 $OB_z$ |
| 45 | CTL 10-29-L-A03 | $C_2H_5$ | H | 3,4 -O-$(CH_2)_2$-O- |
| 46 | CTL 10-29-L-A04 | $C_2H_5$ | H | 3 OH |
| 47 | CTL 10-29-L-A05 | $C_2H_5$ | $C_3H_7$ | 3,4,5 $OCH_3$ |

Fig. 7
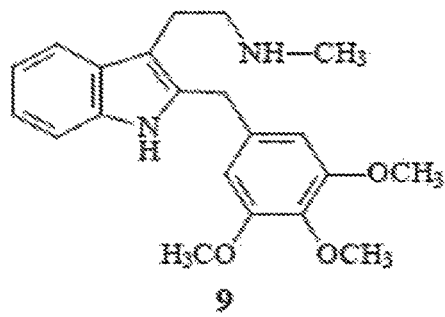
9
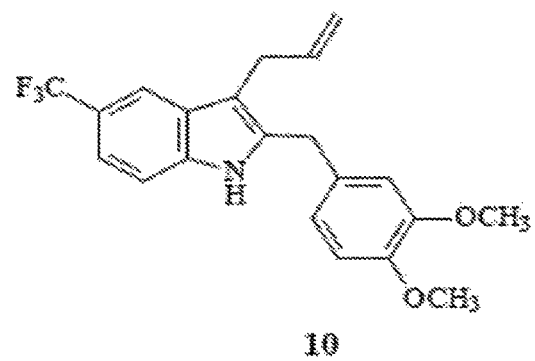
10
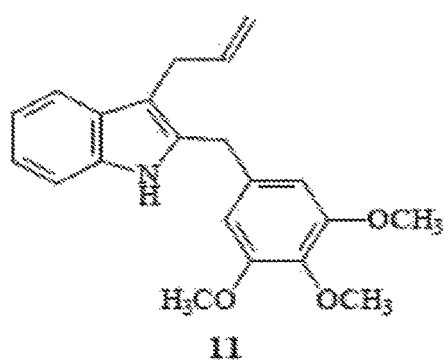
11
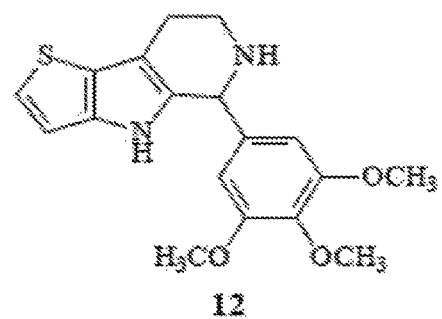
12
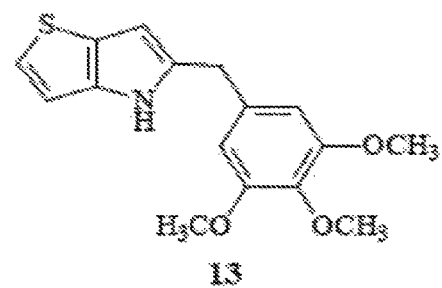
13
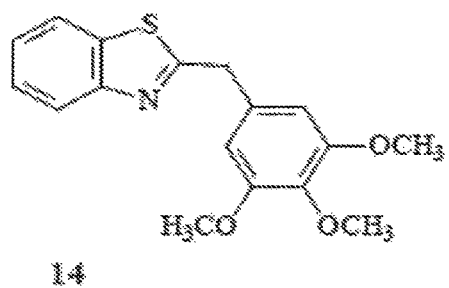
14
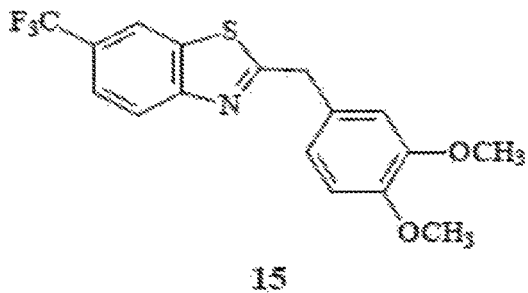
15
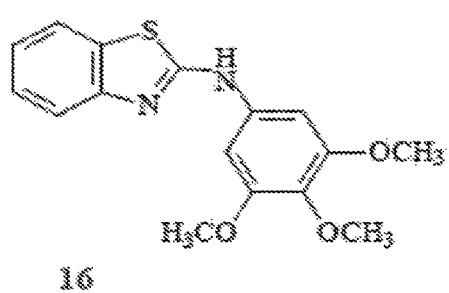
16

Fig. 10

| Compound | Human oral bioavailability (%) | P (> 30 %) | P (> 70 %) |
|---|---|---|---|
| 1 | 30 < < 70 | 0.811 | 0.205 |
| 2 | 30 < < 70 | 0.811 | 0.205 |
| 3 | 30 < < 70 | 0.811 | 0.205 |
| 4 | 30 < < 70 | 0.811 | 0.286 |
| 4a | 30 < < 70 | 0.811 | 0.286 |
| 5 | 30 < < 70 | 0.811 | 0.286 |
| 6 | 30 < < 70 | 0.811 | 0.286 |
| 7 | 30 < < 70 | 0.811 | 0.205 |
| 8 | 30 < < 70 | 0.759 | 0.205 |
| 9 | 30 < < 70 | 0.759 | 0.385 |
| 10 | 30 < < 70 | 0.811 | 0.205 |
| 11 | 30 < < 70 | 0.811 | 0.205 |
| 12 | 30 < < 70 | 0.849 | 0.336 |
| 13 | 30 < < 70 | 0.811 | 0.205 |
| 14 | 30 < < 70 | 0.811 | 0.205 |
| 15 | 30 < < 70 | 0.811 | 0.205 |
| 16 | 30 < < 70 | 0.811 | 0.286 |
| 17 | 30 < < 70 | 0.849 | 0.463 |
| 18 | 30 < < 70 | 0.811 | 0.358 |
| 19 | > 70 | 0.888 | 0.843 |
| 20 | > 70 | 0.811 | 0.785 |
| 21 | 30 < < 70 | 0.888 | 0.450 |
| 22 | 30 < < 70 | 0.913 | 0.843 |
| 23 | 30 < < 70 | 0.913 | 0.843 |
| 24 | >70 | 0.913 | 0.820 |
| 25 | 30 < < 70 | 0.811 | 0.205 |
| 26 | 30 < < 70 | 0.811 | 0.205 |
| 27 | 30 < < 70 | 0.811 | 0.205 |
| CTL | 30 < < 70 | 0.811 | 0.286 |
| Leflunomide | > 70 | 0.950 | 0.924 |

Fig. 11A

| Compound | log Sw (log Mol/l) |
|---|---|
| 1 | -5.20 |
| 2 | -5.20 |
| 3 | -6.00 |
| 4 | -5.20 |
| 4a | -5.20 |
| 5 | -4.75 |
| 6 | -4.08 |
| 7 | -5.51 |
| 8 | -4.85 |
| 9 | -4.07 |
| 10 | -5.76 |
| 11 | -4.98 |
| 12 | -3.50 |
| 13 | -4.17 |
| 14 | -4.32 |
| 15 | -5.22 |
| 16 | -4,10 |
| 17 | -3.40 |
| 18 | -3.94 |
| 19 | -4.13 |
| 20 | -3.94 |
| 21 | -4.22 |
| 22 | -3.33 |
| 23 | -2.58 |
| 24 | -3.10 |
| 25 | -6.74 |
| 26 | -6.76 |
| 27 | -4.42 |
| CTL | -4.20 |
| Leflunomide | -2.97 |

Fig. 11B

| Compound | Sw (g/l) | log Sw (log Mol/l) |
|---|---|---|
| 1 | 2.4 | -5.20 |
| 2 | 0.038 | -6.99 |
| 3 | 0.034 | -6.00 |
| 4 | 0.021 | -5.20 |
| 5 | 6.1 | -4.75 |
| 6 | 28 | -4.08 |
| 7 | 1 | -5.51 |
| 8 | 5.6 | -4.85 |
| 9 | 31 | -4.07 |
| 10 | 0.066 | -5.76 |
| 11 | 0.036 | -4.98 |
| 12 | 0.110 | -3.50 |
| 13 | 21 | -4.17 |
| 14 | 15 | -4.32 |
| 15 | 2.1 | -5.22 |
| 16 | 25 | -4,10 |
| 17 | 120 | -3.40 |
| 18 | 39 | -3.94 |
| 19 | 25 | -4.13 |
| 20 | 39 | -3.94 |
| 21 | 21 | -4.22 |
| 22 | 140 | -3.33 |
| 23 | 790 | -2.58 |
| 24 | 240 | -3.10 |
| 25 | 0.068 | -6.74 |
| 26 | 0.060 | -6.76 |
| 27 | 14 | -4.42 |
| CTL | 21 | -4.20 |
| Leflunomide | 29 | -2.97 |

Fig. 12A

| Compound | log S (log Mol/l) | | | | |
|---|---|---|---|---|---|
| | pH = 1.7 (stomach) | pH = 4.6 (duodenum) | pH = 6.5 (jejunum & ileon) | pH = 7.4 (blood) | pH = 8.0 (colon) |
| 1 | -2.20 | -2.53 | -4.35 | -4.93 | -5.08 |
| 2 | -2.20 | -2.53 | -4.36 | -4.94 | -5.10 |
| 3 | -6.00 | -6.00 | -6.00 | -6.00 | -6.00 |
| 4 | -2.63 | -4.65 | -5.01 | -5.02 | -5.02 |
| 4 | -5.36 | -5.42 | -5.42 | -5.42 | -5.42 |
| 5 | -4.69 | -4.75 | -4.75 | -4.75 | -4.75 |
| 6 | -1.08 | -1.08 | -1.57 | -2.46 | -3.03 |
| 7 | -2.51 | -3.78 | -5.29 | -5.48 | -5.51 |
| 8 | -1.85 | -1.85 | -1.85 | -2.61 | -3.21 |
| 9 | -1.07 | -1.07 | -1.06 | -1.73 | -2.32 |
| 10 | -5.76 | -5.76 | -5.76 | -5.76 | -5.76 |
| 11 | -4.98 | -4.98 | -4.98 | -4.98 | -4.98 |
| 12 | -0.58 | -0.58 | -1.22 | -2.09 | -2.59 |
| 13 | -4.17 | -4.17 | -4.17 | -4.17 | -4.17 |
| 14 | -4.32 | -4.32 | -4.32 | -4.32 | -4.32 |
| 15 | -5.20 | -5.22 | -5.22 | -5.22 | -5.22 |
| 16 | -3.73 | -4.10 | -4.10 | -4.10 | -4.10 |
| 17 | -0.50 | -0.50 | -1.38 | -2.25 | -2.77 |
| 18 | -3.94 | -3.94 | -3.94 | -3.94 | -3.94 |
| 19 | -4.13 | -4.13 | -4.13 | -4.13 | -4.13 |
| 20 | -3.94 | -3.94 | -3.94 | -3.94 | -3.94 |
| 21 | -4.20 | -4.22 | -4.22 | -4.22 | -4.22 |
| 22 | -3.32 | -3.33 | -3.33 | -3.33 | -3.33 |
| 23 | 0.07 | -1.42 | -2.51 | -2.57 | -2.58 |
| 24 | -3.10 | -3.10 | -3.10 | -3.10 | -3.10 |
| 25 | -6.74 | -6.74 | -6.74 | -6.74 | -6.74 |
| 26 | -6.76 | -6.76 | -6.76 | -6.76 | -6.76 |
| 27 | -1.00 | -1.42 | -3.01 | -3.81 | -4.17 |
| CTL | -1.20 | -1.47 | -3.31 | -3.93 | -4.10 |
| Leflunomide | -2.97 | -2.97 | -2.97 | -2.97 | -2.97 |

Fig. 12B

| Compound | log S (log Mol/l) | | | | |
|---|---|---|---|---|---|
| | pH = 1.7 (stomach) | pH = 4.6 (duodenum) | pH = 6.5 (jejunum & ileon) | pH = 7.4 (blood) | pH = 8.0 (colon) |
| 1 | -2.20 | -2.53 | -4.35 | -4.93 | -5.08 |
| 2 | -6.93 | -6.93 | -6.93 | -6.93 | -6.93 |
| 3 | -6.00 | -6.00 | -6.00 | -6.00 | -6.00 |
| 4 | -2.63 | -4.65 | -5.01 | -5.02 | -5.02 |
| 5 | -4.69 | -4.75 | -4.75 | -4.75 | -4.75 |
| 6 | -1.08 | -1.08 | -1.57 | -2.46 | -3.03 |
| 7 | -2.51 | -3.78 | -5.29 | -5.48 | -5.51 |
| 8 | -1.85 | -1.85 | -1.85 | -2.61 | -3.21 |
| 9 | -1.07 | -1.07 | -1.06 | -1.73 | -2.32 |
| 10 | -5.76 | -5.76 | -5.76 | -5.76 | -5.76 |
| 11 | -4.98 | -4.98 | -4.98 | -4.98 | -4.98 |
| 12 | -0.58 | -0.58 | -1.22 | -2.09 | -2.59 |
| 13 | -4.17 | -4.17 | -4.17 | -4.17 | -4.17 |
| 14 | -4.32 | -4.32 | -4.32 | -4.32 | -4.32 |
| 15 | -5.20 | -5.22 | -5.22 | -5.22 | -5.22 |
| 16 | -3.73 | -4.10 | -4.10 | -4.10 | -4.10 |
| 17 | -0.50 | -0.50 | -1.38 | -2.25 | -2.77 |
| 18 | -3.94 | -3.94 | -3.94 | -3.94 | -3.94 |
| 19 | -4.13 | -4.13 | -4.13 | -4.13 | -4.13 |
| 20 | -3.94 | -3.94 | -3.94 | -3.94 | -3.94 |
| 21 | -4.20 | -4.22 | -4.22 | -4.22 | -4.22 |
| 22 | -3.32 | -3.33 | -3.33 | -3.33 | -3.33 |
| 23 | 0.07 | -1.42 | -2.51 | -2.57 | -2.58 |
| 24 | -3.10 | -3.10 | -3.10 | -3.10 | -3.10 |
| 25 | -6.74 | -6.74 | -6.74 | -6.74 | -6.74 |
| 26 | -6.76 | -6.76 | -6.76 | -6.76 | -6.76 |
| 27 | -1.00 | -1.42 | -3.01 | -3.81 | -4.17 |
| CTL | -1.20 | -1.47 | -3.31 | -3.93 | -4.10 |
| Leflunomide | -3.60 | -3.60 | -3.60 | -3.60 | -3.60 |

Fig. 13

| Compound | Maximum absorption (%) | Permeability (cm/s) | | Absorption rate (min$^{-1}$) |
|---|---|---|---|---|
| | | jejunum | Caco-2 | |
| 1 | 100 | $3.44\ 10^{-4}$ | $193\ 10^{-6}$ | 0.094 |
| 2 | 100 | $3.44\ 10^{-4}$ | $193\ 10^{-6}$ | 0.094 |
| 3 | 100 | $5.99\ 10^{-4}$ | $240\ 10^{-6}$ | 0.101 |
| 4 | 100 | $4.96\ 10^{-4}$ | $235\ 10^{-6}$ | 0.100 |
| 4a | 100 | $5.83\ 10^{-4}$ | $242\ 10^{-6}$ | 0.101 |
| 5 | 100 | $4.09\ 10^{-4}$ | $212\ 10^{-6}$ | 0.097 |
| 6 | 100 | $1.81\ 10^{-4}$ | $41\ 10^{-6}$ | 0.063 |
| 7 | 100 | $4.78\ 10^{-4}$ | $234\ 10^{-6}$ | 0.099 |
| 8 | 100 | $4.27\ 10^{-4}$ | $74\ 10^{-6}$ | 0.098 |
| 9 | 100 | $2.54\ 10^{-4}$ | $61\ 10^{-6}$ | 0.082 |
| 10 | 100 | $6.06\ 10^{-4}$ | $205\ 10^{-6}$ | 0.101 |
| 11 | 100 | $5.06\ 10^{-4}$ | $235\ 10^{-6}$ | 0.100 |
| 12 | 100 | $2.50\ 10^{-4}$ | $78\ 10^{-6}$ | 0.082 |
| 13 | 100 | $4.42\ 10^{-4}$ | $233\ 10^{-6}$ | 0.098 |
| 14 | 100 | $4.59\ 10^{-4}$ | $241\ 10^{-6}$ | 0.099 |
| 15 | 100 | $5.67\ 10^{-4}$ | $244\ 10^{-6}$ | 0.101 |
| 16 | 100 | $4.76\ 10^{-4}$ | $235\ 10^{-6}$ | 0.099 |
| 17 | 100 | $2.55\ 10^{-4}$ | $94\ 10^{-6}$ | 0.082 |
| 18 | 100 | $4.45\ 10^{-4}$ | $233\ 10^{-6}$ | 0.099 |
| 19 | 100 | $4.30\ 10^{-4}$ | $231\ 10^{-6}$ | 0.098 |
| 20 | 100 | $4.45\ 10^{-4}$ | $233\ 10^{-6}$ | 0.099 |
| 21 | 100 | $4.64\ 10^{-4}$ | $234\ 10^{-6}$ | 0.099 |
| 22 | 100 | $3.27\ 10^{-4}$ | $211\ 10^{-6}$ | 0.092 |
| 23 | 100 | $1.88\ 10^{-4}$ | $144\ 10^{-6}$ | 0.065 |
| 24 | 100 | $3.08\ 10^{-4}$ | $205\ 10^{-6}$ | 0.090 |
| 25 | 100 | $6.59\ 10^{-4}$ | $170\ 10^{-6}$ | 0.101 |
| 26 | 100 | $6.67\ 10^{-4}$ | $132\ 10^{-6}$ | 0.101 |
| 27 | 100 | $4.30\ 10^{-4}$ | $206\ 10^{-6}$ | 0.098 |
| CTL | 100 | $2.56\ 10^{-4}$ | $164\ 10^{-6}$ | 0.083 |
| Leflunomide | 100 | $3.95\ 10^{-4}$ | $229\ 10^{-6}$ | 0.097 |

Fig. 14

| Compound | PepT1 | ASBT |
|---|---|---|
| 1 | not transported | not transported |
| 2 | not transported | not transported |
| 3 | not transported | not transported |
| 4 | not transported | not transported |
| 4a | not transported | not transported |
| 5 | not transported | not transported |
| 6 | not transported | not transported |
| 7 | not transported | not transported |
| 8 | not transported | not transported |
| 9 | not transported | not transported |
| 10 | not transported | not transported |
| 11 | not transported | not transported |
| 12 | not transported | not transported |
| 13 | not transported | not transported |
| 14 | not transported | not transported |
| 15 | not transported | not transported |
| 16 | not transported | not transported |
| 17 | not transported | not transported |
| 18 | not transported | not transported |
| 19 | not transported | not transported |
| 20 | not transported | not transported |
| 21 | not transported | not transported |
| 22 | not transported | not transported |
| 23 | not transported | not transported |
| 24 | not transported | not transported |
| 25 | not transported | not transported |
| 26 | not transported | not transported |
| 27 | not transported | not transported |
| CTL | not transported | not transported |
| Leflunomide | not transported | not transported |

Fig. 15

| Compound | P(P-gp substrate) | P(P-gp inhibitor) |
|---|---|---|
| 1 | 0.270 | 0.553 |
| 2 | 0.270 | 0.553 |
| 3 | 0.240 | 0.386 |
| 4 | 0.190 | 0.386 |
| 4a | 0.230 | 0.385 |
| 5 | 0.121 | 0.330 |
| 6 | 0.199 | 0.260 |
| 7 | 0.150 | 0.263 |
| 8 | 0.650 | 0.647 |
| 9 | 0.590 | 0.446 |
| 10 | 0.320 | 0.602 |
| 11 | 0.290 | 0.471 |
| 12 | 0.220 | 0.345 |
| 13 | 0.150 | 0.239 |
| 14 | 0.150 | 0.200 |
| 15 | 0.300 | 0.353 |
| 16 | 0.260 | 0.186 |
| 17 | 0.209 | 0.280 |
| 18 | 0.140 | 0.480 |
| 19 | 0.220 | 0.331 |
| 20 | 0.140 | 0.480 |
| 21 | 0.180 | 0.480 |
| 22 | 0.150 | 0.480 |
| 23 | 0.160 | 0.103 |
| 24 | 0.130 | 0.108 |
| 25 | 0.240 | 0.630 |
| 26 | 0.140 | 0.531 |
| 27 | 0.220 | 0.388 |
| CTL | 0.250 | 0.363 |
| Leflunomide | 0.280 | 0.124 |

Fig. 16

| Compound | Plasma protein binding (%) | Volume of distribution (human) (l/kg) |
|---|---|---|
| 1 | 83 | 3.7 |
| 2 | 83 | 3.7 |
| 3 | 98 | 2.8 |
| 4 | 94 | 2.2 |
| 4a | 95 | 2.4 |
| 5 | 96 | 2.0 |
| 6 | 84 | 3.0 |
| 7 | 98 | 2.1 |
| 8 | 88 | 8.3 |
| 9 | 85 | 5.4 |
| 10 | 85 | 4.2 |
| 11 | 96 | 2.5 |
| 12 | 77 | 5.5 |
| 13 | 83 | 2.2 |
| 14 | 92 | 2.3 |
| 15 | 99 | 2.9 |
| 16 | 97 | 2.1 |
| 17 | 96 | 3.0 |
| 18 | 91 | 2.3 |
| 19 | 92 | 2.1 |
| 20 | 91 | 2.1 |
| 21 | 94 | 2.2 |
| 22 | 89 | 1.4 |
| 23 | 79 | 1.3 |
| 24 | 85 | 1.4 |
| 25 | 99.5 | 3.8 |
| 26 | 99.5 | 4.2 |
| 27 | 99 | 4.9 |
| CTL | 82 | 2.7 |
| Leflunomide | 89 | 1.5 |

Fig. 17

| Compound | CYP3A4 P(inhibitor) IC$_{50}$ < 10 μM | CYP2D6 P(inhibitor) IC$_{50}$ < 10 μM | CYP2C9 P(inhibitor) IC$_{50}$ < 10 μM | CYP2C19 P(inhibitor) IC$_{50}$ < 10 μM | CYP1A2 P(inhibitor) IC$_{50}$ < 10 μM |
|---|---|---|---|---|---|
| 1 | 0.11 | 0.59 | 0.06 | 0.50 | 0.29 |
| 2 | 0.11 | 0.59 | 0.06 | 0.50 | 0.29 |
| 3 | 0.20 | 0.09 | 0.13 | 0.47 | 0.98 |
| 4 | 0.07 | 0.10 | 0.12 | 0.49 | 0.88 |
| 4a | 0.10 | 0.09 | 0.11 | 0.34 | 0.69 |
| 5 | 0.26 | 0.15 | 0.13 | 0.25 | 0.96 |
| 6 | 0.09 | 0.68 | 0.04 | 0.14 | 0.65 |
| 7 | 0.22 | 0.04 | 0.06 | 0.35 | 0.96 |
| 8 | 0.53 | 0.30 | 0.13 | 0.22 | 0.21 |
| 9 | 0.28 | 0.56 | 0.17 | 0.23 | 0.28 |
| 10 | 0.73 | 0.21 | 0.25 | 0.73 | 0.78 |
| 11 | 0.67 | 0.17 | 0.37 | 0.71 | 0.84 |
| 12 | 0.26 | 0.53 | 0.14 | 0.47 | 0.76 |
| 13 | 0.60 | 0.19 | 0.42 | 0.53 | 0.95 |
| 14 | 0.25 | 0.12 | 0.11 | 0.51 | 0.67 |
| 15 | 0.45 | 0.11 | 0.12 | 0.52 | 0.59 |
| 16 | 0.21 | 0.10 | 0.03 | 0.23 | 0.64 |
| 17 | 0.32 | 0.08 | 0.05 | 0.32 | 0.72 |
| 18 | 0.26 | 0.04 | 0.16 | 0.29 | 0.26 |
| 19 | 0.21 | 0.03 | 0.06 | 0.35 | 0.36 |
| 20 | 0.26 | 0.04 | 0.16 | 0.29 | 0.26 |
| 21 | 0.15 | 0.03 | 0.06 | 0.39 | 0.42 |
| 22 | 0.22 | 0.04 | 0.04 | 0.30 | 0.68 |
| 23 | 0.46 | 0.02 | 0.07 | 0.32 | 0.59 |
| 24 | 0.36 | 0.07 | 0.09 | 0.25 | 0.71 |
| 25 | 0.44 | 0.05 | 0.63 | 0.73 | 0.89 |
| 26 | 0.48 | 0.04 | 0.65 | 0.81 | 0.95 |
| 27 | 0.40 | 0.03 | 0.06 | 0.22 | 0.74 |
| CTL | 0.05 | 0.72 | 0.06 | 0.39 | 0.39 |
| Leflunomide | 0.03 | 0.02 | 0.03 | 0.06 | 0.80 |

Fig. 18

| Compound | P(Ames mutagenesis) |
|---|---|
| 1 | 0.374 |
| 2 | 0.121 |
| 3 | 0.431 |
| 4 | 0.336 |
| 4a | 0.446 |
| 5 | 0.540 |
| 6 | 0.432 |
| 7 | 0.639 |
| 8 | 0.092 |
| 9 | 0.301 |
| 10 | 0.150 |
| 11 | 0.403 |
| 12 | 0.195 |
| 13 | 0.225 |
| 14 | 0.239 |
| 15 | 0.119 |
| 16 | 0.412 |
| 17 | 0.288 |
| 18 | 0.045 |
| 19 | 0.100 |
| 20 | 0.045 |
| 21 | 0.063 |
| 22 | 0.254 |
| 23 | 0.194 |
| 24 | 0.300 |
| 25 | 0.482 |
| 26 | 0.583 |
| 27 | 0.719 |
| CTL | 0.211 |
| Leflunomide | 0.140 |

Fig. 19

| Compound | P(hErg inhibitor) (Ki < 10 μM, patch-clamp) |
|---|---|
| 1 | 0.98 |
| 2 | 0.93 |
| 3 | 0.88 |
| 4 | 0.92 |
| 4a | 0.92 |
| 5 | 0.82 |
| 6 | 0.88 |
| 7 | 0.80 |
| 8 | 0.97 |
| 9 | 0.90 |
| 10 | 0.90 |
| 11 | 0.72 |
| 12 | 0.29 |
| 13 | 0.18 |
| 14 | 0.39 |
| 15 | 0.76 |
| 16 | 0.58 |
| 17 | 0.62 |
| 18 | 0.50 |
| 19 | 0.69 |
| 20 | 0.50 |
| 21 | 0.75 |
| 22 | 0.35 |
| 23 | 0.16 |
| 24 | 0.11 |
| 25 | 0.92 |
| 26 | 0.91 |
| 27 | 0.68 |
| CTL | 0.80 |
| Leflunomide | 0.31 |

Fig. 20

| Compound | Blood | Cardiovascular system | Gastrointestinal system | Kidney | Liver | Lungs |
|---|---|---|---|---|---|---|
| 1 | 0.89 | 0.94 | 0.57 | 0.48 | 0.51 | 0.97 |
| 2 | 0.63 | 0.99 | 0.91 | 0.65 | 0.91 | 0.75 |
| 3 | 0.65 | 0.92 | 0.52 | 0.37 | 0.44 | 0.97 |
| 4 | 0.49 | 0.97 | 0.99 | 0.47 | 0.78 | 0.34 |
| 4a | 0.24 | 0.87 | 0.68 | 0.31 | 0.34 | 0.46 |
| 5 | 0.46 | 0.97 | 0.99 | 0.49 | 0.88 | 0.30 |
| 6 | 0.55 | 0.99 | 0.90 | 0.58 | 0.88 | 0.77 |
| 7 | 0.83 | 0.98 | 0.92 | 0.74 | 0.84 | 0.97 |
| 8 | 0.72 | 0.99 | 0.79 | 0.78 | 0.73 | 0.92 |
| 9 | 0.97 | 0.99 | 0.66 | 0.82 | 0.57 | 0.99 |
| 10 | 0.95 | 0.98 | 0.68 | 0.87 | 0.87 | 0.47 |
| 11 | 0.97 | 0.98 | 0.60 | 0.66 | 0.81 | 0.37 |
| 12 | 0.44 | 0.98 | 0.81 | 0.56 | 0.74 | 0.73 |
| 13 | 0.31 | 0.88 | 0.50 | 0.34 | 0.35 | 0.28 |
| 14 | 0.49 | 0.91 | 0.39 | 0.19 | 0.07 | 0.28 |
| 15 | 0.30 | 0.93 | 0.34 | 0.55 | 0.14 | 0.44 |
| 16 | 0.25 | 0.95 | 0.42 | 0.20 | 0.04 | 0.27 |
| 17 | 0.44 | 0.99 | 0.99 | 0.76 | 0.62 | 0.76 |
| 18 | 0.15 | 0.82 | 0.29 | 0.24 | 0.20 | 0.31 |
| 19 | 0.16 | 0.82 | 0.33 | 0.26 | 0.20 | 0.31 |
| 20 | 0.15 | 0.82 | 0.29 | 0.24 | 0.20 | 0.31 |
| 21 | 0.21 | 0.82 | 0.28 | 0.26 | 0.20 | 0.31 |
| 22 | 0.13 | 0.61 | 0.77 | 0.18 | 0.13 | 0.16 |
| 23 | 0.55 | 0.78 | 0.27 | 0.19 | 0.12 | 0.11 |
| 24 | 0.12 | 0.75 | 0.48 | 0.44 | 0.28 | 0.10 |
| 25 | 0.40 | 0.89 | 0.99 | 0.33 | 0.52 | 0.96 |
| 26 | 0.40 | 0.88 | 0.68 | 0.37 | 0.53 | 0.42 |
| 27 | 0.90 | 0.97 | 0.91 | 0.66 | 0.07 | 0.95 |
| CTL | 0.55 | 0.98 | 0.91 | 0.53 | 0.89 | 0.57 |
| Leflunomide | 0.21 | 0.89 | 0.09 | 0.35 | 0.39 | 0.20 |

Fig. 21

| Compound | LD50 mouse (mg/kg) | | | | LD50 rat (mg/kg) | |
|---|---|---|---|---|---|---|
| | Intraperitoneal | Oral | Intravenous | Subcutaneous | Intraperitoneal | Oral |
| 1 | 330 | 680 | 30 | 130 | 410 | 940 |
| 2 | 130 | 350 | 27 | 150 | 120 | 230 |
| 3 | 280 | 830 | 35 | 180 | 440 | 1400 |
| 4 | 400 | 430 | 33 | 270 | 280 | 970 |
| 4a | 350 | 560 | 44 | 270 | 240 | 1600 |
| 5 | 260 | 570 | 43 | 380 | 580 | 980 |
| 6 | 360 | 430 | 32 | 420 | 130 | 570 |
| 7 | 360 | 310 | 63 | 290 | 290 | 1100 |
| 8 | 70 | 350 | 38 | 110 | 130 | 170 |
| 9 | 140 | 390 | 37 | 270 | 140 | 320 |
| 10 | 270 | 370 | 50 | 110 | 630 | 760 |
| 11 | 280 | 240 | 30 | 220 | 430 | 1100 |
| 12 | 130 | 370 | 38 | 170 | 200 | 72 |
| 13 | 250 | 460 | 54 | 350 | 300 | 410 |
| 14 | 220 | 1100 | 67 | 270 | 440 | 2000 |
| 15 | 330 | 630 | 70 | 210 | 360 | 1000 |
| 16 | 410 | 840 | 130 | 250 | 380 | 1600 |
| 17 | 240 | 1600 | 77 | 390 | 350 | 390 |
| 18 | 330 | 1100 | 73 | 230 | 400 | 2500 |
| 19 | 280 | 940 | 87 | 300 | 1200 | 1900 |
| 20 | 330 | 1100 | 73 | 230 | 400 | 2500 |
| 21 | 470 | 1100 | 120 | 730 | 510 | 4900 |
| 22 | 370 | 2800 | 78 | 830 | 650 | 2400 |
| 23 | 300 | 2400 | 66 | 790 | 700 | 2400 |
| 24 | 540 | 2100 | 100 | 620 | 730 | 3900 |
| 25 | 360 | 710 | 28 | 63 | 560 | 190 |
| 26 | 350 | 690 | 26 | 64 | 490 | 160 |
| 27 | 400 | 780 | 76 | 550 | 530 | 1200 |
| CTL | 330 | 370 | 22 | 220 | 150 | 390 |
| Leflunomide | 480 | 740 | 150 | 590 | 760 | 620 |

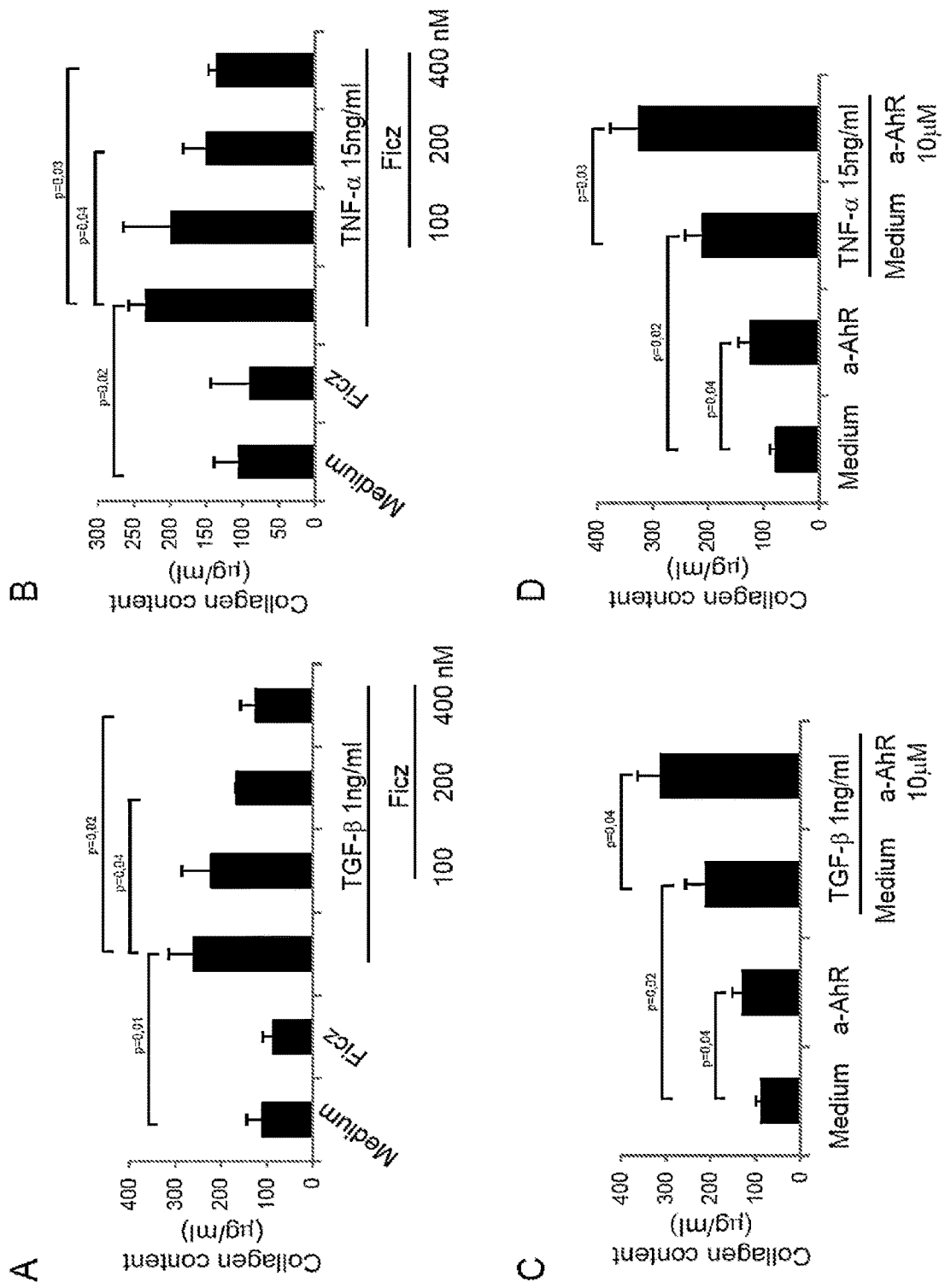
Fig. 28 (A) – (D)

SEQUENCE LISTING

```
Sequence total quantity: 10
SEQ ID NO: 1           moltype = DNA  length = 20
FEATURE                Location/Qualifiers
source                 1..20
                       mol_type = other DNA
                       note = Human IFN-gamma forward primer
                       organism = synthetic construct
SEQUENCE: 1
tggagaccat caaggaagac                                                 20
```

-continued

```
SEQ ID NO: 2              moltype = DNA   length = 20
FEATURE                   Location/Qualifiers
source                    1..20
                          mol_type = other DNA
                          note = Human IFN-gamma reverse primer
                          organism = synthetic construct
SEQUENCE: 2
gcgttggaca ttcaagtcag                                                    20

SEQ ID NO: 3              moltype = DNA   length = 27
FEATURE                   Location/Qualifiers
source                    1..27
                          mol_type = other DNA
                          note = beta-actin forward primer
                          organism = synthetic construct
SEQUENCE: 3
aagatgaccc agatcatgtt tgagacc                                            27

SEQ ID NO: 4              moltype = DNA   length = 20
FEATURE                   Location/Qualifiers
source                    1..20
                          mol_type = other DNA
                          note = beta-actin reverse primer
                          organism = synthetic construct
SEQUENCE: 4
agccagtcca gacgcaggat                                                    20

SEQ ID NO: 5              moltype = DNA   length = 20
FEATURE                   Location/Qualifiers
source                    1..20
                          mol_type = other DNA
                          note = Human Col1A1 primer
                          organism = synthetic construct
SEQUENCE: 5
ggacacagag gtttcagtgg                                                    20

SEQ ID NO: 6              moltype = DNA   length = 21
FEATURE                   Location/Qualifiers
source                    1..21
                          mol_type = other DNA
                          note = Human Col3A1 primer
                          organism = synthetic construct
SEQUENCE: 6
ggagaatgtt gtgcagtttg c                                                  21

SEQ ID NO: 7              moltype = DNA   length = 20
FEATURE                   Location/Qualifiers
source                    1..20
                          mol_type = other DNA
                          note = Human alpha-SMA primer
                          organism = synthetic construct
SEQUENCE: 7
tctggagatg gtgtcaccca                                                    20

SEQ ID NO: 8              moltype = DNA   length = 20
FEATURE                   Location/Qualifiers
source                    1..20
                          mol_type = other DNA
                          note = human AhR forward primer
                          organism = synthetic construct
SEQUENCE: 8
gagcacaaat cagagactgg                                                    20

SEQ ID NO: 9              moltype = DNA   length = 20
FEATURE                   Location/Qualifiers
source                    1..20
                          mol_type = other DNA
                          note = Human AhR reverse primer
                          organism = synthetic construct
```

```
SEQUENCE: 9
tggaggaagc atagaagacc                                                  20

SEQ ID NO: 10           moltype = DNA  length = 20
FEATURE                 Location/Qualifiers
source                  1..20
                        mol_type = other DNA
                        note = mouse Col1A2 primer
                        organism = synthetic construct
SEQUENCE: 10
acacagtggt atggatggac                                                  20
```

ARYL RECEPTOR MODULATORS AND METHODS OF MAKING AND USING THE SAME

RELATED APPLICATIONS

This application is a continuation patent application of U.S. patent application Ser. No. 15/321,967, filed on Dec. 23, 2016, which application is the U.S. national stage application under 35 U.S.C. § 371 of International Application No. PCT/EP2015/064613, filed on Jun. 26, 2015, which claims priority to and the benefit of U.S. Provisional Application No. 62/017,959, filed on Jun. 27, 2014, and U.S. Provisional Application No. 62/056,054, filed on Sep. 26, 2014, the entire contents of each of which are incorporated by reference herein.

The instant application contains a Sequence Listing which has been submitted electronically in XML format and is hereby incorporated by reference in its entirety. Said XML copy, created on Feb. 21, 2023, is named GIU-040C1_SL.xml and is 11,691 bytes in size.

BACKGROUND

Aryl hydrocarbon receptor (AhR), a basic helix-loop-helix protein, is a member of the Per-ARNT-Sim (PAS) superfamily of proteins. Physiologically, many of these proteins act by sensing molecules and stimuli from the cellular/tissue microenvironment, thereby initiating signaling cascades necessary to elicit appropriate cellular responses.

In its inactive state, AhR resides in the cytosol bound to several co-chaperones, but after activation, it migrates into the nucleus and binds its dimerization partner, ARNT (another bHLH-PAS protein), thus initiating the transcription of a variety of genes with promoters containing a dioxin (DRE) or xenobiotic consensus sequence (XME). Pioneering studies in AhR-deficient mice have emphasized the role of AhR in the development and functions of various organs. More recent studies have shown that AhR controls specific immune responses (see, for example, Stockinger et al., *Semin. Immunol.* 2011, 23, 99-105).

AhR is highly expressed by T cells and controls Th1/Th2/Th17 cell-associated immunity. In humans and in mouse models of inflammatory bowel disease, activation of AhR led to a diminished expression of IFN-γ and T-bet, the main transcription factor that drives the Th1 polarization. The basic mechanism by which AhR inhibits IFN-γ production remains to be ascertained, however, it has been demonstrated that AhR signaling enhances Aiolos, a member of the Ikaros family, that negatively regulates IFN-γ production and colitis in mice. AhR activation in lymphoid cells can also regulate production of interleukin-22 (IL-22), a cytokine that can exert protective effects in various organs and time-course studies showed that suppression of IFN-γ and T-bet preceded IL-22 induction.

In light of the potential for selective AhR modulators to affect immunity and inflammation and thus treat a variety of inflammatory conditions, there exists a need for potent and selective compounds that modulate AhR activity.

SUMMARY

The present disclosure, in an embodiment, provides potent and selective AhR-binding compounds. In one aspect, the present disclosure provides a compound according to Formula I:

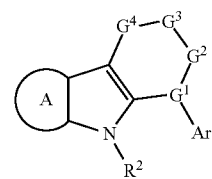

(I)

wherein the variables are as defined below.

In one aspect, the present disclosure relates to a compound according to Formula I-A:

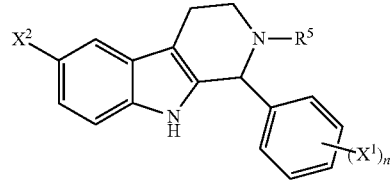

(I-A)

wherein the variables are as defined below.

In one aspect, the present disclosure relates to a compound according to Formula II:

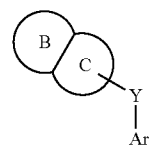

(II)

wherein the variables are as defined below.

In one aspect, the present disclosure relates to a compound according to Formula III:

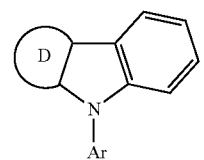

(III)

wherein the variables are as defined below.

In one aspect, the present disclosure relates to a compound according to Formula IV:

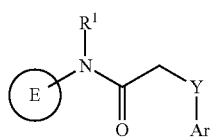

(IV)

wherein the variables are as defined below.

The present disclosure also provides methods of treating an inflammatory disease or condition, comprising administering to a subject in need thereof a therapeutically effective amount of a compound described above. In certain embodiments, the inflammatory disease or condition is selected from the group consisting of inflammatory bowel disease, cartilage inflammation, bone degradation, ulcerative colitis, psoriasis, arthritis, psoriatic arthritis, rheumatoid arthritis, juvenile arthritis, juvenile rheumatoid arthritis, autoimmune hepatitis, Crohn's disease, lupus erythematosus, multiple sclerosis, Alzheimer's disease, dermatitis, atopic dermatitis, acne, Type I diabetes mellitus, Raynaud's phenomenon, Graves' disease, and Addison's disease.

In certain embodiments, the inflammatory disease or condition is selected from the group consisting of Crohn's disease, ulcerative colitis, collagenous colitis, lymphocytic colitis, diversion colitis, Behçet's disease, idiopathic inflammatory bowel disease, irritable bowel syndrome, regional enteritis, spastic colon, microscopic colitis, Crohn's colitis, perianal disease, indeterminate colitis, lymphocytic gastritis, and eosinophilic enteritis.

In certain embodiments, the inflammatory disease or condition is Crohn's disease. In certain embodiments, the Crohn's disease is selected from the group consisting of ileocolitis, ileitis, gastroduodenal Crohn's disease, jejunoileitis, and granulomatous ileocolitis. In certain embodiments, the Crohn's disease includes intestinal fibrosis. In certain embodiments, the Crohn's disease is fibrostenotic Crohn's disease.

In another aspect, the present disclosure provides a method of preventing, treating, or reducing fibrostenosis or intestinal fibrosis in a subject, comprising administering to a subject in need thereof a therapeutically effective amount of a compound disclosed herein. In certain embodiments, the fibrostenosis or intestinal fibrosis is associated with Crohn's disease.

In another aspect, the present invention provides a compound as described above for use as a medicament. The present invention further provides a compound as described above for use in a method of treating an inflammatory disease or condition. The method comprises administering to a subject in need thereof a therapeutically effective amount of said compound. In certain embodiments, the inflammatory disease or condition is selected from the group consisting of inflammatory bowel disease, cartilage inflammation, bone degradation, ulcerative colitis, psoriasis, arthritis, psoriatic arthritis, rheumatoid arthritis, juvenile arthritis, juvenile rheumatoid arthritis, autoimmune hepatitis, Crohn's disease, lupus erythematosus, multiple sclerosis, Alzheimer's disease, dermatitis, atopic dermatitis, acne, Type I diabetes mellitus, Raynaud's phenomenon, Graves' disease, and Addison's disease. In certain embodiments, the inflammatory disease or condition is selected from the group consisting of Crohn's disease, ulcerative colitis, collagenous colitis, lymphocytic colitis, diversion colitis, Behçet's disease, idiopathic inflammatory bowel disease, irritable bowel syndrome, regional enteritis, spastic colon, microscopic colitis, Crohn's colitis, perianal disease, indeterminate colitis, lymphocytic gastritis, and eosinophilic enteritis. In certain embodiments, the inflammatory disease or condition is Crohn's disease. In certain embodiments, the Crohn's disease is selected from the group consisting of ileocolitis, ileitis, gastroduodenal Crohn's disease, jejunoileitis, and granulomatous ileocolitis. In certain embodiments, the Crohn's disease includes intestinal fibrosis. In certain embodiments, the Crohn's disease is fibrostenotic Crohn's disease.

In yet another aspect, the present invention provides the compound as described above for use in a method of preventing, treating or reducing fibrostenosis or intestinal fibrosis in a subject. The method comprises administering to a subject in need thereof a therapeutically effective amount of said compound. In certain embodiments, the fibrostenosis or intestinal fibrosis is associated with Crohn's disease.

BRIEF DESCRIPTION OF THE DRAWINGS

FIG. 1 shows a series of 1-aryl-1,2,3,4-tetrahydro-β-carboline derivatives.

FIG. 7 shows the chemical structures of various compounds evaluated for ADMET and other properties in the present disclosure.

FIG. 10 shows calculated bioavailability data for compounds of the present disclosure. All ADME data were calculated using ADME Suite v4.95.3. Human oral bioavailability (% F) Human oral bioavailability (% F) is the compound fraction that reaches systematic circulation after oral administration. In order to be bioavailable, a drug must comply with the following requirements: dissolve in the stomach or intestine under variable pH; withstand acid hydrolysis at pH<2; permeate through intestinal membrane by passive or active transport; withstand P-gp efflux in concert with metabolic enzymes in intestine; and withstand first pass metabolism in liver.

FIG. 11A and FIG. 11B show calculated aqueous solubility (log Sw) of various compounds of the present disclosure. Solubility (log Sw) of a compound in pure water at 25° C. and at various physiologically important pH values was predicted.

FIG. 12A and FIG. 12B show calculated pH dependent solubility for various compounds of the present disclosure.

FIG. 13 shows calculated human intestinal passive absorption for various compounds of the present disclosure. The human intestinal permeability was assessed through estimation of maximum intestinal passive absorption of a compound taking into account the transcellular and paracellular routes of permeability. Absorption related properties such as jejunum and Caco-2 permeabilities, and absorption rates (ka) values were also calculated using lipophilicity (log P) and ionization (pKa) constants.

FIG. 14 shows calculated active transport across the intestinal barrier for various compounds of the present disclosure. The calculated transport included estimation of PepT1 (oligopeptide transporter) and ASBT (bile acid transporter) substrate prediction.

FIG. 15 shows calculated P-glycoprotein specificity for various compounds of the present disclosure. The algorithm identifies P-gp substrates and/or inhibitors. Substrates are compounds that are transported (effluxed) by P-gp. Inhibitors are compounds that block P-gp transport of the standard substrates (calcein-AM and others).

FIG. 16 shows calculated tissue distribution of various compound of the present disclosure. The software predicts the extent of plasma protein binding to obtain the percentage of compound that circulates in free, pharmacologically active form, and calculates the apparent volume of distribution for an estimation of the distribution of compounds between plasma and body tissue.

FIG. 17 shows calculated interaction of various compounds of the present disclosure with cytochrome P450s. The software calculates how compounds will interact with the five cytochrome P450 (CYP) isoforms: 3A4, 2D6, 2C9, 2C19, and 1A2, that are responsible for the majority of metabolic reactions.

FIG. 18 shows data calculated with Tox Suite v 2.95 expressing the likelihood of genotoxicity resulting from various compounds of the present disclosure. Genotoxicity=Probability of positive Ames test. The Ames test is one of the most popular tests for assessing mutagenic properties of compounds. It is a short term bacterial reverse mutation test. This test is performed on various $S.$ $typhimurium$ and $E.$ $coli$ bacteria strains. The Ames test is used worldwide as an initial screen to determine mutagenic properties of NCEs in the drug and chemical industry.

FIG. 19 shows data expressing the calculated likelihood that various compounds of the present disclosure will inhibit hERG. Studies of hERG potassium ion channel inhibition constitute an emerging field in pharmacological safety research. Interactions of drugs with the hERG channel may lead to long QT syndrome, manifesting as characteristic 'Torsades de Pointes' arrhythmia, leading to occasional fatality caused by ventricular fibrillation. In recent years several promising drugs have been withdrawn from the market due to a number of sudden cardiac death occasions triggered by hERG channel inhibition. Thus, early identification of leads possessing potential safety issues is of extreme importance to prevent costly failures of R&D projects.

FIG. 20 shows the calculated probability of health effects for various compounds of the present disclosure. Predictions on health effects are based on long-term toxicity studies with adverse effects reported on particular organs or organ systems.

FIG. 21 shows calculated $LD_{50}$ values for various compounds of the present disclosure. $LD_{50}$ values can be viewed as an indication of the "cumulative potential" to cause various acute effects and death of animals and are the most widely used measure of the "acute systemic toxicity" of the chemical.

FIGS. 28A-28D show total collagen analysis of supernatants of Crohn's disease (CD) fibroblasts stimulated with TGF-β (1 ng/mL) (FIGS. 28A and C) or TNF-α (15 ng/mL) (FIGS. 28B and D) in the presence or absence of Ficz (FIGS. 28A and B) or CH223191 (a-AhR, final concentration 10 μM) (FIGS. 28C and D) for 48 hours. Data indicate mean+/−SD of 3 experiments. Taken together, these data show that AhR controls collagen secretion.

DETAILED DESCRIPTION

Figure 2:
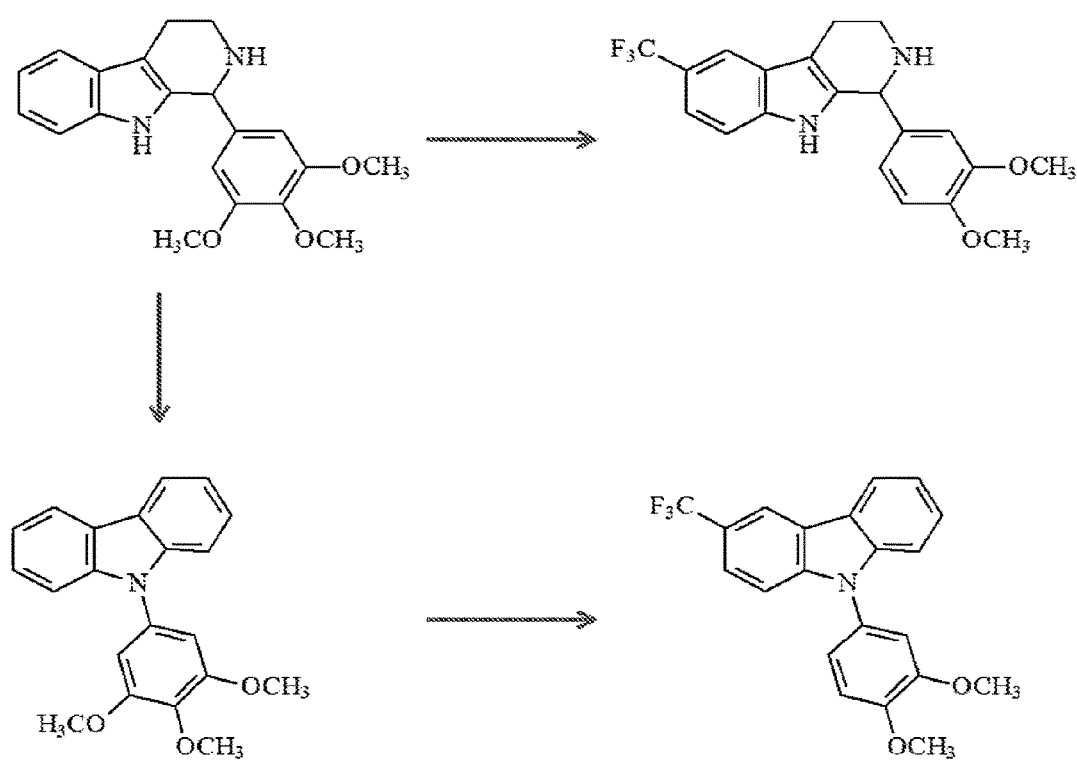
FIG. 2 shows modifications made to the 1-aryl-1,2,3,4-tetrahydro-β-carboline scaffold to study the SAR and provide improved properties.
Figure 3:
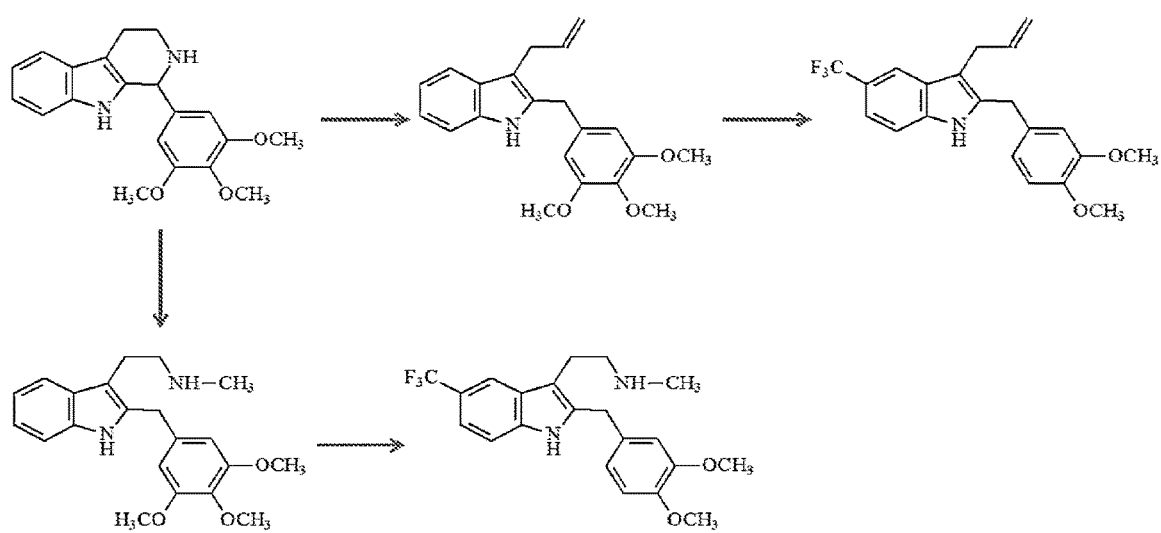
FIG. 3 shows modifications made to the 1-aryl-1,2,3,4-tetrahydro-β-carboline scaffold to study the SAR and provide improved properties.
Figure 4:
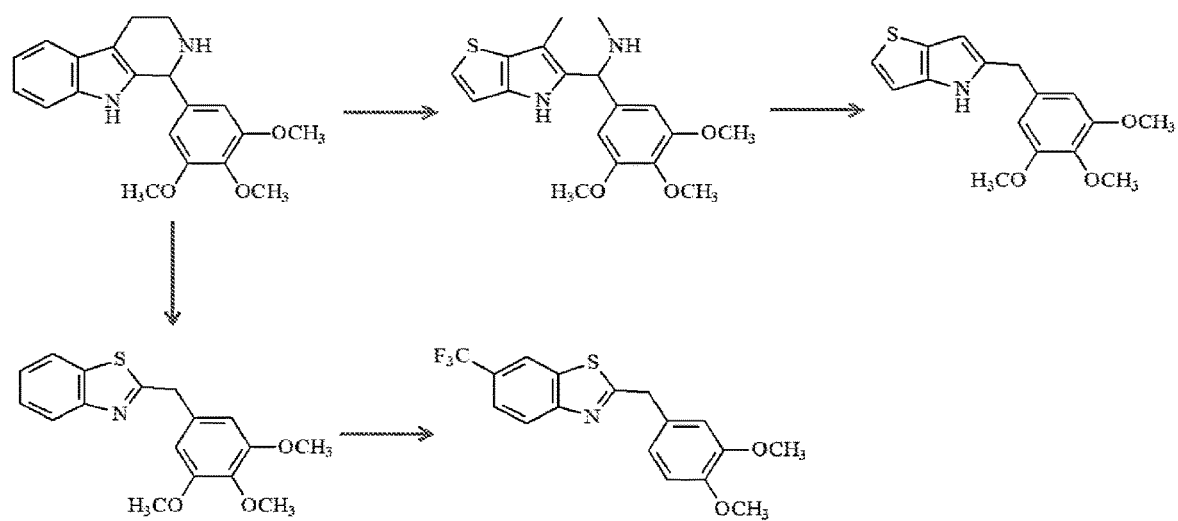
FIG. 4 shows modifications made to the 1-aryl-1,2,3,4-tetrahydro-β-carboline scaffold to study the SAR and provide improved properties.
Figure 5:
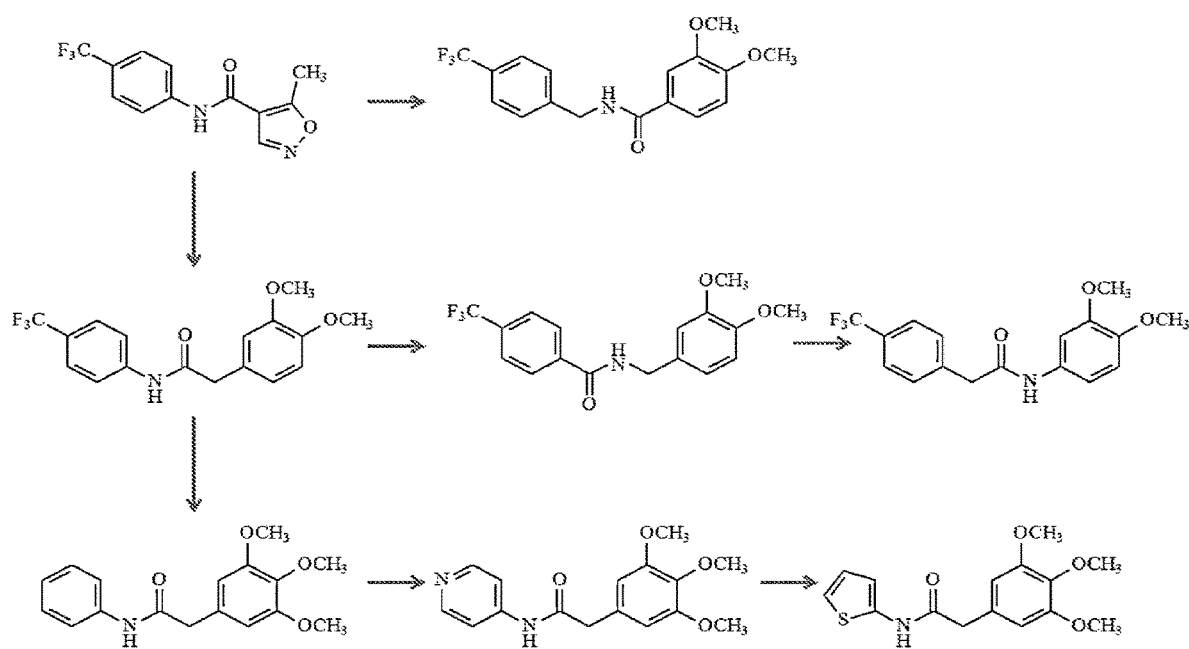
FIG. 5 shows modifications made to the Leflunomide scaffold to study the SAR and provide improved properties.
Figure 6:
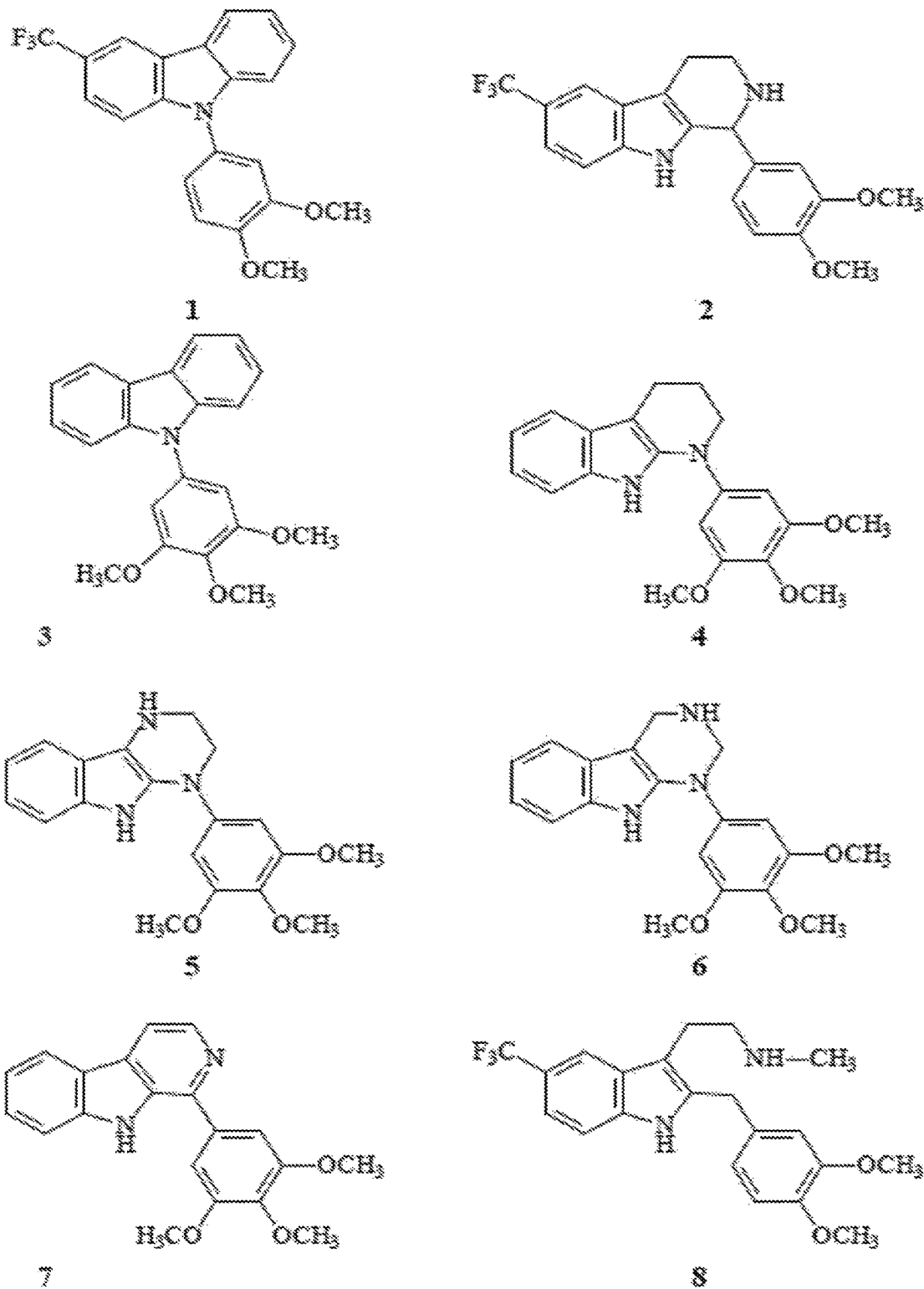
FIG. 6 shows the chemical structures of various compounds evaluated for ADMET and other properties in the present disclosure.
Figure 8:
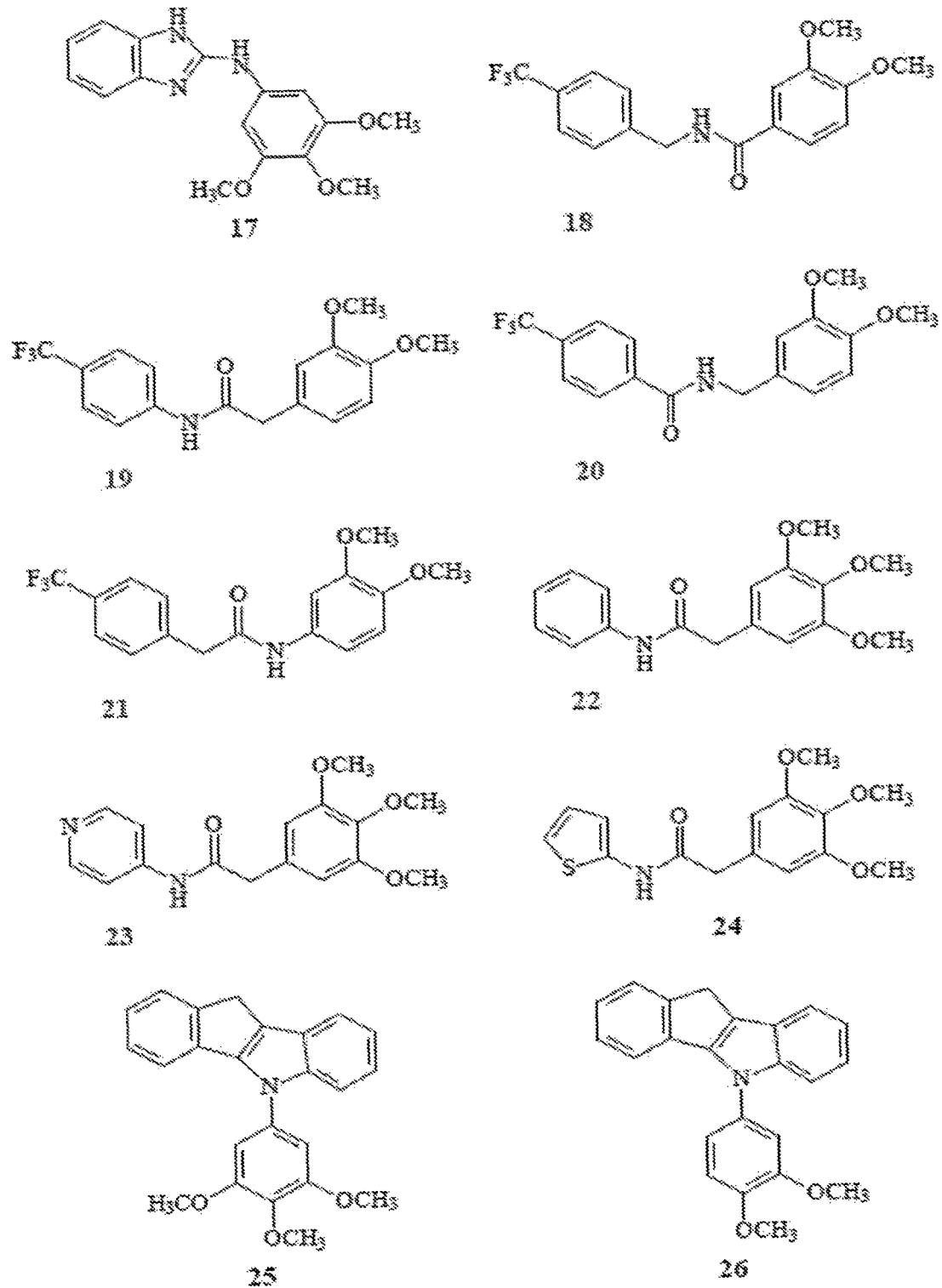
FIG. 8 shows the chemical structures of various compounds evaluated for ADMET and other properties in the present disclosure.
Figure 9:
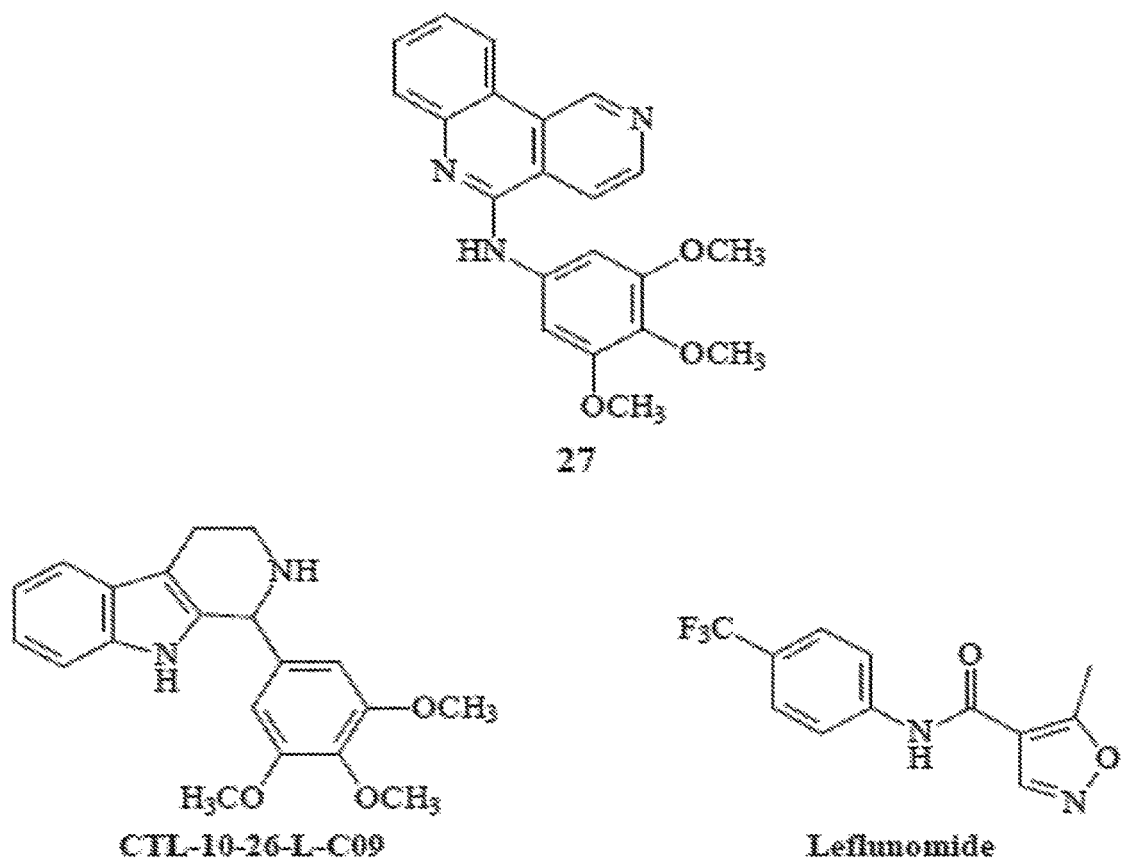
FIG. 9 shows the chemical structures of various compounds evaluated for ADMET and other properties in the present disclosure.
Figure 22:
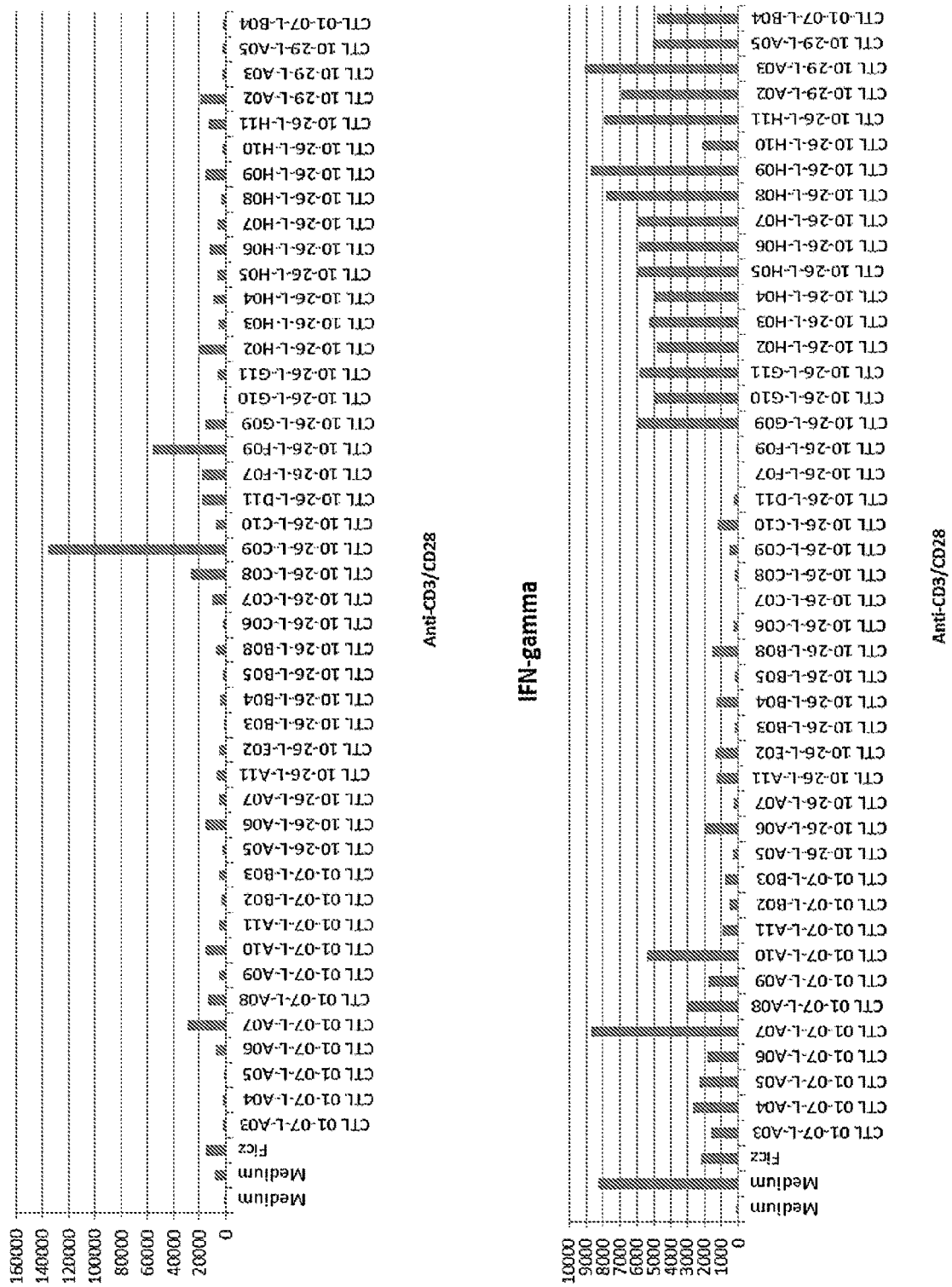
FIG. 22 shows the effects, at a final concentration of 200 nM, of various compounds of the present disclosure on IL-22 and IFN-γ levels.

In one aspect, the present disclosure provides a compound according to Formula I:

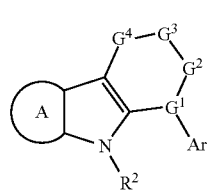

(I)

or a pharmaceutically acceptable salt thereof, wherein:
A is

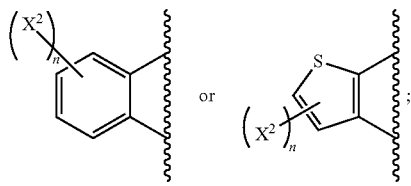

Ar is represented by

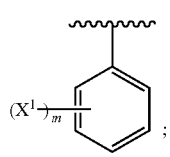

$G^1$ is $CR^4$ or N;
$G^2$, $G^3$, and $G^4$ are each independently $CR^4{}_2$ or $NR^1$;
$X^1$ is independently for each occurrence H, halogen, —OH, —CN, $C_{1-6}$ alkyl, $C_{2-6}$ alkenyl, $C_{2-6}$ alkynyl, $C_{3-6}$ cycloalkyl, $C_{1-6}$ alkoxy, —O-phenyl, —N($R^1$)$_2$, —NO$_2$, —C$_{1-6}$ alkylene-N($R^1$)$_2$, —C(O)N($R^3$)$_2$, —CO$_2R^3$, —C(O)$R^3$, —SR$^3$, —SO$_2R^3$, —SO$_3R^3$, or —SO$_2$N($R^3$)$_2$;
$X^2$ is independently for each occurrence H, halogen, —OH, —CN, $C_{1-6}$ alkyl, $C_{2-6}$ alkenyl, $C_{2-6}$ alkynyl, $C_{3-6}$ cycloalkyl, $C_{1-6}$ alkoxy, —O-phenyl, —N($R^1$)$_2$, —NO$_2$, —C$_{1-6}$ alkylene-N($R^1$)$_2$, —C(O)N($R^3$)$_2$, —CO$_2R^3$, —SR$^3$, —SO$_2R^3$, —SO$_3R^3$, or —SO$_2$N($R^3$)$_2$;
$R^1$ is independently for each occurrence H or $C_{1-6}$ alkyl;
$R^2$ is independently for each occurrence H or $C_{1-6}$ alkyl;
$R^3$ is independently for each occurrence selected from the group consisting of H, $C_{1-6}$ alkyl, phenyl, or heteroaryl;
$R^4$ is independently for each occurrence selected from the group consisting of H, $C_{1-6}$ alkyl, and halogen;
n is independently for each occurrence 0, 1, 2, or 3; and m is independently for each occurrence 0, 1, 2, 3, or 4;
wherein each instance of $C_{1-6}$ alkyl, $C_{2-6}$ alkenyl, $C_{2-6}$ alkynyl, $C_{3-6}$ cycloalkyl, $C_{1-6}$ alkoxy, or —O-phenyl may be optionally substituted with 1, 2, or 3 substituents each independently selected from the group consisting of halogen, —OH, —CN, —NR'R"—C(O)N(R'R"), and —C(O)R' (wherein R' and R" are each independently selected from H, methyl, ethyl, propyl or butyl, or R' and R" taken together form a 4-6 membered heterocycle);
wherein when A is

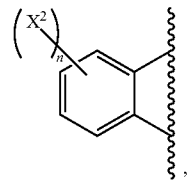

$G^1$ is CH, $G^3$, and $G^4$ are CH$_2$, and $G^2$ is NR$^1$, $X^2$ is not H (i.e., is not present, n is 0).
In certain embodiments, $G^1$ is N.
In certain embodiments, $G^2$ is NH.
In certain embodiments, $G^1$ is CH, $G^2$ is NH, and $G^3$ and $G^4$ are CH$_2$.
In certain embodiments, $G^1$ is N and $G^2$, $G^3$, and $G^4$ are CH$_2$.
In certain embodiments, $G^1$ is N, $G^2$ and $G^3$ are CH$_2$, and $G^4$ is NH.
In certain embodiments, $G^1$ is N, $G^2$ and $G^4$ are CH$_2$, and $G^3$ is NH.
In certain embodiments, $G^1$ is CH, $G^2$ and $G^4$ are NH, and $G^3$ is CH$_2$.
In certain embodiments, Ar is

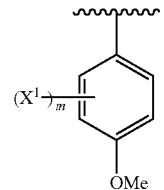

and m is 1 or 2.
In certain embodiments, Ar is

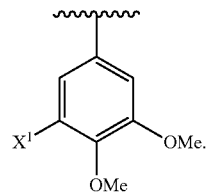

In certain embodiments, $X^1$ is H, halogen, —CN, or —OMe.
In certain embodiments, $X^1$ is —OMe.
In certain embodiments, $X^2$ is selected from the group consisting of H, halogen, —OH, —CN, $C_{1-6}$ alkoxy, and CF$_3$.
In certain embodiments, $X^2$ is CF$_3$ and n is 1.
In certain embodiments, the compound is selected from the group consisting of

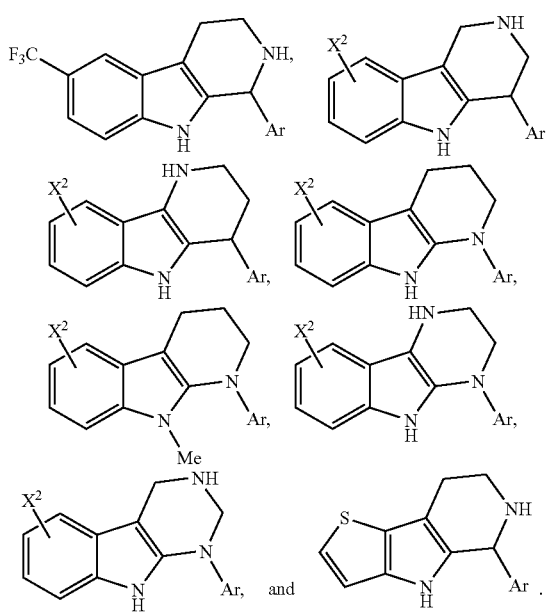

In one aspect, the present disclosure relates to a compound according to Formula I-A:

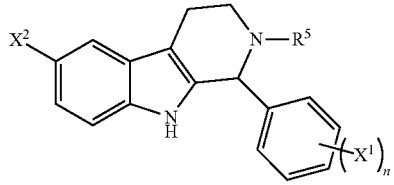

(I-A)

or a pharmaceutically acceptable salt thereof, wherein:
$X^1$ is if present independently for each occurrence $C_{1-6}$ alkyl, $C_{1-6}$ alkoxy, —O—$C_{1-6}$ alkylene-phenyl, $C_{1-6}$ acyl, —$CO_2R^3$, —$NO_2$, —OH, or —$N(R^1)_2$; or two instances of $X^1$ taken together may be —$O(CH_2)_2O$—;
$X^2$ is selected from the group consisting of H, $C_{1-6}$ alkyl, $C_{1-6}$ alkoxy, —O—$C_{1-6}$ alkylene-phenyl, and —OH;
$R^1$ is independently for each occurrence H or $C_{1-6}$ alkyl;
$R^3$ is independently for each occurrence H, $C_{1-6}$ alkyl, phenyl, or heteroaryl;
$R^5$ is selected from the group consisting of H, $C_{1-6}$ alkyl, $C_{1-6}$ acyl, and —$CO_2R^3$; and
n is 0, 1, 2, or 3;
wherein each instance of $C_{1-6}$ alkyl, $C_{2-6}$ alkenyl, $C_{2-6}$ alkynyl, $C_{3-6}$ cycloalkyl, $C_{1-6}$ alkoxy, or —O-phenyl may be optionally substituted with 1, 2, or 3 substituents each independently selected from the group consisting of halogen, —OH, —CN, —NR'R"—C(O)N(R'R"), and —C(O)R' (wherein R' and R" are each independently selected from H, methyl, ethyl, propyl or butyl, or R' and R" taken together form a 4-6 membered heterocycle).

In certain embodiments, $X^2$ is selected from the group consisting of H, —OMe, ethyl, —OH, and —$OCH_2Ph$.

In certain embodiments, $R^5$ is selected from the group consisting of H, acetyl, propyl, isopropyl, butyl, isobutyl, tert-butyl, pentyl, isopentyl, and —$CO_2CH_2Ph$.

In certain embodiments, $X^1$ is independently for each occurrence H, —OMe, —$NO_2$, —$CO_2Me$, methyl, —OC(O)Me, —$OCH_2Ph$, —OH, —$NH_2$, or tert-butyl; or two instances of $X^1$ taken together may be —$O(CH_2)_2O$—.

In certain embodiments, n is 3.

In one aspect, the present disclosure relates to a compound according to Formula II:

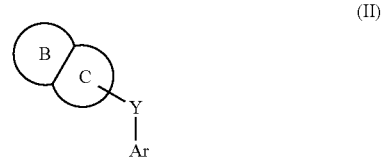

(II)

or a pharmaceutically acceptable salt thereof, wherein:
B is

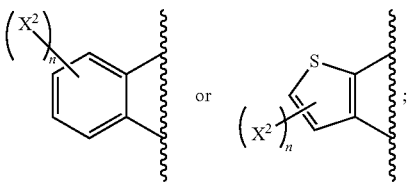

C is

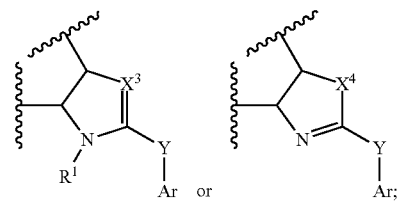

Ar is represented by

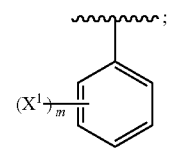

$X^1$ is independently for each occurrence, if present, selected from halogen, —OH, —CN, $C_{1-6}$ alkyl, $C_{2-6}$ alkenyl, $C_{2-6}$ alkynyl, $C_{3-6}$ cycloalkyl, $C_{1-6}$ alkoxy, —O-phenyl, —$N(R^1)_2$, —$NO_2$, —$C_{1-6}$ alkylene-$N(R^1)_2$, —$C(O)N(R^3)_2$, —$CO_2R^3$, —$C(O)R^3$, —$SR^3$, —$SO_2R^3$, —$SO_3R^3$, or —$SO_2N(R^3)_2$;

$X^2$ is independently for each occurrence if present, selected from, halogen, —OH, —CN, $C_{1-6}$ alkyl, $C_{2-6}$ alkenyl, $C_{2-6}$ alkynyl, $C_{3-6}$ cycloalkyl, $C_{1-6}$ alkoxy, —O-phenyl, —$N(R^1)_2$, —$NO_2$, —$C_{1-6}$ alkylene-$N(R^1)_2$, —$C(O)N(R^3)_2$, —$CO_2R^3$, —$SR^3$, —$SO_2R^3$, —$SO_3R^3$, or —$SO_2N(R^3)_2$;

$R^1$ is independently for each occurrence H or $C_{1-6}$ alkyl;

$R^3$ is independently for each occurrence H, $C_{1-6}$ alkyl, phenyl, or heteroaryl;

$R^4$ is selected from the group consisting of H, $C_{1-6}$ alkyl, $C_{2-6}$ alkenyl, $C_{2-6}$ alkynyl, —$N(R^1)_2$, —$C_{1-6}$ alkylene-$N(R^1)_2$, —$C(O)N(R^3)_2$, and —$CO_2R^3$;

n is independently for each occurrence 0, 1, 2, or 3;

m is independently for each occurrence 0, 1, 2, 3, or 4;

wherein each instance of $C_{1-6}$ alkyl, $C_{2-6}$ alkenyl, $C_{2-6}$ alkynyl, $C_{3-6}$ cycloalkyl, $C_{1-6}$ alkoxy, or —O-phenyl may be optionally substituted with 1, 2, or 3 substituents each independently selected from the group consisting of halogen, —OH, —CN, —NR'R"—C(O)N(R'R"), and —C(O)R' (wherein R' and R" are each independently selected from H, methyl, ethyl, propyl or butyl, or R' and R" taken together form a 4-6 membered heterocycle);

$X^3$ is N or $CR^4$;

$X^4$ is $NR^1$, O, or S; and

Y is a bond, $C_{1-6}$ alkylene or —N($R^1$)—;

wherein when B is

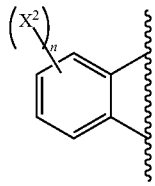

and $X^4$ is S, $X^2$ is not H (i.e., is not present).

In certain embodiments of Formula II Y is $CH_2$ or NH.

In certain embodiments, $R^4$ is selected from the group consisting of $C_{2-6}$ alkenyl, $C_{2-6}$ alkynyl, —$C_{1-6}$ alkylene-N($R^1$)$_2$, and —C(O)N($R^3$)$_2$.

In certain embodiments, $R^4$ is allyl or

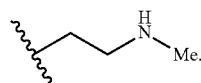

In certain embodiments, Ar is

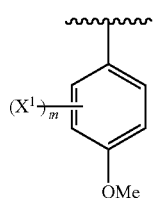

and m is 1 or 2.

In certain embodiments, Ar is

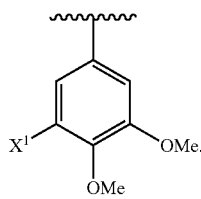

In certain embodiments, $X^1$ is H (i.e., n is 0), halogen, —CN, or —OMe.

In certain embodiments, A, B and L taken together are compounds represented by:

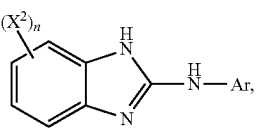

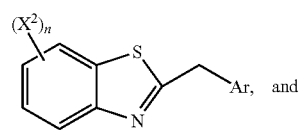

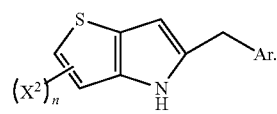

In certain embodiments, $X^2$ is selected from the group consisting of H, halogen, —OH, —CN, $C_{1-6}$ alkoxy, and $CF_3$.

In certain embodiments, $X^2$ is $CF_3$ and n is 1.

In one aspect, the present disclosure relates to a compound according to Formula III:

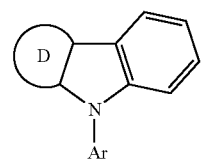

or a pharmaceutically acceptable salt thereof, wherein:

D is

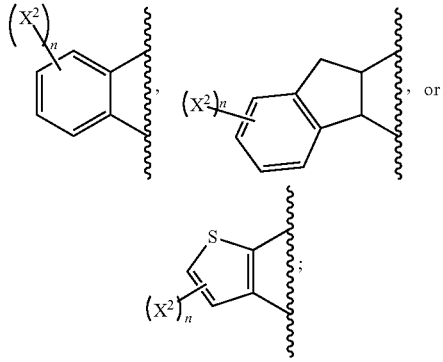

Ar is represented by

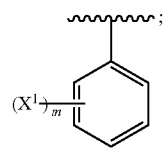

$X^1$ may be present, and may be selected independently for each occurrence from, halogen, —OH, —CN, $C_{1-6}$ alkyl, $C_{2-6}$ alkenyl, $C_{2-6}$ alkynyl, $C_{3-6}$ cycloalkyl, $C_{1-6}$ alkoxy, —O-phenyl, —N(R¹)₂, —NO₂, —C₁₋₆ alkylene-N(R¹)₂, —C(O)N(R³)₂, —CO₂R³, —C(O)R³, —SR³, —SO₂R³, —SO₃R³, or —SO₂N(R³)₂;

X² may be present, and may be selected independently for each occurrence from, halogen, —OH, —CN, C₁₋₆ alkyl, C₂₋₆ alkenyl, C₂₋₆ alkynyl, C₃₋₆ cycloalkyl, C₁₋₆ alkoxy, —O-phenyl, —N(R¹)₂, —NO₂, —C₁₋₆ alkylene-N(R¹)₂, —C(O)N(R³)₂, —CO₂R³, —SR³, —SO₂R³, —SO₃R³, or —SO₂N(R³)₂;

R¹ is independently for each occurrence H or C₁₋₆ alkyl;

R³ is independently for each occurrence H, C₁₋₆ alkyl, phenyl, or heteroaryl;

n is independently for each occurrence 0, 1, 2, or 3; and m is independently for each occurrence 0, 1, 2, 3, or 4;

wherein each instance of C₁₋₆ alkyl, C₂₋₆ alkenyl, C₂₋₆ alkynyl, C₃₋₆ cycloalkyl, C₁₋₆ alkoxy, or —O-phenyl may be optionally substituted with 1, 2, or 3 substituents each independently selected from the group consisting of halogen, —OH, —CN, —NR'R"—C(O)N(R'R"), and —C(O)R' (wherein R' and R" are each independently selected from H, methyl, ethyl, propyl or butyl, or R' and R" taken together form a 4-6 membered heterocycle);

wherein when D is

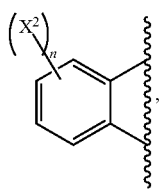

X² is not H (i.e., X² is not present and n is 0).

In certain embodiments, Ar is

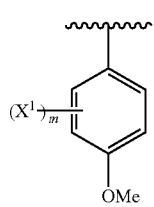

and m is 1 or 2.

In certain embodiments, Ar is

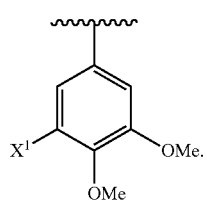

In certain embodiments, X¹ is H, halogen, —CN, or —OMe.

In certain embodiments, X¹ is —OMe.

In certain embodiments, X² is selected from the group consisting of H, halogen, —OH, —CN, C₁₋₆ alkoxy, and CF₃.

In certain embodiments, X² is CF₃ and n is 1.

In one aspect, the present disclosure relates to a compound according to Formula IV:

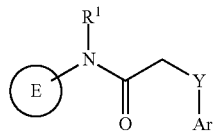

or a pharmaceutically acceptable salt thereof, wherein:

E is a ring selected from the group consisting of heterocyclyl, 5-membered heteroaromatic, 6-membered heteroaromatic, aromatic, and C₃₋₆ cycloalkyl, wherein the ring is optionally substituted with 1, 2, or 3 X²;

Ar is represented by

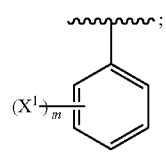

X¹ is if present, selected independently for each occurrence from the group consisting of H, halogen, —OH, —CN, C₁₋₆ alkyl, C₂₋₆ alkenyl, C₂₋₆ alkynyl, C₃₋₆ cycloalkyl, C₁₋₆ alkoxy, —O-phenyl, —N(R¹)₂, —NO₂, —C₁₋₆ alkylene-N(R¹)₂, —C(O)N(R³)₂, —CO₂R³, —C(O)R³, —SR³, —SO₂R³, —SO₃R³, or —SO₂N(R³)₂;

X² is independently for each occurrence selected from the group consisting of halogen, —OH, —CN, C₁₋₆ alkyl, C₂₋₆ alkenyl, C₂₋₆ alkynyl, C₃₋₆ cycloalkyl, C₁₋₆ alkoxy, —O-phenyl, —N(R¹)₂, —NO₂, —C₁₋₆ alkylene-N(R¹)₂, —C(O)N(R³)₂, —CO₂R³, —SR³, —SO₂R³, —SO₃R³, or —SO₂N(R³)₂; Y is selected from the group consisting of a bond, NR' or C₁₋₆alkylene (e.g., a bond or C₁₋₂alkylene);

R¹ is independently for each occurrence H or C₁₋₆ alkyl;

R³ is independently for each occurrence selected from the group consisting of H, C₁₋₆ alkyl, phenyl, or heteroaryl; and m is independently for each occurrence 0, 1, 2, 3, or 4;

wherein each instance of C₁₋₆ alkyl, C₂₋₆ alkenyl, C₂₋₆ alkynyl, C₃₋₆ cycloalkyl, C₁₋₆ alkoxy, or —O-phenyl may be optionally substituted with 1, 2, or 3 substituents each independently selected from the group consisting of halogen, —OH, —CN, —NR'R"—C(O)N(R'R"), and —C(O)R' (wherein R' and R" are each independently selected from H, methyl, ethyl, propyl or butyl, or R' and R" taken together form a 4-6 membered heterocycle).

In certain embodiments, of Formula IV, Y is a bond, CH₂ or NH; (for example Y may be a bond).

In certain embodiments, Ar is

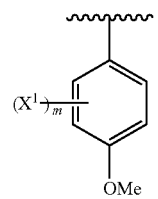

and m is 1 or 2.

In certain embodiments, Ar is

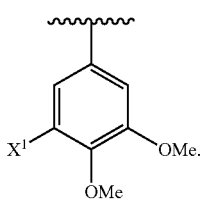

In certain embodiments, $X^1$ is H, halogen, —CN, or —OMe.

In certain embodiments, $X^1$ is —OMe.

In certain embodiments, $X^2$ is selected from the group consisting of H, halogen, —OH, —CN, $C_{1-6}$ alkoxy, and $CF_3$.

In certain embodiments, $X^2$ is $CF_3$.

In one aspect, the present disclosure relates to a pharmaceutical composition, comprising a compound described above; and a pharmaceutically acceptable carrier.

Definitions

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautonerisn.

The term "alkyl" refers to a monovalent saturated aliphatic group with a carbon atom as the point of attachment, a linear or branched, cyclic or acyclic structure, and no atoms other than carbon and hydrogen. Thus, as used herein cycloalkyl is a subset of alkyl. The groups —$CH_3$ (Me), —$CH_2CH_3$ (Et), —$CH_2CH_2CH_3$ (n-Pr), —$CH(CH_3)_2$ (i-Pr), —$CH(CH_2)_2$ (cyclopropyl), —$CH_2CH_2CH_2CH_3$ (n-Bu), —$CH(CH_3)CH_2CH_3$ (sec-butyl), —$CH_2CH(CH_3)_2$ (iso-butyl), —$C(CH_3)_3$ (tert-butyl), —$CH_2C(CH_3)_3$ (neopentyl), cyclobutyl, cyclopentyl, cyclohexyl, and cyclohexylmethyl are non-limiting examples of alkyl groups. The term "alkylene" refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2CH_2$—, —$CH_2CH_2CH_2$—, and

are non-limiting examples of alkylene groups.

The term "alkenyl" refers to a monovalent unsaturated aliphatic group with a carbon atom as the point of attachment, a linear or branched, cyclic or acyclic structure, at least one nonaromatic carbon-carbon double bond, no carbon-carbon triple bonds, and no atoms other than carbon and hydrogen. Non-limiting examples of alkenyl groups include: —CH=$CH_2$ (vinyl), —CH=$CHCH_3$, —CH=$CHCH_2CH_3$, —$CH_2$CH=$CH_2$ (allyl), —$CH_2$CH=$CHCH_3$, and —CH=CH—$C_6H_5$.

The term "alkynyl" refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡$CCH_3$, and —$CH_2$C≡$CCH_3$, are non-limiting examples of alkynyl groups.

The term "aryl" refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, –$C_6H_4$—$CH_2CH_3$ (ethylphenyl), —$C_6H_4$—$CH_2CH_2CH_3$ (propylphenyl), —$C_6H_4$—$CH(CH_3)_2$, —$C_6H_4$—$CH(CH_2)_2$, —$C_6H_3(CH_3)CH_2CH_3$ (methylethylphenyl), —$C_6H_4$—CH=$CH_2$ (vinylphenyl), —$C_6H_4$—CH=$CHCH_3$, —$C_6H_4$C≡CH, —$C_6H_4$C≡$CCH_3$, naphthyl, and the monovalent group derived from biphenyl.

The term "heteroaryl" refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl.

The term "heterocyclyl" refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocyclyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocyclyl groups include aziridinyl, pyrrolidinyl, piperidinyl, piperazinyl, morpholinyl, thiomorpholinyl, tetrahydrofuranyl, tetrahydrothiofuranyl, tetrahydropyranyl, and pyranyl.

The term "acyl" refers to the group —C(O)R, in which R is a hydrogen, alkyl, aryl, aralkyl or heteroaryl, as those terms are defined above. The groups —CHO, —C(O)$CH_3$ (acetyl, Ac), —C(O)$CH_2CH_3$, C(O)$CH_2CH_3$, —C(O)CH$(C_3)_2$, —C(O)CH$(CH_2)_2$, —C(O)$C_6H_5$, —C(O)$C_6H_4$—$CH_3$, —C(O)$CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom.

The term "alkoxy" refers to the group —OR, in which R is an alkyl, as that term is defined above. Non-limiting examples of alkoxy groups include: —$OCH_3$, —$OCH_2CH_3$, —OCH₂CH₂CH₃, —OCH(CH₃)₂, —OCH(CH₂)₂, —O-cyclopentyl, and —O-cyclohexyl.

The definition of "pharmaceutically acceptable" is meant to encompass any carrier, salt form, or other agent, which does not interfere with effectiveness of the biological activity of the active ingredient and that is not toxic to the host to which it is administered. As used herein, "pharmaceutically acceptable carrier" means buffers, carriers, diluents, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. "Pharmaceutically acceptable salts" means salts of compounds of the present disclosure which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties, and Use* (P. H. Stahl & C. G. Wermuth eds., Verlag Helvetica Chimica Acta, 2002), which is incorporated herein by reference.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

A "patient" or "subject" as described herein, refers to any animal at risk for, suffering from or diagnosed for an inflammatory condition, including, but not limited to, mammals, primates, and humans. In certain embodiments, the patient may be a non-human mammal such as, for example, a cat, a dog, or a horse. A patient may be an individual diagnosed with a high risk of developing an inflammatory condition, someone who has been diagnosed with an inflammatory condition, someone who previously suffered from an inflammatory condition, or an individual evaluated for symptoms or indications of an inflammatory condition.

"A patient in need", as used herein, refers to a patient suffering from any of the symptoms or manifestations of an inflammatory condition, e.g., inflammatory bowel disease, a patient who may suffer from any of the symptoms or manifestations of an inflammatory condition, or any patient who might benefit from a method of the invention for treating an inflammatory condition. A patient in need may include a patient who is diagnosed with a risk of developing an inflammatory condition such as inflammatory bowel disease, a patient who has suffered from an inflammatory condition, or a patient who has previously been treated for such a condition.

The terms "treat", "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. preventing the disease from increasing in severity or scope; (c) relieving the disease, i.e. causing partial or complete amelioration of the disease; or (d) preventing relapse of the disease, i.e. preventing the disease from returning to an active state following previous successful treatment of symptoms of the disease or treatment of the disease.

"Effective amount," as used herein, refers to the amount of an agent that is sufficient to at least partially treat a condition when administered to a patient. The therapeutically effective amount will vary depending on the severity of the condition, the route of administration of the component, and the age, weight, etc. of the patient being treated. Accordingly, an effective amount of a compound of the present disclosure is the amount of such a compound necessary to treat one or more conditions or diseases contemplated herein in a patient such that administration of the agent prevents the condition(s) from occurring in a subject, prevents progression of the condition (e.g., prevents the onset or increased severity of symptoms of the condition), or relieves or completely ameliorates all associated symptoms of the condition, i.e. causes regression of the condition. An effective amount may also be the amount of such a compound necessary to bring about a desired biological effect, e.g. decreasing INF-γ levels.

Efficacy of treatment may be evaluated by means of evaluation of gross symptoms associated with the inflammatory condition, analysis of tissue histology, biochemical assay, imaging methods such as, for example, magnetic resonance imaging, or other known methods. For instance, efficacy of treatment may be evaluated by analyzing gross symptoms of the condition such as changes in tissue inflammation, abdominal pain, vomiting, diarrhea, rectal bleeding, cramps, muscle spasms, weight loss, malnutrition, fever, anemia or other aspects of gross pathology associated with an inflammatory condition following administration of a compound described herein.

Efficacy of treatment may also be evaluated at the tissue or cellular level, for example, by means of obtaining a tissue biopsy (e.g., a gastrointestinal tissue biopsy) and evaluating gross tissue or cell morphology or staining properties. Biochemical assays that examine protein or RNA expression may also be used to evaluate efficacy of treatment. For instance, one may evaluate IL-22, IFN-γ, or levels of another protein or gene product indicative of one or more inflammatory condition(s), inflammatory cytokine production, or an IL-22 mediated inflammatory response in dissociated cells or non-dissociated tissue via immunocytochemical, immunohistochemical, Western blotting, or Northern blotting methods, or methods useful for evaluating RNA levels such as quantitative or semi-quantitative polymerase chain reaction. One may also evaluate the presence or level of expression of useful biomarkers found in fecal matter, plasma, or serum to evaluate disease state and efficacy of treatment.

Methods

The present disclosure provides a method of treating an inflammatory condition in a patient in need thereof, comprising administering an effective amount of a compound disclosed herein to the patient. Exemplary inflammatory conditions contemplated herein include Crohn's disease, gastroduodenal Crohn's disease, Crohn's (granulomatous) colitis, ulcerative colitis, collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, indeterminate colitis and eosinophilic enteritis. Other contemplated inflammatory conditions include cartilage inflammation, bone degradation, rheumatoid arthritis, arthritis, psoriatic arthritis, hypersensitivity pneumonitis, liver diseases such as fatty liver, hepatitis, hepatic steatosis, and nonalcoholic steatohepatitis (NASH), fibrosis (e.g., intestinal fibrosis, lung fibrosis, or liver fibrosis), autoimmune polyendocrine syndrome, Addison's disease, Goodpasture's syndrome, Graves' disease, Guillain-Barré syndrome, Hashimoto's encephalopathy, psoriasis, Hashimoto's thyroiditis, juvenile arthritis (e.g., juvenile idiopathic arthritis), lupus erythematous, multiple sclerosis, Alzheimer's disease, dermatitis, atopic dermatitis, acne, Type I diabetes mellitus, autoimmune hepatitis, Ménière's disease, Raynaud's phenomenon, Sjögren's syndrome, ankylosing spondylitis, chronic fatigue syndrome, rheumatic polymyalgia, osteoarthritis, prostatitis, and Reiter syndrome. In certain embodiments the patient is a mammal. In certain other embodiments the patient is a human.

In certain embodiments, a method of treating an inflammatory disease or condition is provided, wherein the disease or condition is selected from the group consisting of inflammatory bowel disease, cartilage inflammation, bone degradation, ulcerative colitis, psoriasis, arthritis, psoriatic arthritis, rheumatoid arthritis, juvenile arthritis, juvenile rheumatoid arthritis, autoimmune hepatitis, Crohn's disease, lupus erythematosus, multiple sclerosis, Alzheimer's disease, dermatitis, atopic dermatitis, acne, Type I diabetes mellitus, Raynaud's phenomenon, Graves' disease, and Addison's disease, and wherein the method comprises administering to a patient in need thereof an effective amount of a disclosed compound. In certain embodiments the patient is a mammal. In certain other embodiments the patient is a human.

A method of treating Crohn's disease is provided, and/or ulcerative colitis, and/or inflammatory bowel disease, comprising administering to a patient in need thereof an effective amount of a disclosed compound. In certain embodiments the patient is a mammal. In certain other embodiments the patient is a human.

In certain embodiments, the inflammatory disease or condition is selected from the group consisting of Crohn's disease, ulcerative colitis, collagenous colitis, lymphocytic colitis, diversion colitis, Behçet's disease, idiopathic inflammatory bowel disease, irritable bowel syndrome, regional enteritis, spastic colon, microscopic colitis, Crohn's colitis, perianal disease, and indeterminate colitis.

In certain embodiments, the inflammatory disease or condition is Crohn's disease. In certain embodiments, the Crohn's disease is selected from the group consisting of ileocolitis, ileitis, gastroduodenal Crohn's disease, jejunoileitis, and granulomatous ileocolitis. In certain embodiments, the Crohn's disease includes intestinal fibrosis. In certain embodiments, the Crohn's disease is fibrostenotic Crohn's disease.

In another aspect, the present disclosure provides a method of preventing, treating, or reducing fibrostenosis or intestinal fibrosis in a subject, comprising administering to a subject in need thereof a therapeutically effective amount of a compound disclosed herein. In certain embodiments, the fibrostenosis or intestinal fibrosis is associated with Crohn's disease.

It may be appreciated that inflammatory bowel disease may be associated with a number of symptoms. Accordingly, the present disclosure provides a method of relieving one or more symptoms of inflammatory bowel disease selected from the group consisting of abdominal pain, vomiting, diarrhea, rectal bleeding, severe cramps, muscle spasms, weight loss, malnutrition, fever, anemia, skin lesions, joint pain, eye inflammation, liver disorders, arthritis, pyoderma gangrenosum, primary sclerosing cholangitis, non-thyroidal illness syndrome, and growth defects in children, comprising administering to a patient in need thereof an effective amount of a disclosed compound.

In one aspect, the present disclosure relates to a method of decreasing IFN-γ levels and/or inhibiting IFN-γ, comprising administering to a subject in need thereof a therapeutically effective amount of a disclosed compound. "Inhibiting IFN-γ," as used herein, may refer to a complete or partial reduction in IFN-γ expression or activity. Thus, inhibiting IFN-γ may refer to alterations in IFN-γ gene or chromatin state or altered interaction with regulators of gene transcription or gene accessibility that results in a complete or partial reduction in expression of IFN-γ gene products, e.g., IFN-γ RNA, IFN-γ protein, or peptide sequences of IFN-γ. Inhibiting IFN-γ may also refer to inhibition of processes crucial to IFN-γ gene product expression, including, but not limited to IFN-γ transcription, IFN-γ RNA processing, IFN-γ protein translation, or IFN-γ post-translational modification. Additionally, inhibiting IFN-γ may refer to inhibiting activity of IFN-γ gene products, including peptides of IFN-γ, nucleotide products of IFN-γ (e.g., IFN-γ mRNA), and IFN-γ protein. Inhibiting activity of IFN-γ gene products may include a reduction in IFN-γ signaling or direct or indirect interaction of IFN-γ with other cellular components (e.g., proteins, peptides, DNA, RNA, lipids, or signaling molecules) including nuclear, organelle, cytosolic, membrane, and extracellular components. For example, inhibiting IFN-γ activity may include inhibiting IFN-γ binding or activation of CSF1R or inhibiting CSF1R downstream signaling effects (e.g., MAP Kinase phosphorylation or macrophage proliferation).

In one aspect, the present disclosure relates to a method of increasing IL-22 levels, comprising administering to a subject in need thereof a therapeutically effective amount of a disclosed compound. Such increase may be for improving or strengthening immunity or to provide an immunoprotective function.

The invention also provides methods of increasing IL-22 production in cells of a patient suffering from an inflammatory condition, comprising administering to a patient in need thereof an effective amount of a disclosed compound. IL-22 production may be increased in any cell in which IL-22 expression or activity occurs, including cells of the gastrointestinal tract, immune system, and blood. Cells of the gastrointestinal tract (including cells of the stomach, duodenum, jejunum, ileum, colon, rectum and anal canal), include columnar epithelial cells, mucosal epithelial cells, zymogenic cells, neck mucus cells, parietal cells, gastrin cells, goblet cells, paneth cells, oligomucus cells, and villus absorptive cells. Cells of the immune system include leukocytes, phagocytes (e.g., macrophages, neutrophils, and dendritic cells), monocytes, mast cells, eosinophils, basophils, natural killer cells, innate cells, lymphocytes, B cells, and T cells. Blood cells include red blood cells (erythrocytes) and white blood cells (leukocytes, monocytes, and platelets).

In one aspect, the present disclosure relates to a method of increasing IL-22 levels and decreasing IFN-γ levels, comprising administering to a subject in need thereof a therapeutically effective amount of a compound described above.

In one aspect, the present disclosure relates to a method of inhibiting lipid peroxidation, comprising administering to a subject in need thereof a therapeutically effective amount of a compound described above.

In one aspect, the present disclosure relates to a method of modulating an aryl hydrocarbon receptor (AhR), comprising administering a selective AhR modulator; wherein said selective AhR modulator is a compound described above.

In another aspect, the present invention provides a compound as described herein for use as a medicament. In another aspect, the present invention provides a compound as described herein for use in a method of treating an inflammatory disease or condition. The inflammatory disease or condition may be as defined above. In yet another aspect, the present invention provides a compound as described herein for use in a method of treating Crohn's disease and/or ulcerative colitis, and/or inflammatory bowel disease. The Crohn's disease may be as defined above. In another aspect, the present disclosure provides a compound as described herein for use in a method of preventing, treating, or reducing fibrostenosis or intestinal fibrosis. In certain embodiments, the fibrostenosis or intestinal fibrosis is associated with Crohn's disease. In another embodiment, the present invention provides a compound as described herein for use in a method of relieving one or more symptoms of inflammatory bowel disease. The symptoms may be as defined above. In one aspect, the present invention provides a compound as described herein relates to a method of decreasing IFN-γ levels and/or inhibiting IFN-γ in a subject in need thereof. Inhibiting IFN-γ may be as defined above. In a further aspect, the present provides a compound as described herein for use in a method of increasing IL-22 levels in a subject. Such increase may be for improving or strengthening immunity or to provide an immunoprotective function. The invention also provides a compound as described above for use in a method of increasing IL-22 production in cells of a patient suffering from an inflammatory condition. The inflammatory condition may be as defined above. In another aspect, the present invention provides a compound as described herein for use in a method of increasing IL-22 levels and decreasing IFN-γ levels in a subject. The present invention also provides a compound as described herein for use in a method of inhibiting lipid peroxidation in a subject. The present invention also provides a compound for use in a method of modulating an aryl hydrocarbon receptor (AhR) in a subject.

Pharmaceutical Compositions and Routes of Administration

The present invention also provides pharmaceutical compositions comprising a compound described herein. In another aspect, the invention provides a pharmaceutical composition for use in treating an inflammatory condition. The pharmaceutical composition may comprise a compound described herein and a pharmaceutically acceptable carrier. As used herein the term "pharmaceutical composition" means, for example, a mixture containing a specified amount of a therapeutic compound, e.g., a therapeutically effective amount, of a therapeutic compound in a pharmaceutically acceptable carrier to be administered to a mammal, e.g., a human, in order to treat an inflammatory condition.

Compounds of the present disclosure can be specially formulated for administration of the compound to a subject in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Pharmaceutical compositions containing a compound described herein can be presented in a dosage unit form and can be prepared by any suitable method. A pharmaceutical composition should be formulated to be compatible with its intended route of administration. Useful formulations can be prepared by methods well known in the pharmaceutical art. For example, see *Remington's Pharmaceutical Sciences*, 18th ed. (Mack Publishing Company, 1990).

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

The pharmaceutical compositions of the invention can be formulated for parenteral administration, e.g., formulated for injection via the intravenous, intramuscular, subcutaneous, intralesional, or intraperitoneal routes. The preparation of an aqueous composition, such as an aqueous pharmaceutical composition containing a compound described herein, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In addition, sterile, fixed oils may be employed as a solvent or suspending medium. For this purpose any bland fixed oil can be employed including synthetic mono- or diglycerides. In addition, fatty acids such as oleic acid can be used in the preparation of injectables. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In one embodiment, the compound may be suspended in a carrier fluid comprising 1% (w/v) sodium carboxymethylcellulose and 0.1% (v/v) TWEEN™ 80. Under ordinary conditions of storage and use, these preparations contain a preservative to prevent the growth of microorganisms.

Injectable preparations, for example, sterile injectable aqueous or oleaginous suspensions may be formulated according to the known art using suitable dispersing or wetting agents and suspending agents. Generally, dispersions are prepared by incorporating the various sterilized active ingredients into a sterile vehicle which contains the basic dispersion medium and the required other ingredients from those enumerated above. Sterile injectable solutions of the invention may be prepared by incorporating a compound described herein in the required amount of the appropriate solvent with various of the other ingredients enumerated above, as required, followed by filtered sterilization. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The injectable formulations can be sterilized, for example, by filtration through a bacteria-retaining filter.

The preparation of more, or highly concentrated solutions for intramuscular injection is also contemplated. In this regard, the use of DMSO as solvent is preferred as this will result in extremely rapid penetration, delivering high concentrations of the compound to a small area.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium 10 carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

In some embodiments, contemplated herein are compositions suitable for oral delivery of a compound described herein, e.g., tablets, that include an enteric coating, e.g., a gastro-resistant coating, such that the compositions may deliver the compound to, e.g., the gastrointestinal tract of a patient.

For example, a tablet for oral administration is provided that comprises granules (e.g., is at least partially formed from granules) that include a compound described herein, and one or more pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring agents such as wintergreen, orange, xylitol, sorbitol, fructose, and maltodextrin, and perfuming agents, preservatives and/or antioxidants.

In some embodiments, contemplated pharmaceutical formulations include an intra-granular phase that includes a compound described herein, or a pharmaceutically acceptable salt thereof, and a pharmaceutically acceptable filler. For example, the compound and a filler may be blended together, optionally, with other excipients, and formed into granules. In some embodiments, the intragranular phase may be formed using wet granulation, e.g. a liquid (e.g., water) is added to the blended compound and filler, and then the combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

A disclosed formulation may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pregelatinized starch, calcium carbonate, and others including combinations thereof.

In some embodiments, a disclosed formulation may include a intragranular phase and/or a extragranular phase that includes a binder, which may generally function to hold the ingredients of the pharmaceutical formulation together. Exemplary binders of the invention may include, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated formulation includes an intra-granular phase comprising a compound described herein and excipients chosen from: mannitol, microcrystalline cellulose, hydroxypropylmethyl cellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated formulation may include a lubricant, e.g. an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive tract. Enteric coatings may include a polymer that disintegrates at different rates according to pH. Enteric coatings may include for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

Exemplary enteric coatings include Opadry® AMB, Acryl-EZE®, Eudragit® grades. In some embodiments, an enteric coating may comprise about 5% to about 10%, about 5% to about 20%, 8 to about 15%, about 8% to about 20%, about 10% to about 20%, or about 12 to about 20%, or about 18% of a contemplated tablet by weight. For example, enteric coatings may include an ethylacrylate-methacrylic acid copolymer.

For example, in a contemplated embodiment, a tablet is provided that comprises or consists essentially of about 0.5% to about 70%, e.g. about 0.5% to about 10%, or about 1% to about 20%, by weight of a compound described herein or a pharmaceutically acceptable salt thereof. Such a tablet may include for example, about 0.5% to about 60% by weight of mannitol, e.g. about 30% to about 50% by weight mannitol, e.g. about 40% by weight mannitol; and/or about 20% to about 40% by weight of microcrystalline cellulose, or about 10% to about 30% by weight of microcrystalline cellulose. For example, a disclosed tablet may comprise an intragranular phase that includes about 30% to about 60%, e.g. about 45% to about 65% by weight, or alternatively, about 5 to about 10% by weight of a compound described herein, about 30% to about 50%, or alternatively, about 5% to about 15% by weight mannitol, about 5% to about 15% microcrystalline cellulose, about 0% to about 4%, or about 1% to about 7% hydroxypropylmethylcellulose, and about 0% to about 4%, e.g. about 2% to about 4% sodium starch glycolate by weight.

In another contemplated embodiment, a pharmaceutical tablet formulation for oral administration of a compound described herein comprises an intra-granular phase, wherein the intra-granular phase includes a compound described herein or a pharmaceutically acceptable salt thereof (such as a sodium salt), and a pharmaceutically acceptable filler, and which may also include an extra-granular phase, that may include a pharmaceutically acceptable excipient such as a disintegrant. The extra-granular phase may include components chosen from microcrystalline cellulose, magnesium stearate, and mixtures thereof. The pharmaceutical composition may also include an enteric coating of about 12% to 20% by weight of the tablet. For example, a pharmaceutically acceptable tablet for oral use may comprise about 0.5% to 10% by weight of a compound described herein or a pharmaceutically acceptable salt thereof, about 30% to 50% by weight mannitol, about 10% to 30% by weight microcrystalline cellulose, and an enteric coating comprising an ethylacrylate-methacrylic acid copolymer.

In another example, a pharmaceutically acceptable tablet for oral use may comprise an intra-granular phase, comprising about 5 to about 10% by weight of a compound described herein or a pharmaceutically acceptable salt thereof, about 40% by weight mannitol, about 8% by weight microcrystalline cellulose, about 5% by weight hydropropylmethyl cellulose, and about 2% by weight sodium starch glycolate; an extra-granular phase comprising about 17% by weight microcrystalline cellulose, about 2% by weight sodium starch glycolate, about 0.4% by weight magnesium stearate; and an enteric coating over the tablet comprising an ethylacrylate-methacrylic acid copolymer.

In some embodiments the pharmaceutical composition may contain an enteric coating comprising about 13% or about 15%, 16%, 17% or 18% by weight, e.g., AcrylEZE® (see, e.g., PCT Publication No. WO2010/054826, which is hereby incorporated by reference in its entirety).

The rate at which point the coating dissolves and the active ingredient is released is its dissolution rate. In an embodiment, a contemplated tablet may have a dissolution profile, e.g. when tested in a USP/EP Type 2 apparatus (paddle) at 100 rpm and 37° C. in a phosphate buffer with a pH of 7.2, of about 50% to about 100% of a compound described herein releasing after about 120 minutes to about 240 minutes, for example after 180 minutes. In another embodiment, a contemplated tablet may have a dissolution profile, e.g. when tested in a USP/EP Type 2 apparatus (paddle) at 100 rpm and 37° C. in diluted HCl with a pH of 1.0, where substantially none of the compound is released after 120 minutes. A contemplated tablet, in another embodiment, may have a dissolution profile, e.g. when tested in USP/EP Type 2 apparatus (paddle) at 100 rpm and 37° C. in a phosphate buffer with a pH of 6.6, of about 10% to about 30%, or not more than about 50%, of the compound releasing after 30 minutes.

In some embodiments, methods provided herein may further include administering at least one other agent that is directed to treatment of conditions, diseases, and disorders disclosed herein. In one embodiment, contemplated other agents may be co-administered (e.g., sequentially or simultaneously).

Non-limiting examples of such combination therapy include combination of one or more compounds of the invention with an anti-inflammatory agent, an antibiotic agent, an immunosuppressant, an immunomodulator, or an analgesic agent.

Agents contemplated include immunosuppressive agents including glucocorticoids, cytostatics, antibodies, agents acting on immunophilins, interferons, opioids, TNF binding proteins, mycophenolate, and small biological agents. For example, contemplated immunosuppressive agents include, but are not limited to: tacrolimus, cyclosporine, pimecrolimus, sirolimus, everolimus, mycophenolic acid, fingolimod, dexamethasone, fludarabine, cyclophosphamide, methotrexate, azathioprine, leflunomide, teriflunomide, anakinra, anti-thymocyte globulin, anti-lymphocyte globulin, muromonab-CD3, afutuzumab, rituximab, teplizumab, efalizumab, daclizumab, basiliximab, adalimumab, infliximab, certolizumab pegol, natalizumab, and etanercept. Other contemplated agents include anti-diarrheals, laxatives, iron supplements, and calcium or vitamin D or B-12 supplements.

Exemplary formulations include dosage forms that comprise or consist essentially of about 35 mg to about 500 mg of a compound described herein. For example, formulations that include about 35 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, or 250 mg of a compound described herein are contemplated. In one embodiment, a formulation may include about 40 mg, 80 mg, or 160 mg of a compound described herein. In some embodiments, a formulation may include at least 100 µg of a compound described herein. For example, formulations may include about 0.1 mg, 0.2 mg, 0.3 mg, 0.4 mg, 0.5 mg, 1 mg, 5 mg, 10 mg, 15 mg, 20 mg, or 25 mg of a compound described herein. The amount administered will depend on variables such as the type and extent of disease or indication to be treated, the overall health and size of the patient, the in vivo potency of the compound, the pharmaceutical formulation, and the route of administration. The initial dosage can be increased beyond the upper level in order to rapidly achieve the desired blood-level or tissue level. Alternatively, the initial dosage can be smaller than the optimum, and the dosage may be progressively increased during the course of treatment. Dosing frequency can vary, depending on factors such as route of administration, dosage amount and the disease being treated. Exemplary dosing frequencies are once per day, once per week and once every two weeks. In some embodiments, dosing is once per day for 7 days.

EXAMPLES

The invention is further illustrated by the following examples. The examples are provided for illustrative purposes only, and are not to be construed as limiting the scope or content of the invention in any way.

Example 1: Synthesis of Sample 2

Sample 2 was prepared as shown below in Scheme 1. Compound numbers used in this Example pertain only to this Example; Sample 2 is referred to elsewhere as compound 2.

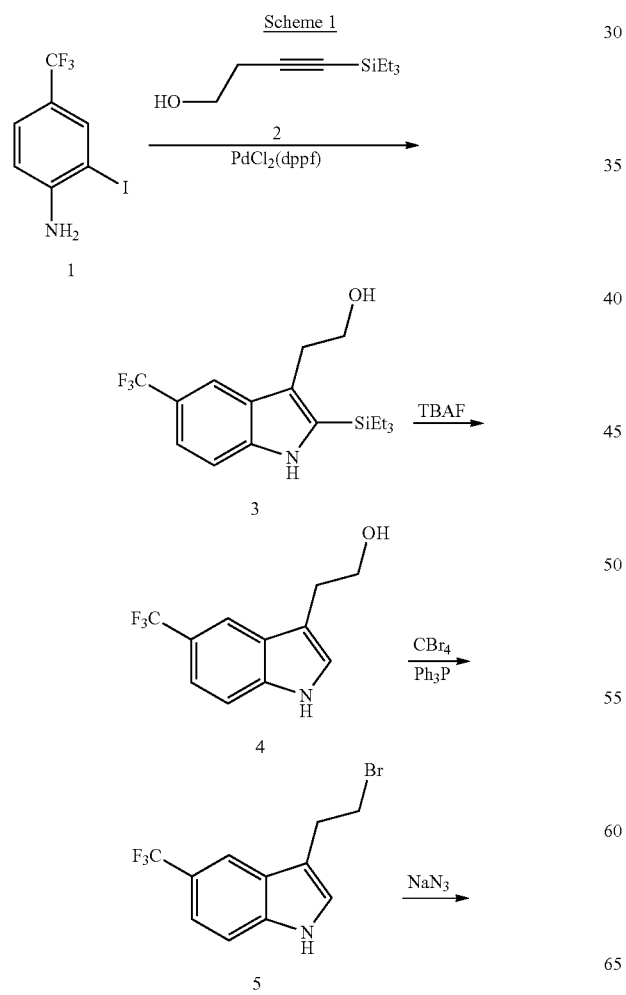

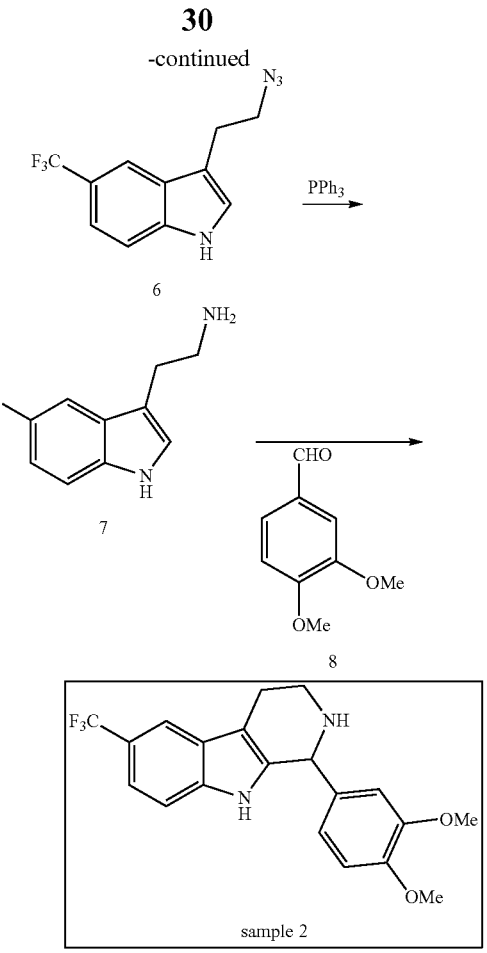

Synthesis of 2-(2-(triethylsilyl)-5-(trifluoromethyl)-1H-indol-3-yl)ethanol (3)

A mixture of 2-iodo-4-(trifluoromethyl)aniline (1) (5.00 g, 17.4 mmol), 4-(triethylsilyl)but-3-yn-1-ol (2) (3.85 g, 1.2 mmol), bis(diphenylphosphino)ferrocene]palladium(II) chloride (0.64 g, 0.87 mmol), lithium chloride (0.732 g, 17.4 mmol) and sodium carbonate (3.7 g, 34.8 mmol)) in 50 mL of N,N-dimethylformamide (DMF) was stirred at 100° C. for 15 h. The reaction mixture was diluted with water and extracted with ethyl acetate. The organic extract was dried over $Na_2SO_4$ and concentrated under reduced pressure. The crude material was purified by silica gel chromatography to afford 7.00 g of the title compound as yellow oil, which contained ~20% of starting material (2). The product was used in the next step without further purification. $^1$H NMR (300 MHz, $CDCl_3$) δ 8.2 (bs, 1H), 7.9 (s, 1H), 7.45 (s, 2H), 3.85 (q, J=8.0 Hz, 2H), 3.15 (t, J=6.4 Hz, 2H), 1.46 (t, J=6.0 Hz, 1H), 1.2 (m, 15H); MS (APCI+) m/z=344 (M+H).

Synthesis of 2-(5-(trifluoromethyl)-1H-indol-3-yl)ethanol (4)

A solution of 2-(2-(triethylsilyl)-5-(trifluoromethyl)-1H-indol-3-yl)ethanol (3) (2.00 g, 5.83 mmol) in 15 mL of tetrahydrofuran (THF) was added tetrabutylammonium fluoride (7.0 mL, 1 M in THF) and the reaction mixture was stirred at room temperature (rt) for 72 h. The reaction mixture was diluted with water and extracted with ethyl acetate. The organic extract was dried over $Na_2SO_4$ and concentrated under reduced pressure. The crude material was purified by silica gel chromatography to afford 1.02 g (75%) of the title compound as pale yellow oil. $^1$H NMR (300 MHz, CDCl$_3$) δ 8.3 (bs, 1H), 7.96 (s, 1H), 7.45 (s, 2H), 7.2 (s, 1H), 3.90 (t, J=6.8 Hz, 2H), 3.05 (t, J=6.8 Hz, 2H); MS (APCI+) m/z=230 (M+H).

Synthesis of 3-(2-bromoethyl)-5-(trifluoromethyl)-1H-indole (5)

A solution of 2-(5-(trifluoromethyl)-1H-indol-3-yl)ethanol (4) (1.00 g, 4.36 mmol) in THF (10 ml) was added to a solution of triphenyl phosphine (2.30 g, 8.72 mmol) and perbromomethane (4.40 g, 13.1 mmol) in THF (10 mL) pre-stirred for 1 h. The resulting mixture was stirred at rt for 3 h. The reaction mixture was then filtered and concentrated under reduced pressure. The crude material was purified by silica gel chromatography to afford 0.66 g (51%) of the title compound as yellow oil. $^1$H NMR (300 MHz, CDCl$_3$) δ 8.25 (bs, 1H), 7.9 (s, 1H), 7.4 (s, 2H), 7.2 (s, 1H), 3.7 (t, J=7.8 Hz, 2H), 3.27 (t, J=7.8 Hz, 2H).

Synthesis of 3-(2-azidoethyl)-5-(trifluoromethyl)-1H-indole (6)

A mixture of 3-(2-bromoethyl)-5-(trifluoromethyl)-1H-indole (5) (0.66 g, 2.26 mmol) and sodium azide (0.44 g; 6.8 mmol) in DMF (10 mL) was stirred at 70° C. for 4 h. The reaction mixture was diluted with water and extracted with ethyl acetate. The organic layer was successively washed with brine, sodium thiosulfate, dried and concentrated under reduced pressure. The crude material was purified by silica gel chromatography to afford 0.61 g (100%) of the title compound as a brown oil. $^1$H NMR (300 MHz, CDCl$_3$) δ 8.15 (bs, 1H), 7.87 (s, 1H), 7.44 (d, J=1.5 Hz, 2H), 7.19 (s, 1H), 3.55-3.61 (t, J=7 Hz, 2H), 3.08 (t, J=7.2 Hz, 2H).

Synthesis of 2-(5-(trifluoromethyl)-(1H-indol-3-yl))ethanamine (7)

A mixture of 3-(2-azidoethyl)-5-(trifluoromethyl)-H-indole (6) (0.61 g, 2.45 mmol) and triphenyl phosphine (1.93 g, 7.41 mmol) in methanol (10 mL) was stirred at 70° C. for 2 h. The reaction mixture was concentrated under reduced pressure and the crude material was purified by silica gel chromatography to afford 0.44 g (75%) of the title compound as a brown oil. $^1$H NMR (300 MHz, CDCl$_3$) δ 8.4 (bs, 1H), 7.9 (s, 1H), 7.4 (s, 2H), 7.25 (s, 1H), 7.13-7.14 (d, J=2.4 Hz, 1H), 3.04 (m, 4H); MS (APCI−) m/z=326 (M−H).

Synthesis of 1-(3,4-dimethoxyphenyl)-6-(trifluoromethyl)-2,3,4,9-tetrahydro-1H-pyrido[3,4-b]indole (Sample 2)

A mixture of 2-(5-(trifluoromethyl)-1H-indol-3-yl))ethanamine (7) (0.40 g, 1.76 mmol) and 3,4-dimethoxybenzaldehyde (8) (0.322 g, 1.93 mmol) in acetic acid (8 ml) was stirred at 80° C. for 24 h. The reaction mixture was concentrated under reduced pressure and the crude material was purified by silica gel chromatography to afford 0.16 g (33%) of the title compound as a white solid. $^1$H NMR (300 MHz, CDCl$_3$) δ 7.9 (s, 1H), 7.71 (bs, 1H), 7.33 (m, 1H), 6.84 (d, J=3.8 Hz, 2H), 5.12 (s, 1H), 3.88 (s, 3H), 3.81 (s, 3H), 3.15 (m, 1H), 2.88 (m, 2H); MS (APCI+) m/z=377 (M+H).

Example 2: Synthesis of Sample 4a

Sample 4a was prepared as shown below in Scheme 2. Compound numbers used in this Example pertain only to this Example; Sample 4a is referred to elsewhere as compound 4a.

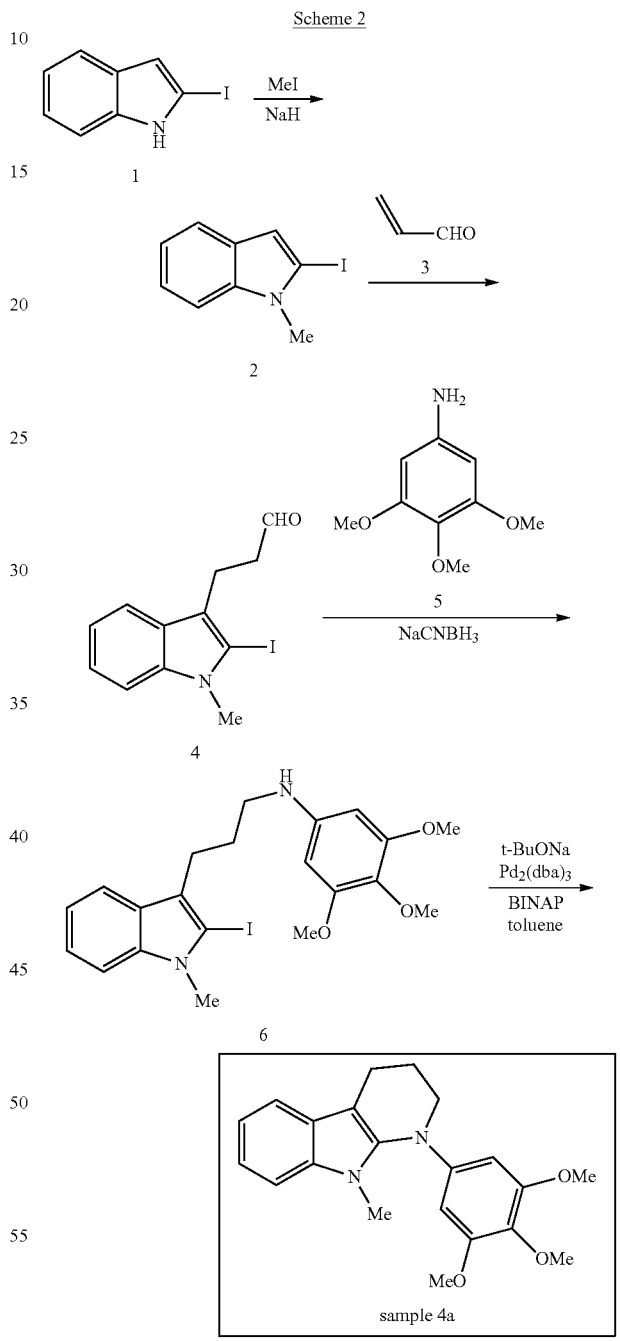

Scheme 2

Synthesis of 2-iodo-1-methyl-1H-indole (2)

A solution of 2-iodo-1H-indole (1) (1.50 g, 6.17 mmol) in THF (20 mL) was added to a suspension of 60% NaH (0.37 g, 9.25 mmol) at 0° C. and the resulting solution was stirred for 10 min. Methyl iodide (1.75 g, 12.3 mmol) was added dropwise and the reaction mixture was allowed to warm slowly from 0° C. to rt over 1 h. The reaction was quenched with saturated NH₄Cl solution (15 mL) and extracted with ethyl acetate. The organic layer was dried over Na₂SO₄ and concentrated under reduced pressure. The crude material was purified by silica gel chromatography to afford 1.27 g (80%) of the title compound as a pale yellow oil. ¹H NMR (400 MHz, CDCl₃) δ 7.71 (d, J=7.6 Hz, 1H), 7.29 (d, J=8 Hz, 1H), 7.14 (t, J=7.6 Hz, 1H), 7.06 (t, J=7.6 Hz, 1H), 6.78 (s, 1H), 3.74 (s, 3H).

Synthesis of 3-(2-iodo-1-methyl-1H-indol-3-yl)propanal (4)

To a stirred solution of acrolein (3) (1.38 g, 24.7 mmol) and N-methylaniline (0.16 g, 1.48 mmol) at 0° C. was added TFA (0.16 g, 1.48 mmol) dropwise and the reaction mixture was stirred at 0° C. for 10 min. 2-Iodo-1-methyl-1H-indole (2) (1.27 g, 4.94 mmol) in CH₂Cl₂ (4 mL) was added and the reaction mixture was slowly stirred from 0° C. to rt for 3 h. The reaction mixture was diluted with water and extracted with dichloromethane (DCM). The organic layer was dried over Na₂SO₄ and concentrated under reduced pressure. The crude material was purified by silica gel chromatography to afford 920 mg (59%) of the title compound as light yellow foam. ¹H NMR (400 MHz, CDCl₃) δ 9.85 (s, 2H), 7.51 (d, J=8.0 Hz, 1H), 7.30 (d, J=8.4 Hz, 1H), 7.16 (t, J=9.8 Hz, 1H), 7.08 (t, J=8 Hz, 1H), 3.75 (s, 3H), 3.75 (s, 3H), 3.09 (t, J=7.6 Hz, 2H), 2.76 (t, J=8.2 Hz, 2H); MS (ESI+) m/z=314 (M+H).

Synthesis of N-(3-(2-iodo-1-methyl-1H-indol-3-yl))propyl-3,4,5-trimethoxyaniline (6)

To a solution of 3-(2-iodo-1-methyl-1H-indol-3-yl)propanal (4) (920 mg, 2.93 mmol) and 3,4,5-trimethoxyaniline (5) (806 mg, 4.40 mmol) in methanol (15 mL) was added 1 drop of acetic acid and the reaction mixture was stirred for 10 min. NaCNBH₃ (0.46 g, 7.32 mmol) was added and stirring continued for 16 h. The reaction mixture was diluted with water and extracted with DCM. The organic layer was dried over Na₂SO₄ and concentrated under reduced pressure. The crude material was purified by silica gel chromatography to afford 1.07 g (74%) of the title compound as an off-white foam. ¹H NMR (400 MHz, CDCl₃) δ 7.53 (d, J=7.8 Hz, 1H), 7.31 (d, J=8.1 Hz, 1H), 7.16 (t, J=9 Hz, 1H), 7.06 (t, J=7.8 Hz, 1H), 5.77 (s, 2H), 3.75 (s, 3H), 3.14 (t, J=7.05 Hz, 2H), 2.88 (t, J=7.2 Hz, 2H), 1.26 (m, 2H); MS (ESI+) m/z=481 (M+H).

Synthesis of 9-methyl-1-(3,4,5-trimethoxyphenyl)-2,3,4,9-tetrahydro-1H-pyrido[2,3-b]indole (Sample 4a)

To a solution of N-(3-(2-iodo-1-methyl-1H-indol-3-yl))propyl)-3,4,5-trimethoxyaniline (6) (1.07 g, 2.22 mmol) in toluene (5 mL) was added tris(dibenzylideneacetone) dipalladium(0) (0.1 g, 0.108 mmol), 2,2'-bis(diphenylphosphino)-1-1"-binaphthalene (0.12 g, 0.216 mmol) and t-BuONa (0.21 g, 2.16 mmol) and the reaction mixture was stirred at 100° C. for 2 h. The mixture was concentrated under reduced pressure and the crude material was purified by silica gel chromatography to afford 280 mg (36%) of the title compound as a white solid. ¹H NMR (400 MHz, CDCl₃) δ 7.45 (d, 1H), 7.15 (m, 3H), 6.19 (s, 2H), 3.82 (s, 3H), 3.71 (m, 8H), 3.26 (s, 3H), 2.79 (t, J=6.6 Hz, 2H), 1.87 (m, 2H); MS (ESI+) m/z=353 (M+H).

Example 3: Synthesis of Sample 13

Sample 13 was prepared as shown below in Scheme 3. Compound numbers used in this Example pertain only to this Example; Sample 13 is referred to elsewhere as compound 13.

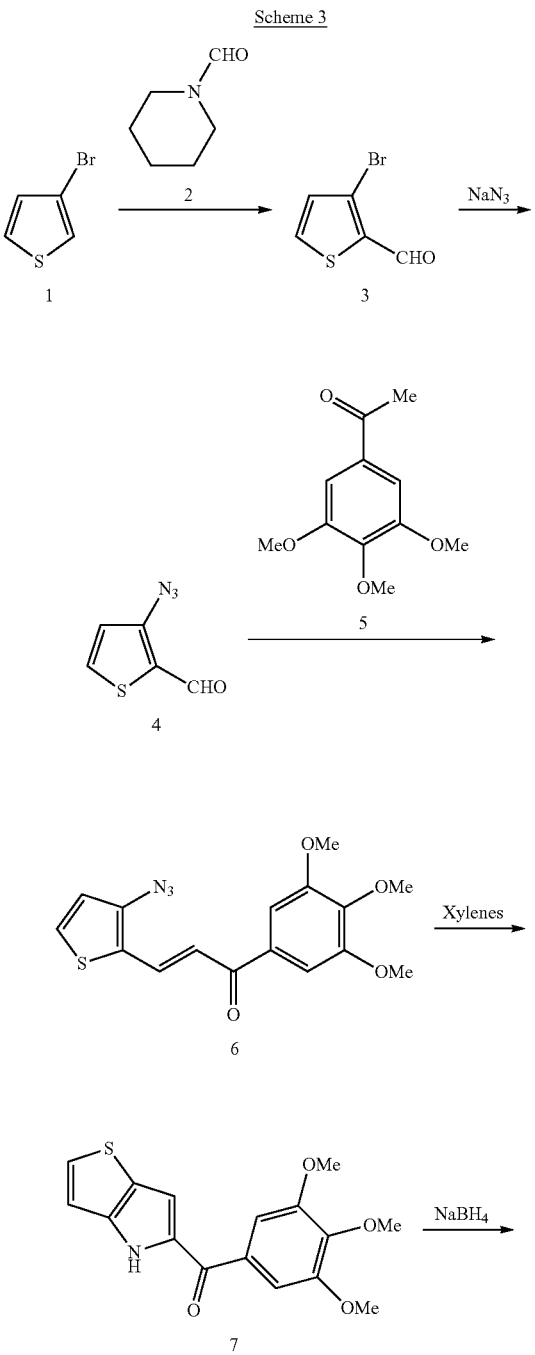

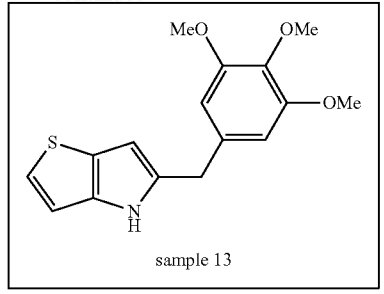

sample 13

Synthesis of 3-bromothiophene-2-carbaldehyde (3)

To a solution of lithium diisopropylamide (31.6 mmol) in 50 mL of THF at −78° C. was added 3-bromothiophene (3.0 g, 31 mmol) (1). After stirring for 1 h, formylpiperidine (3.50 g, 31.6 mmol) (2) was added and the reaction was warmed to 0° C. After 12 h, the reaction mixture was partitioned between DCM and sat. NH$_4$Cl and the organic layer was separated, dried over MgSO$_4$, filtered, and concentrated under reduced pressure. The crude material was purified by silica gel chromatography to afford 1.90 g (54%) of the title compound as a yellow oil. $^1$H NMR (400 MHz, CDCl$_3$) δ 9.99 (s, 1H), 7.71 (d, J=5.2 Hz, 1H), 7.15 (d, J=4.8 Hz, 1H).

Synthesis of 3-azidothiophene-2-carbaldehyde (4)

A solution of 3-bromothiophene-2-carbaldehyde (3) (1.90 g, 0.99 mmol) and sodium azide (3.23 g, 50 mmol) in 50 mL of 1,3-dimethyl-3,4,5,6-tetrahydro-2(1H)-pyrimidinone (DMPU) was heated to 50° C. and stirred for 36 h. The reaction mixture was poured onto ice water and then extracted with DCM. The organic extract was dried over Na$_2$SO$_4$, filtered, and concentrated under reduced pressure. The crude material was purified by silica gel chromatography to afford 1.00 g (66%) of the title compound as a yellow oil. $^1$H NMR (400 MHz, CDCl$_3$) δ 9.93 (s, 1H), 7.72 (d, J=5.2 Hz, 1H), 7.04 (d, J=5.2 Hz, 1H).

Synthesis of (E)-3-(3-azidothiophen-2-yl)-1-(3,4,5-trimethoxyphenyl)prop-2-en-1-one (6)

To a mixture of 3-azidothiophene-2-carbaldehyde (4) (0.80 g, 5.22 mmol) and 1-(3,4,5-trimethoxyphenyl)ethanone (5) (1.64 g, 7.84 mmol) in MeOH (5 mL) was added a solution of NaOH (0.62 g, 15.66 mmol) in water (2 mL) and the reaction mixture was stirred at rt for 16 h. The reaction mixture was diluted with water and extracted with DCM. The organic extract was dried over Na$_2$SO$_4$, filtered and concentrated under reduced pressure. The crude material was purified by silica gel chromatography to afford 1.10 g (61%) of the title compound as a yellow solid. $^1$H NMR (400 MHz, CDCl$_3$) δ 7.88 (d, J=15.6 Hz, 1H), 7.42 (d, J=5.2 Hz, 1H), 7.21 (d, J=15.2 Hz, 3H), 7.00 (d, J=5.2 Hz, 1H), 3.94 (d, J=5.2 Hz, 9H); MS (ESI+) m/z=346 (M+H).

Synthesis of (4H-thieno[3,2-b]pyrrol-5-yl)(3,4,5-trimethoxyphenyl)methanone (7)

A solution of (E)-3-(3-azidothiophen-2-yl)-1-(3,4,5-trimethoxyphenyl)prop-2-en-1-one (6) (1.20 g, 3.48 mmol) in 10 mL of xylenes was stirred at 150° C. for 30 min. The reaction mixture was concentrated under reduced pressure and the crude material was purified by silica gel chromatography to afford 1.00 g (91%) of the title compound as an off-white solid. $^1$H NMR (300 MHz, CDCl$_3$) δ 9.48 (bs, 1H), 7.42 (d, J=5.4 Hz, 1H), 7.20 (s, 2H), 7.11 (s, 1H), 7.01 (d, J=5.7 Hz, 1H), 3.94 (d, J=1.8 Hz, 9H); MS (ESI+) m/z=318 (M+H).

Synthesis of 5-(3,4,5-trimethoxybenzyl)-4H-thieno[3,2-b]pyrrole (Sample 13)

A mixture of (4H-thieno[3,2-b]pyrrol-5-yl)(3,4,5-trimethoxyphenyl)methanone (7) (0.80 g; 2.52 mmol) and sodium borohydride (480 mg, 12.7 mmol) in 2-propanol (10 mL) was stirred in a sealed tube at 100° C. for 2 h. The reaction mixture was cooled and diluted with water and extracted with DCM. The organic extract was dried over Na$_2$SO$_4$ and concentrated. The crude material was purified by silica gel chromatography to afford 280 mg (37%) of the title compound as a white solid. $^1$H NMR (300 MHz, CDCl$_3$) δ 7.92 (bs, 1H), 6.99 (d, J=5.1 Hz, 1H), 6.86 (d, J=5.1 Hz, 1H), 6.46 (s, 2H), 6.26 (s, 1H), 4.02 (s, 2H), 3.83 (t, J=3.75 Hz, 9H); MS (ESI+) m/z=304 (M+H).

Example 4: Synthesis of Sample 15

Sample 15 was prepared as shown below in Scheme 4. Compound numbers used in this Example pertain only to this Example; Sample 15 is referred to elsewhere as compound 15.

Scheme 4

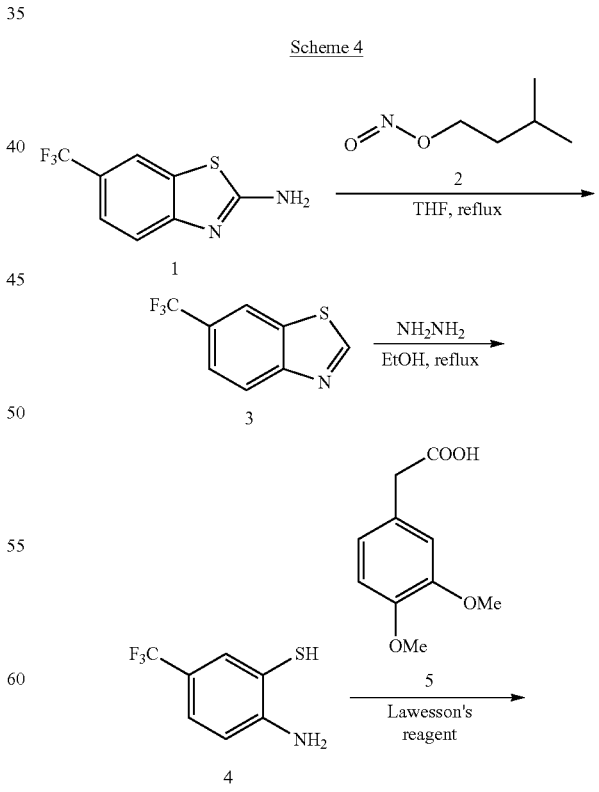

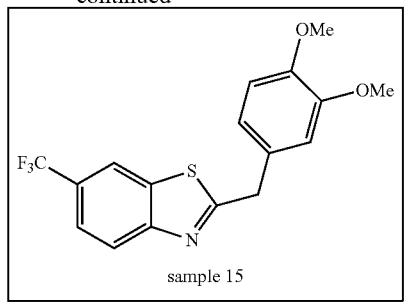

sample 15

Synthesis of 6-(trifluoromethyl)benzo[d]thiazole (3)

To a solution of 6-(trifluoromethyl)benzothiazol-2-amine (1) (2.00 g, 9.17 mmol) in 20 mL of THF was added isoamyl nitrite (3.22 g, 27.5 mmol). The mixture was heated to reflux for 30 min, quenched with water, and extracted with ethyl acetate. The organic extract was dried over $Na_2SO_4$ and concentrated under reduced pressure. The crude material was purified by silica gel chromatography to afford 860 mg (46%) of the title compound as a yellow solid. $^1$H NMR (400 MHz, $CDCl_3$) δ 9.16 (s, 1H), 8.26 (m, 2H), 7.78 (d, J=1.2 Hz, 1H).

Synthesis of 2-amino-5-(trifluoromethyl)benzenethiol (4)

A solution of 6-(trifluoromethyl)benzo[d]thiazole (3) (830 mg, 4.08 mmol) and hydrazine monohydrate (1.52 g, 30.6 mmol) in ethanol (20 mL) was heated to reflux for 1.5 h. The mixture was added to a solution of acetic acid (3 mL) in water (100 mL) and extracted with DCM. The organic extract was dried over $Na_2SO_4$ and concentrated under reduced pressure. The crude material was purified by silica gel chromatography to afford 670 mg (84%) of the title compound as a yellow oil. $^1$H NMR (400 MHz, $CDCl_3$) δ 7.62 (d, J=1.2 Hz, 1H), 7.39 (dd, J=8.4, 2.0 Hz, 1H), 6.75 (d, J=8.4 Hz, 1H), 4.49 (s, 2H), 2.95 (s, 1H).

Synthesis of 2-(3,4-dimethoxybenzyl)-6-(trifluoromethyl)benzo[d]thiazole (Sample 15)

2-amino-5-(trifluoromethyl)benzenethiol (4) (400 mg, 2.07 mmol), 2-(3,4-dimethoxyphenyl) acetic acid (5) and Lawesson's reagent (0.29 g, 0.72 mmol) in a sealed tube was subjected to microwave heating at 190° C. for 5 min. The crude material was purified by silica gel chromatography to afford 320 mg (43%) of the title compound as a white solid. $^1$H NMR (400 MHz, $CDCl_3$) δ 8.08 (s, 1H), 8.06 (s, 1H), 7.69 (d, J=7.5 Hz, 1H), 6.91 (m, 3H), 4.40 (s, 1H), 3.87 (d, J=6.0 Hz, 6H); MS (ESI+) m/z=354 (M+H).

Example 5: Synthesis of Sample 17

Sample 17 was prepared as shown below in Scheme 5. Compound numbers used in this Example pertain only to this Example; Sample 17 is referred to elsewhere as compound 17.

Scheme 5

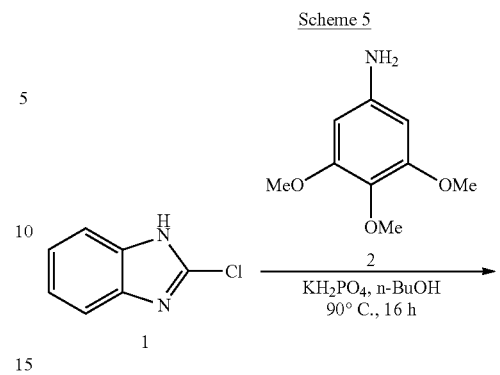

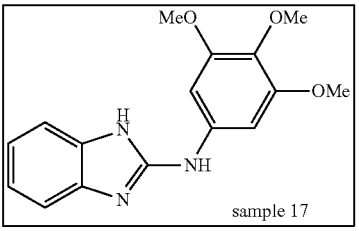

sample 17

Synthesis of N-(3,4,5-trimethoxyphenyl)-1H-benzo[d]imidazol-2-amine (Sample 17)

A mixture of 2-chloro-1H-benzo[d]imidazole (1) (0.40 g, 2.63 mmol), potassium dihydrogenphosphate (0.36 g, 2.63 mmol) and 3,4,5-trimethoxyaniline (0.48 g, 2.63 mmol) in 20 mL of n-BuOH was stirred at 90° C. for 16 h. The reaction mixture was diluted with water and extracted with ethyl acetate. The organic extract was dried over $Na_2SO_4$ and concentrated under reduced pressure. The crude material was purified by silica gel chromatography to afford 0.43 g (54%) of the title compound as an off-white solid. $^1$H NMR (300 MHz, $CDCl_3$) δ 10.8 (s, 1H), 9.29 (s, 1H), 7.28 (bs, 2H), 7.12 (s, 2H), 6.97 (bs, 2H), 3.79 (s, 6H), 3.62 (s, 3H); MS (ESI+) m/z=300 (M+H).

Example 6: Synthesis of Sample 24

Sample 24 was prepared as shown below in Scheme 6. Compound numbers used in this Example pertain only to this Example; Sample 24 is referred to elsewhere as compound 24.

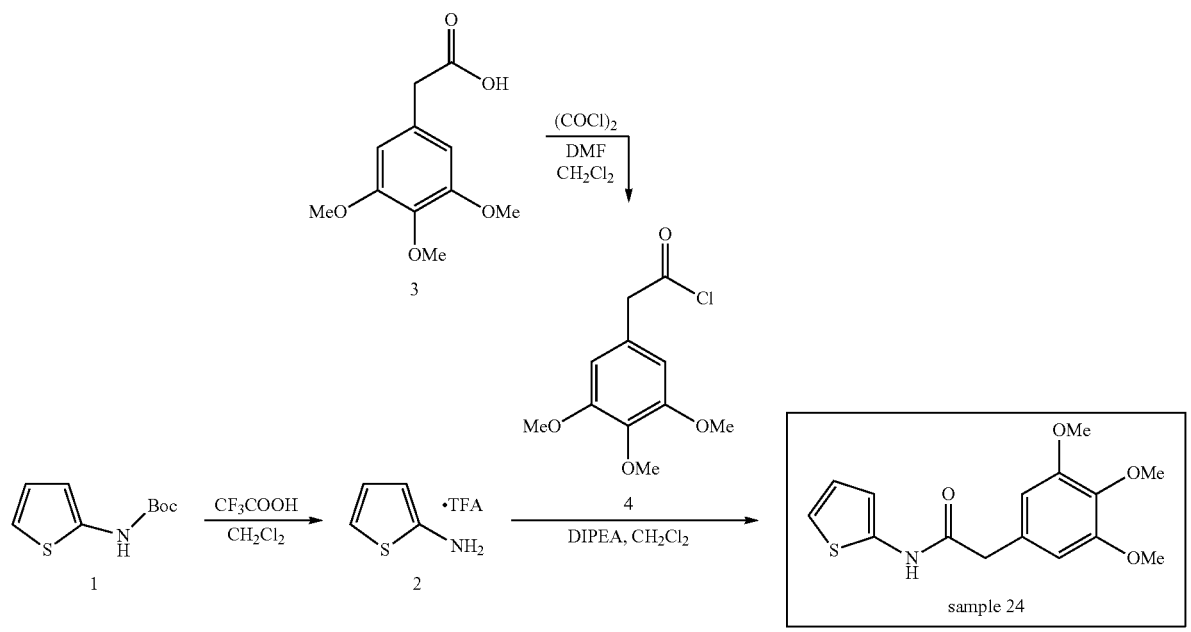

Scheme 6

Synthesis of thiophen-2-amine-TFA salt (2)

To a solution of tert-butyl thiophen-2-ylcarbamate (1) (0.50 g, 2.51 mmol) in 10 mL of DCM was added 2,2,2-trifluoroacetic acid (1.43 g, 12.55 mmol). The mixture was stirred at rt for 2 h. The reaction mixture was concentrated under reduced pressure to afford ~0.50 g of the title compound, which was directly used for the next step without purification.

Synthesis of 2-(3,4,5-trimethoxyphenyl)acetyl chloride (4)

To an ice-cold solution of 2-(3,4,5-trimethoxyphenyl) acetic acid (3) (0.40 g, 1.77 mmol) in 10 mL of DCM was added oxalyl chloride (0.67 g, 5.30 mmol) followed by 1 drop of DMF. The mixture was stirred from 0° C. to rt for 2 h. The reaction mixture was concentrated under reduced pressure to afford ~0.50 g of the title compound, which was used in the next step without purification.

Synthesis of N-(thiophen-2-yl)-2-(3,4,5-trimethoxyphenyl) acetamide (Sample 24)

To an ice-cold solution of thiophen-2-amine-TFA salt (2) (~0.50 g, crude) and diisopropylethylamine (DIPEA) (0.99 g, 7.65 mmol) in 10 mL of DCM was added a solution of 2-(3,4,5-trimethoxyphenyl)acetyl chloride (4) (~0.50 g, crude) in 5 mL of DCM and the reaction mixture was allowed to warm from 0° C. to rt over 2 h with stirring. The reaction mixture was diluted with water and extracted with DCM. The organic extract was dried over $Na_2SO_4$ and concentrated under reduced pressure. The crude material was purified by silica gel chromatography to afford 0.25 g of the title compound as a white solid. $^1$H NMR (300 MHz, $CDCl_3$) δ 7.80 (bs, 1H), 6.87 (m, 1H), 6.81 (m, 1H), 6.56 (m, 1H), 6.51 (s, 2H), 3.86 (s, 9H), 3.70 (s, 2H); MS (ESI+) m/z=308 (M+H).

Figure 23:
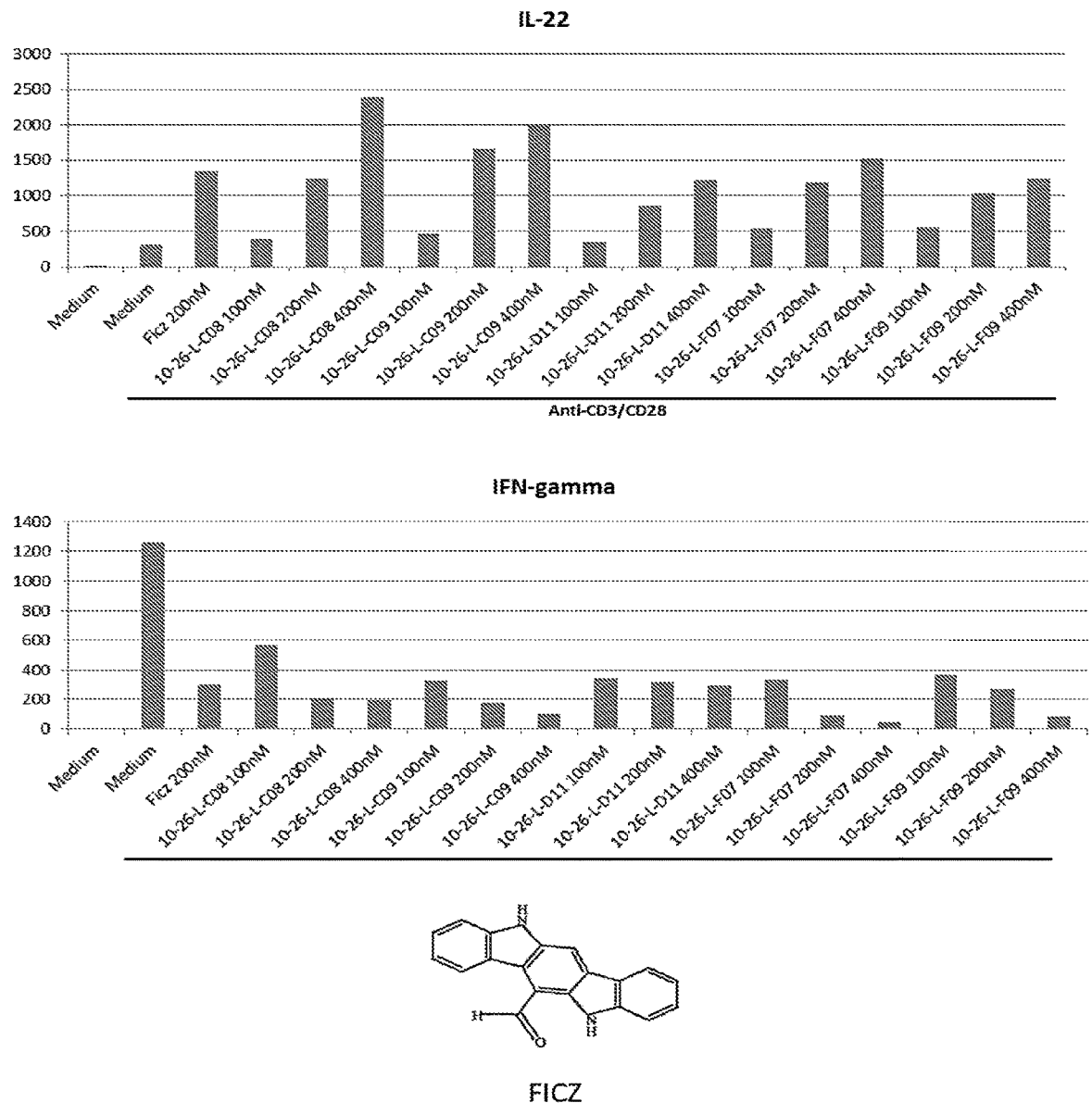
FIG. 23 shows the effects of various compounds of the present disclosure on IL-22 and IFN-γ levels, as well as the chemical structure of known AhR binder Ficz.
Figure 24:
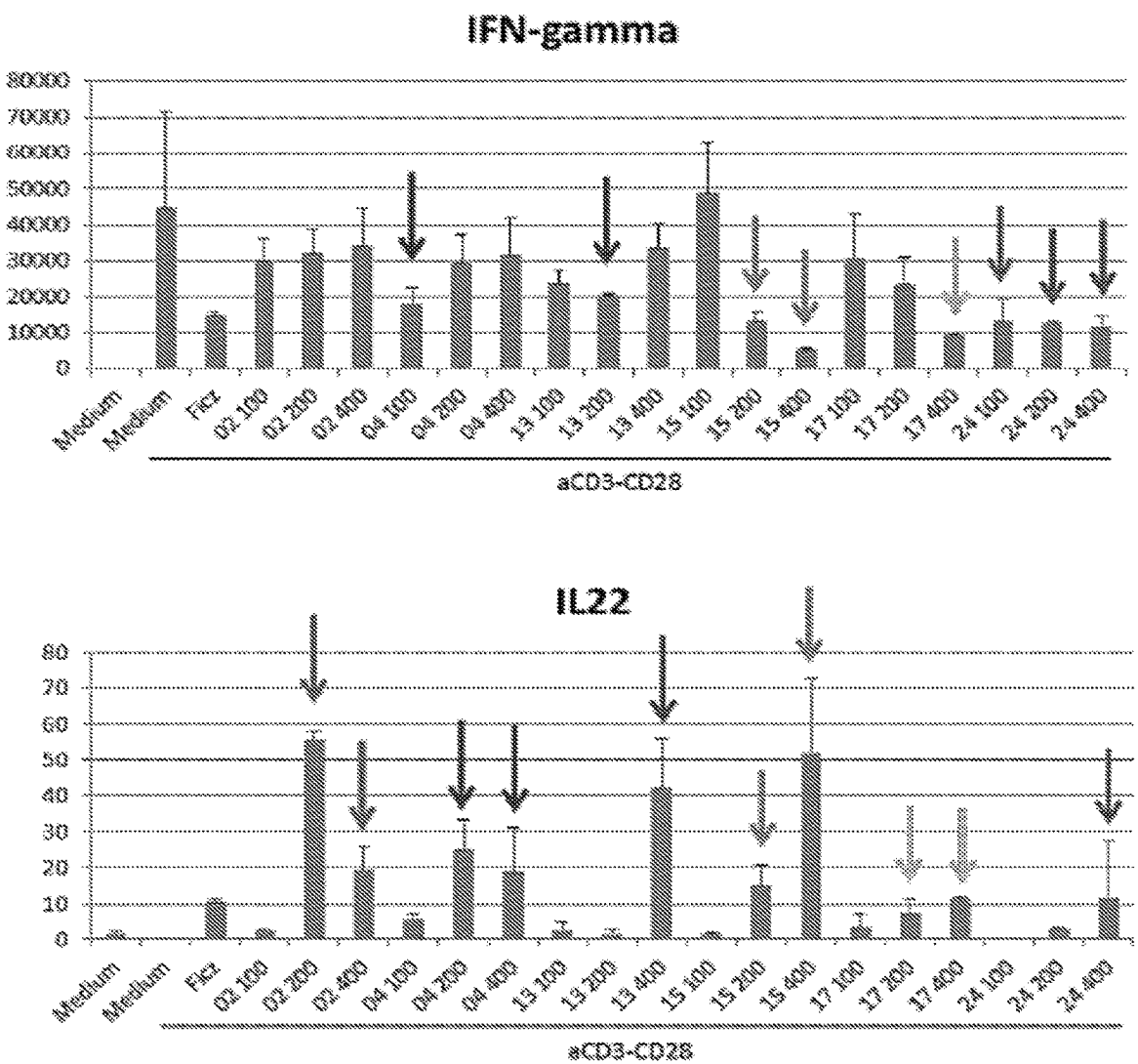
FIG. 24 shows the effects of various compounds of the present disclosure on IL-22 and IFN-γ levels. For each entry, the first number refers to the compound number and the second number refers to the concentration in nM; thus, "02 100" refers to administration of compound 2 at a concentration of 100 nM, "04 200" to administration of compound 4 at a concentration of 200 nM, etc.

Example 7: Design and In Vitro Activity of Selective Ah Receptor Modulators (SAhRM) Exhibiting Anti-Inflammatory Properties As a starting point for the development of the presently disclosed compounds, a group of 47 compounds belonging to a series of 1-aryl-1,2,3,4-tetrahydro-β-carboline derivatives (FIG. 1) were evaluated in vitro for their ability to increase the production of IL-22 and to decrease the production of IFN-γ (FIG. 23). FIG. 24 shows in vitro results for a number of compounds described above. The compounds decrease the production of IFN-7. Notably, in addition to decreasing IFN-γ production, compounds 15 and 17, for example, also strongly increases the production of IL-22.

Conformational Analysis

Conformational analysis of all compounds in the series was carried out in order to determine the spatial position of their substituents and to find among the lowest energy conformers, their putative bioactive conformations.

Molecular modeling studies were performed using SYBYL software version 6.92. Three dimensional models of all compounds were built from a standard fragments library, and their geometry was subsequently optimized using the Tripos force field including the electrostatic term calculated from Gasteiger and Hückel atomic charges. The method of Powell available in the Maximin2 procedure was used for energy minimization until the gradient value was smaller than 0.0001 kcal/mol $A^2$.

For each compound, a conformational search using the random search process as implemented in SYBYL was performed to identify its lowest energy conformations. Random conformational searching is a technique to locate energy minima of a molecule. It involves making random torsion changes to selected bonds, followed by a minimization. The cycle of random changes and minimization is repeated many times. After each cycle the new conformation is compared against all others found so far to see if it is unique. For the random search, the main options used are the maximum hits (n=6) which defined the minimum number of times each conformation must be found to stop searching for new conformations, the RMS threshold (RMS=0.2 Å) which defined the maximum RMS difference between two conformations before they are considered different.

The conformations produced by the random conformational search are fully optimized and can be used immediately for their geometry reoptimization with the semi-empirical MOPAC package version 6.0 using the Hamiltonian AM1 (keywords: PRECISE, NOMM, PARASOK), and Coulson partial atomic charges were calculated using the same method. Table 1 shows conformational spaces for selected compounds.

TABLE 1

| Compounds | n | $E_{min}$ (kcal) | $E_{max}$ (kcal) |
|---|---|---|---|
| CTL-01-07-L-A03 | 2 | 80.76 | 83.82 |
| CTL-01-07-L-A04 | 16 | 43.15 | 47.70 |
| CTL-01-07-L-B05 | 157 | 26.34 | 61.71 |
| CTL-10-26-L-C08 | 126 | −5.12 | 30.49 |
| CTL-10-26-L-C09 | 66 | −27.40 | −10.60 |
| CTL-10-26-L-C10 | 26 | 31.33 | 40.74 |
| CTL-10-26-L-F07 | 30 | 29.75 | 47.35 |
| CTL-10-26-L-F09 | 97 | 26.64 | 51.86 |
| CTL-10-26-L-G10 | 135 | −40.40 | −3.65 |
| CTL-10-26-L-H04 | 202 | −8.80 | 20.56 |
| CTL-10-26-L-H05 | 106 | 26.05 | 45.80 |
| CTL-10-26-L-H06 | 49 | 8.01 | 13.62 |
| CTL-10-29-L-A05 | 253 | −43.79 | −7.10 |
| SGA360 | 853 | −95.57 | −63.71 |
| Leflunomide | 29 | −124.59 | −121.31 | n: number of conformers,
$E_{min}$: lowest energy conformer,
$E_{max}$: highest energy conformer Leflunomide, but not its active metabolite, A771726, activates the AhR (Scheme 7). SGA 360 is a SAhRM that exhibits anti-inflammatory properties in vivo.

Scheme 7

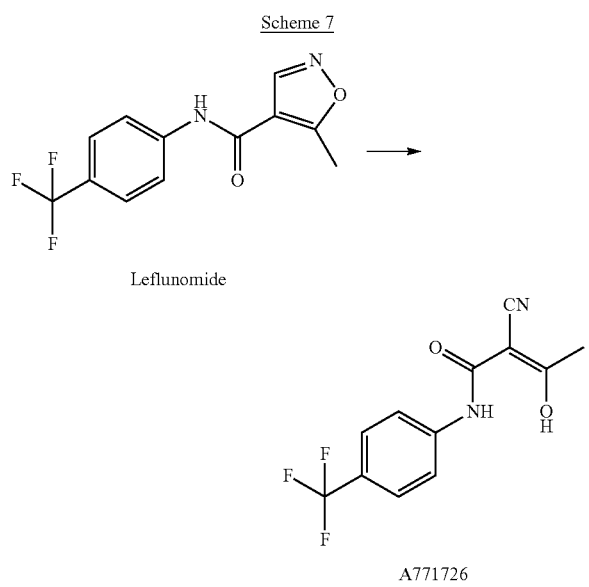

Leflunomide

A771726

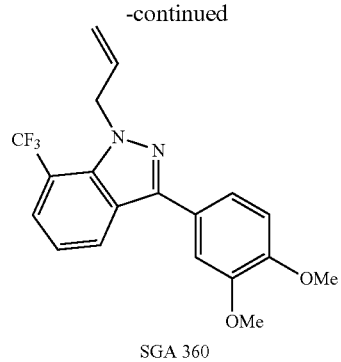

SGA 360

Example 8: AhR Binding

Peripheral blood mononuclear cells (PBMC), isolated from 3 healthy subjects, were isolated by density gradient centrifugation (Lymphoprep; Nycomed Pharma) from 5 mL heparinized blood samples. PBMC were resuspended in RPMI 1640 supplemented with 10% fetal calf serum at a concentration of 1×106 cells/mL, cultured in 24-well culture plates (Falcon Plastic) and stimulated with medium alone or anti-CD3/anti-CD28 (Miltenyi Biotec) antibodies with or without 100, 200, or 400 nM of AhR binding compounds (02, 04, 13, 15, 17, or 24), dimethyl sulfoxide or 6-formylindolo[3,2-b]carbazole (Ficz, 200 nM). Total RNA was extracted from cells cultured for 24 hours. For RNA preparation, cells were lysed in 1 mL of guanidium thiocyanate buffer and subjected to phenol/chloroform extraction using TRizol reagent (Invitrogen). The sample obtained was quantitated by absorbance at 260 nm and complementary DNA (cDNA) was synthetized from 1 mg of total RNA. cDNA was amplified using the following conditions: denaturation for 1 minute at 95° C.; annealing for 30 seconds at 58° C. for IFN-γ, and 60° C. for β-actin; and followed by 30 seconds of extension at 72° C. Primer sequences were as follows: human IFN-γ, forward (SEQ ID NO. 1) 5'-TGGA-GACCATCAAGGAAGAC-3', reverse (SEQ ID NO.2) 5'-GCGTTGGACATTCAAGTCAG-3'. IL-22 was evaluated using commercially available TaqMan probes (Applied Biosystems). β-actin (forward (SEQ ID NO. 3) 5'-AA-GATGACCCAGATCATGTTTGAGACC-3', reverse (SEQ ID NO. 4) 5'-AGCCAGTCCAGACGCAGGAT-3') was used as a housekeeping gene. Gene expression was calculated using the ΔΔCt algorithm.

Example 9: Aryl Hydrocarbon Receptor-Driven Signals Inhibit Collagen Synthesis in the Gut Using both in vitro and in vivo models of fibrosis, we have determined that AhR is a regulator of collagen synthesis in the gut, as described below.

Materials and Methods

Patients and Samples

Mucosal samples were taken from surgical specimens of 10 patients with fibrostenosing CD (median age, 37 years; range: 27-56 years); 7 of these 10 patients were receiving corticosteroids, and the remaining patients were on corticosteroids and azathioprine. Mucosal samples were also taken from 3 patients with ulcerative colitis (UC) undergoing colectomy for a chronic disease unresponsive to medical treatment and 6 UC patients undergoing endoscopy for recent flare-ups (median age, 38 years; range 29-5S years).

Four UC patients were receiving corticosteroids while the remaining were treated with mesalazine. Normal controls included samples taken from 4 patients with irritable bowel syndrome and from macroscopically and microscopically unaffected areas of 6 patients undergoing colectomy for colon cancer (median age, 49 years; range 33-68 years).

Isolation and Culture of Intestinal Fibroblasts

All reagents were purchased from Sigma-Aldrich (Milan, Italy) unless specified. Intestinal fibroblasts were isolated and phenotypically characterized as described elsewhere. In all experiments, fibroblasts were used between passages 3 and 8. To examine whether AhR regulates collagen production, fibroblasts isolated from CD patients were starved overnight and then stimulated with TGF-β1 (TGF-β; 1 ng/mL; Peprotech EC, London, UK) or TNF-α (15 ng/mL; R&D Systems, Abingdon, UK) in the presence or absence of Ficz (final concentration, 100-400 nM; Alexis, Milan, Italy) or 2-methyl-2H-pyrazole-3-carboxylic acid (CH223191; final concentration 10 µM; Calbiochem, Nottingham, England), an AhR antagonist, for 24-48 hours. At the end, cells were used to extract RNA and cell-free supernatants were analyzed for collagen content.

Induction of Colonic Fibrosis

Trinitrobenzene sulfonic acid (TNBS) was dissolved in 45% ethanol and administered intrarectally to 8-week-old female balb/c mice for 7 weeks as previously described. Ficz (1 µg/mouse) or AhR antagonist (CH223191; 10 µg/mouse) was dissolved in phosphate-buffered saline (PBS) and given intraperitoneally every 48 hours after the fifth week of TNBS administration. Control mice were given PBS alone. Mice were examined 3 times a week for signs of colitis including weight loss and killed at week 8; afterwards tissues were collected for histology, RNA analysis and collagen analysis. Colonic sections were stained with H&E and with Masson's trichrome to detect connective deposition. Fibrosis was scored as mild, moderate, or severe as previously reported.

RNA Extraction, Complementary DNA Preparation and Real Time Polymerase Chain Reaction RNA isolation, reverse transcription of the RNA and real-time PCR were carried out as previously described. RNA was extracted by using TRIzol reagent according to the manufacturer's instructions (Invitrogen, Carlsbad, CA). A constant amount of RNA (1 µg per sample) was reverse transcribed into complementary DNA, and this was amplified using the following conditions: denaturation for 1 minute at 95° C.; annealing for 30 seconds at 60° C. for human collagen I (Col1A1), human Col3A1, human alpha smooth muscle actin (α-SMA), and β-actin, at 58° C. for human AhR and mouse Col1A2, followed by 30 seconds of extension at 72° C. Primer sequences were as follows: human Col1A1 (SEQ ID NO. 5) 5'-GGACACAGAGGTTTCAGTGG-3', (SEQ ID NO. 5) 3'-GGTGACTTTGGAGACACAGG-5'; Col3A1 (SEQ ID NO. 6) 5'-GGAGAATGTTGTGCAGTTTGC-3', (SEQ ID NO. 6) 3'-CGTTTGACGTGTTGTAAGAGG-5'; human α-SMA (SEQ ID NO. 7) 5'-TCTGGAGATGGTGT-CACCCA-3', (SEQ ID NO. 7) 3'-ACC-CACTGTGGTAGAGGTCT-5'; human AhR (SEQ ID NO. 8) 5'-GAGCACAAATCAGAGACTGG-3', (SEQ ID NO. 9) 5'-TGGAGGAAGCATAGAAGACC-3'; mouse Col1A2 (SEQ ID NO. 10) 5'-ACACAGTGGTATGGATGGAC-3', (SEQ ID NO. 10) 3'-CAGGTAGGTATGGTGACACA-5'; β-actin ((SEQ ID NO.3) 5'-AAGATGACCCAGAT-CATGTTTGAGACC-3', (SEQ ID NO. 4) 5'-AGCCAGTCCAGACGCAGGAT-3') was used as a housekeeping gene. Gene expression was calculated using the ΔΔCt algorithm.

Flow Cytometry

To assess the intracellular expression of AhR and the phosphorylated (p) form of p38, Erk1/2, NF-kB/p65 and Smad2/3, cells were fixed with 1% formaldehyde for 20 minutes and subsequently permeabilized with 0.5% saponin in 1% bovine serum albumin and stained with anti-AhR (1:50, final dilution; Abcam, Cambridge, UK), anti-p-p38 (pT180/pY182)-PE (final dilution 1:50; BD Biosciences, San Jose, CA), anti-p-ERK1/2 (pT202/pY204; pT184/pY186)-PE (final dilution 1:50; BD Biosciences), anti-p-NF-kB/p65-FITC (1:50 final dilution; eBioscience, San Diego, CA), and anti-p-Smad2/3 (1:50 final dilution; Cell Signaling, Danvers, MA). Appropriate secondary antibody and isotype-matched controls (BD Biosciences) were included in all experiments. Cells were analyzed using a FACS Verseflow cytometer and FACS Suite software (BD Biosciences).

Collagen Assay

Total collagen was measured in fibroblasts-free supernatants and mouse tissue samples by Sircol Collagen Assay Kit (Biocolor Ltd, Belfast, UK) in accordance with the manufacturer's instructions.

Statistical Analysis

Differences between groups were compared using the Student's t-test.

Results

Figure 25:
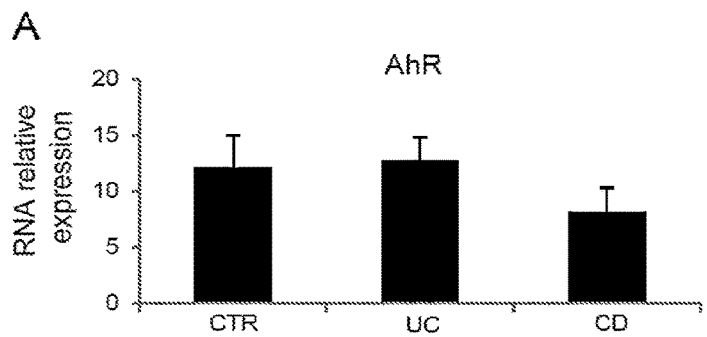
FIG. 25A shows evaluation of AhR transcripts in fibroblasts isolated from gut mucosa of 6 normal patients (control group; CTR), 7 patients with ulcerative colitis (UC), and 7 with Crohn's disease (CD) by real time PCR and normalized to β-actin.
FIG. 25B shows flow cytometry analysis of AhR in fibroblasts isolated from 5 normal patients (CTR), 5 patients with UC, and 5 patients with CD. Right insets show representative histograms of AhR-expressing fibroblasts isolated from one CTR, one patient with UC, and one patient with CD. Staining with an isotype control IgG is also shown. Data indicate mean+/−SD of all experiments. Taken together, these data demonstrate that intestinal fibroblasts constitutively express AhR.
Figure 25:
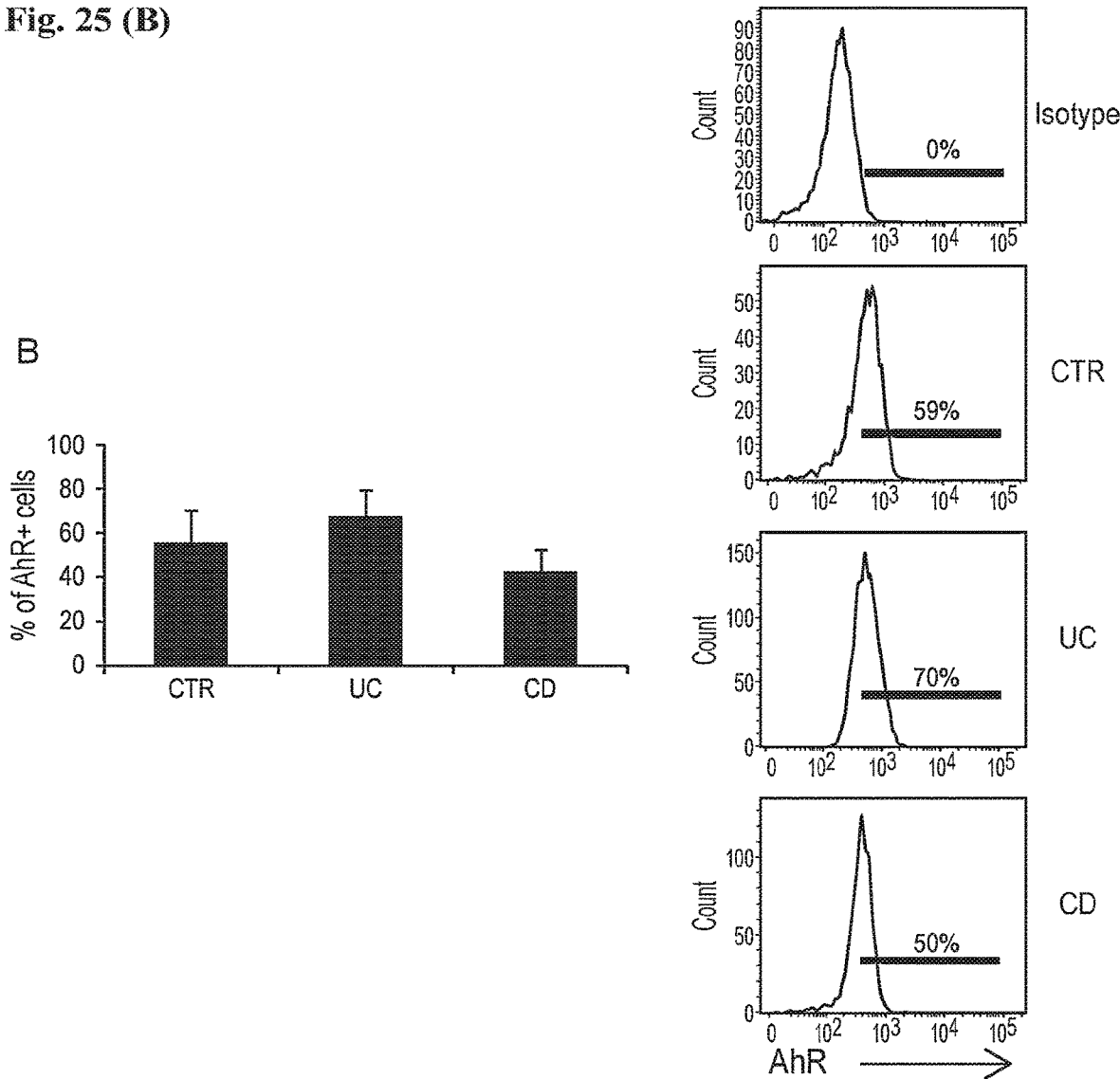
Figure 26:
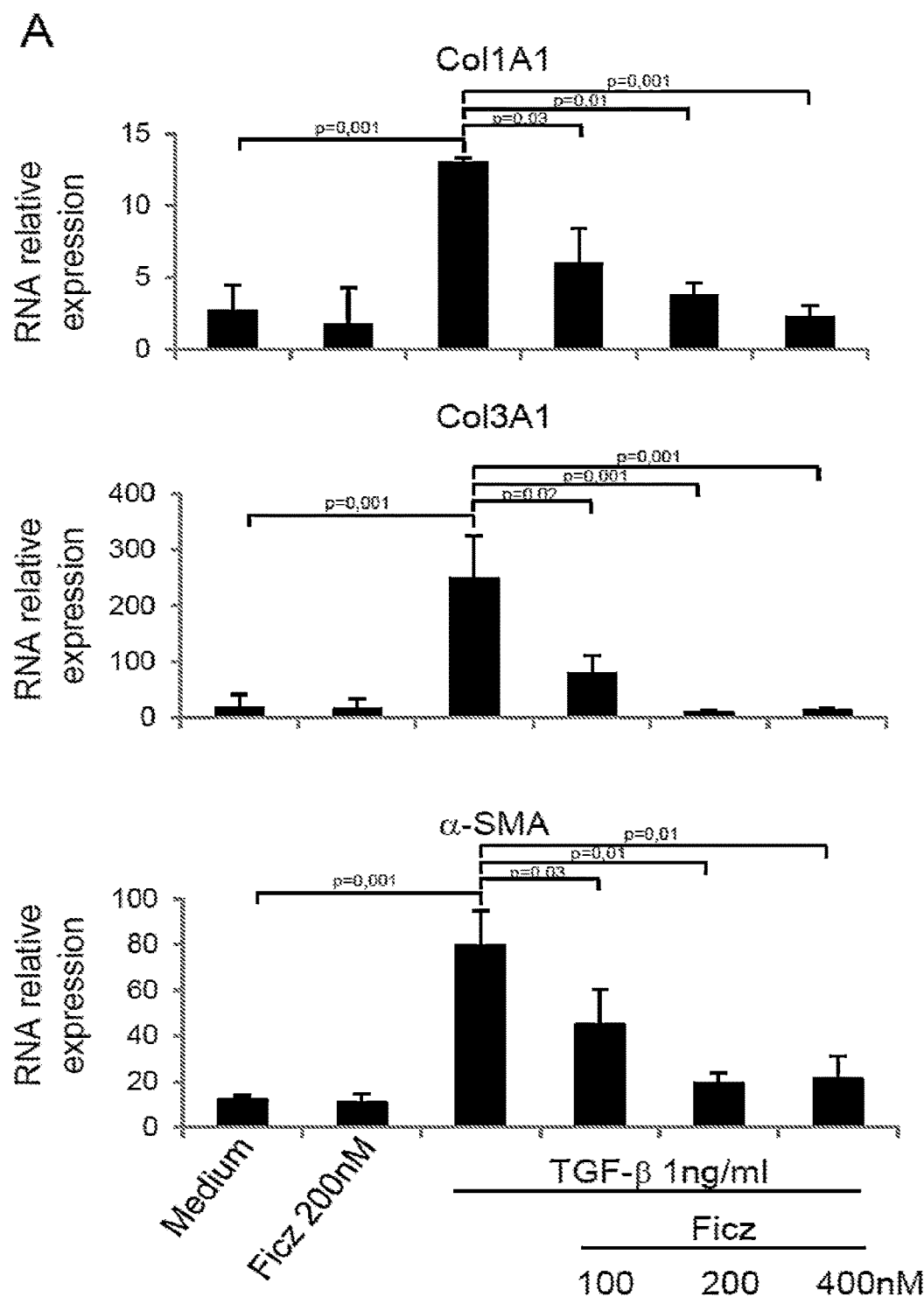
FIG. 26A shows the results of stimulating Crohn's disease (CD) intestinal fibroblasts with TGF-β (1 ng/mL) in the presence or absence of Ficz (100, 200, or 400 nM).
FIG. 26B shows the results of stimulating CD intestinal fibroblasts with TNF-α (15 ng/mL) in the presence or absence of Ficz (100, 200, or 400 nM). Col1A1, Col3A1, and α-SMA were examined by real-time PCR after 24 hours. Data indicate mean+/−SD of 3 experiments. Taken together, these data demonstrate that AhR activation inhibits fibroblast collagen expression induced by pro-fibrotic cytokines.
Figure 26:
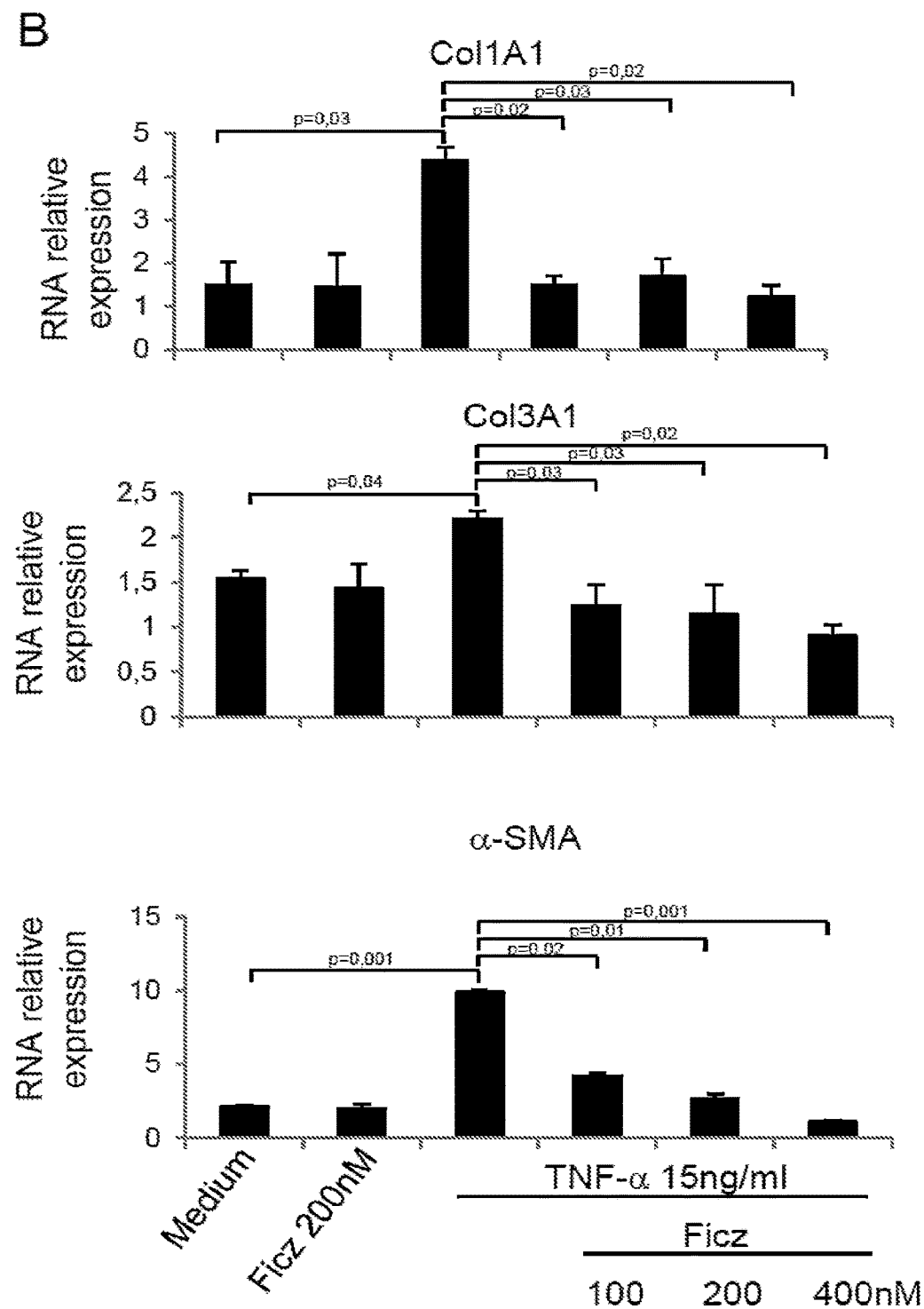
Figure 27:
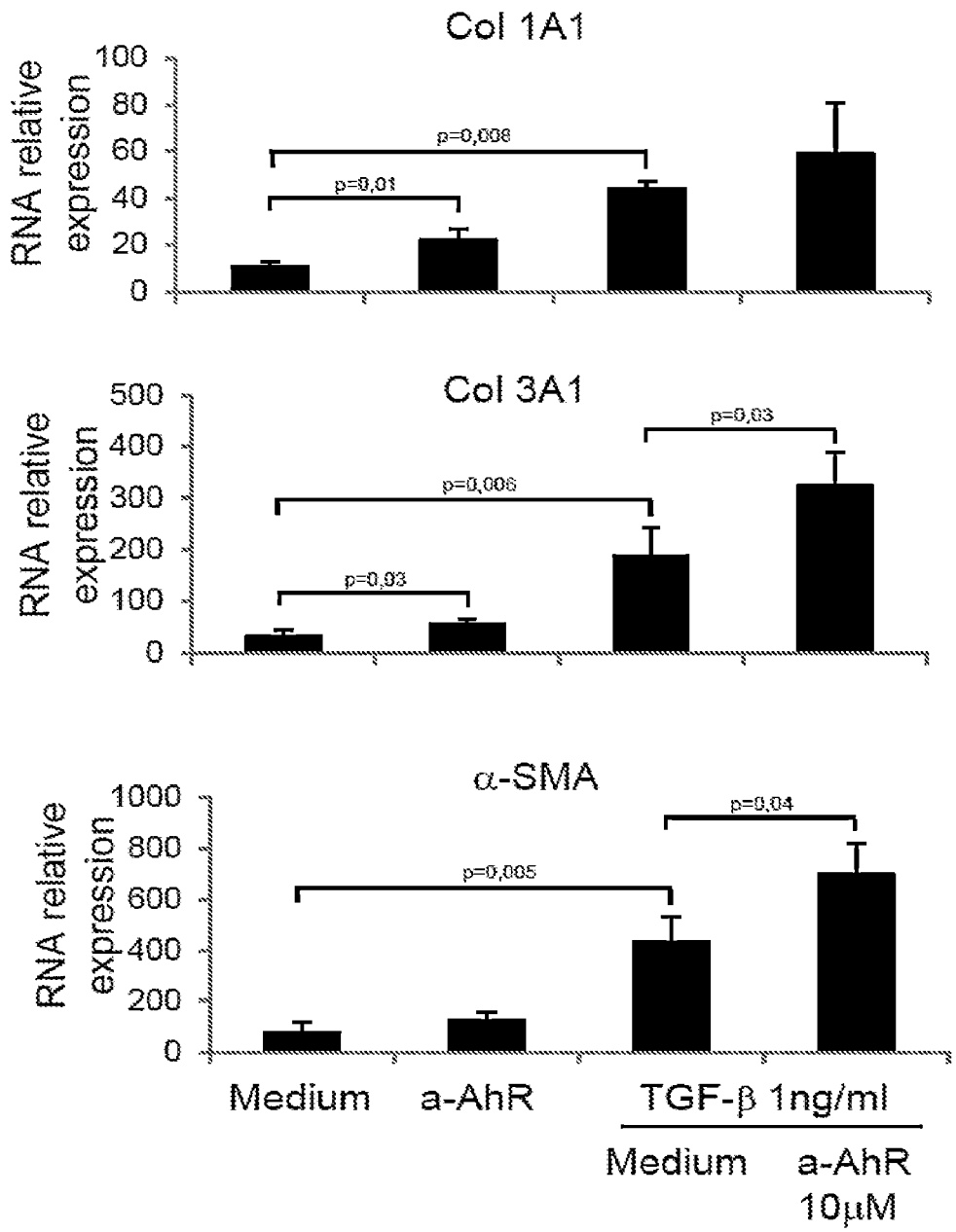
FIG. 27A shows the results of stimulating Crohn's disease (CD) intestinal fibroblasts with TGF-β (1 ng/mL) in the presence or absence of CH223191 (a-AhR, final concentration 10 μM).
FIG. 27B shows the results of stimulating CD intestinal fibroblasts with TNF-α (15 ng/mL) in the presence or absence of CH223191 (a-AhR, final concentration 10 PM). Col1A1, Col3A1, and α-SMA were analyzed by real-time PCR after 24 hours. Data indicate mean+/−SD of 3 experiments.
Figure 27:
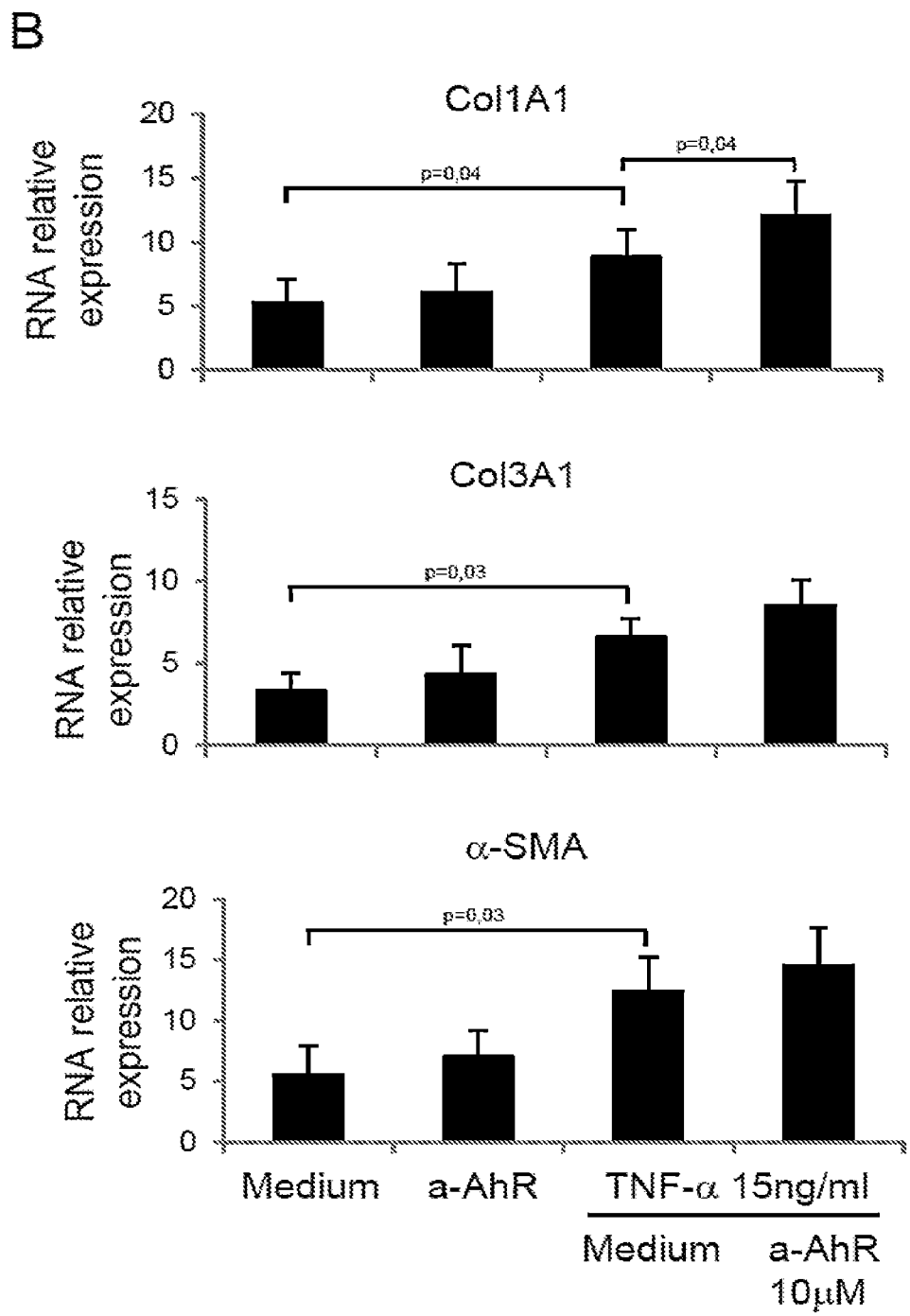

AhR Activation Negatively Regulates Collagen Production by Intestinal Fibroblasts AhR RNA transcripts were constitutively expressed in fibroblasts isolated from the gut of patients with CD, patients with UC and normal controls with no significant differences among groups (FIG. 25A). Flow cytometry analysis showed that nearly 50% of intestinal fibroblasts expressed AhR in both IBD and controls (FIG. 25B). To determine whether AhR activation regulates collagen production, fibroblasts isolated from FS of CD patients were treated with TGF-β 1 or TNF-α, two known inducers of collagen, in the presence or absence of Ficz for 24 hours. As expected, stimulation of fibroblasts with TGF-β1 or TNF-α induced a significant increase of transcripts for Col1A1, Col3A1, and α-SMA, a marker of fibroblast activation (FIGS. 26A-26B). Treatment of fibroblasts with Ficz did not alter the basal RNA expression of Col1A1, Col3A1, and α-SMA but significantly reduced TGF-β1 or TNF-α-driven RNA transcripts for Col1A1, Col3A1, and α-SMA (FIGS. 26A-26B). To further assess the role of AhR in the control of collagen expression, CD fibroblasts were stimulated with TGF-β1 or TNF-α in the presence or absence of CH223191. CH223191 significantly enhanced Col1A1 RNA transcripts in unstimulated fibroblasts as well as RNA expression of Col1A1, Col1A3, and α-SMA in fibroblasts stimulated with TGF-β1 or TNF-α (FIGS. 27A-27B). Analysis of soluble forms of collagen in fibroblast culture supernatants confirmed that, in unstimulated cells, CH223191 but not Ficz collagen significantly up-regulated collagen secretion (FIGS. 28A-28D). Moreover, Ficz dose-dependently inhibited TGF-β1 and TNF-α-induced collagen secretion while CH223191 inhibited such a synthesis (FIGS. 28A-28D). Neither Ficz nor CH223191 changed fibroblast viability or proliferation (data not shown).

AhR Controls Map Kinase Activation in CD Fibroblasts

Activation of p38 and ERK1/2 MAP kinases has been involved in the TGF-β1 and TNF-α-driven collagen induction. Therefore, we next investigated whether the AhR-mediated control of collagen synthesis was associated with changes of this intracellular pathway. To this end, we monitored p38 and ERK1/2 activation by flow-cytometry using specific antibodies, which recognize the phosphorylated/active forms of these proteins.

Figure 29A:
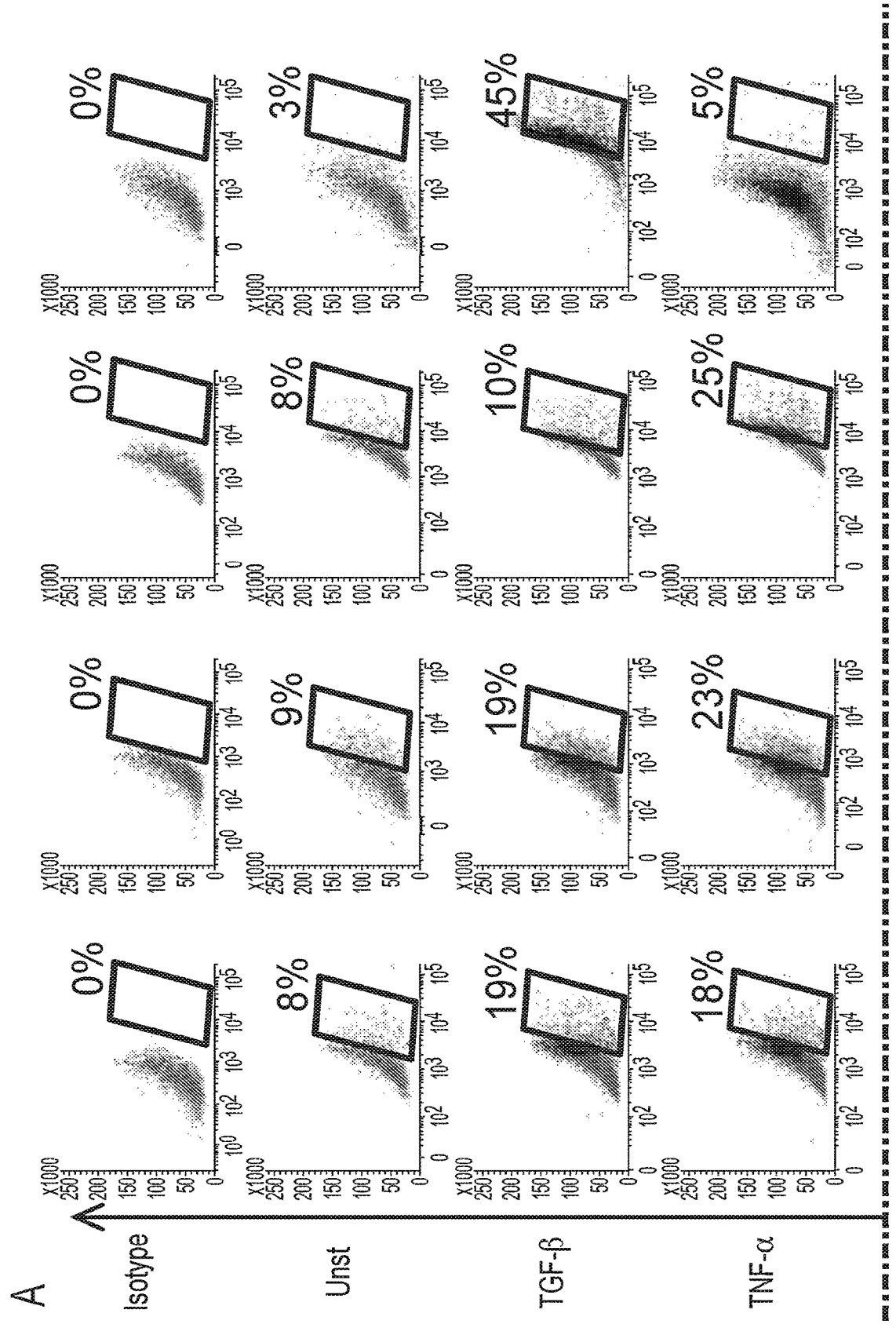
FIG. 29A shows percentages of CD intestinal fibroblasts expressing p-p38+, p-ERK1/2+, p-NF-kBp65+, or p-Smad2/3+ that were either unstimulated (Unst) or stimulated with TGF-β (1 ng/mL) or TNF-α (15 ng/mL) in the presence or absence of Ficz (final concentration 200 nM) or CH223191 (a-AhR, final concentration 10 μM) for 24 h. Assessment of p-P38 (pT180/pY182), p-ERK1/2(pT202/pY204)(pT184/pY186), p-NF-kBp65, and p-Smad2/3 was accomplished by flow cytometry. Numbers indicate the percentages of p-p38+, p-ERK1/2+, p-NF-kBp65+, or p-Smad2/3+ cells in the designated gates. Isotype control stain is also indicated. One of 3 representative experiments in which cells of 3 patients were used is shown.
Figure 29A:
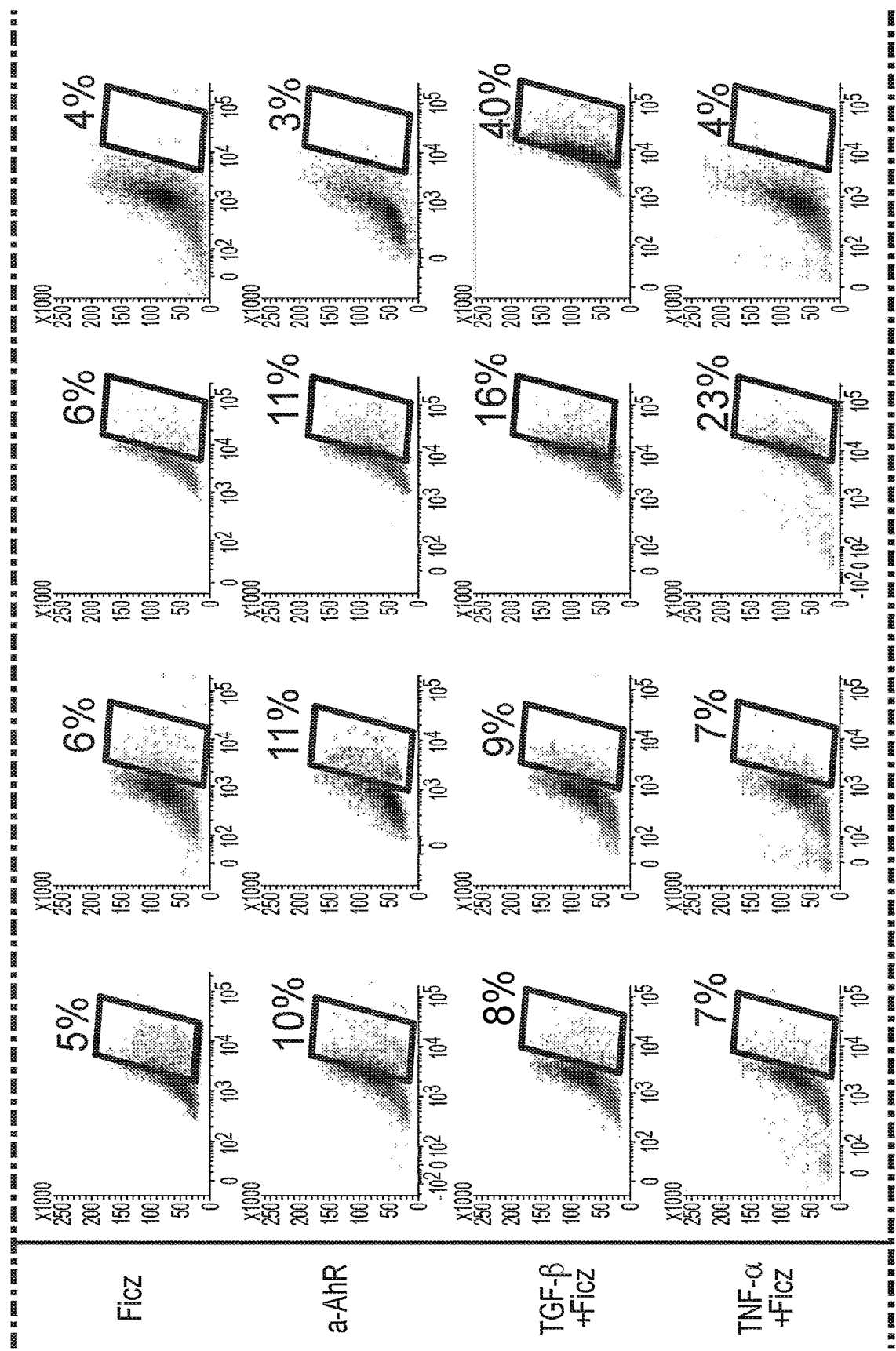
Figure 29A:
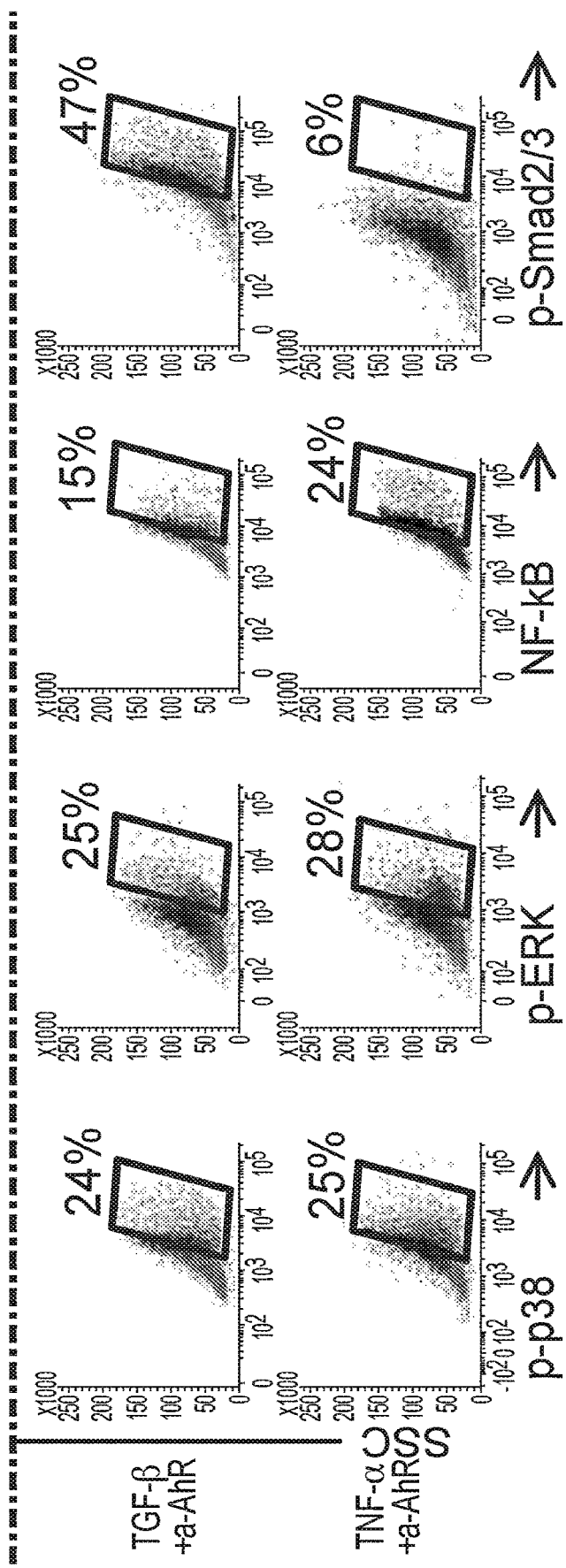
Figure 29:
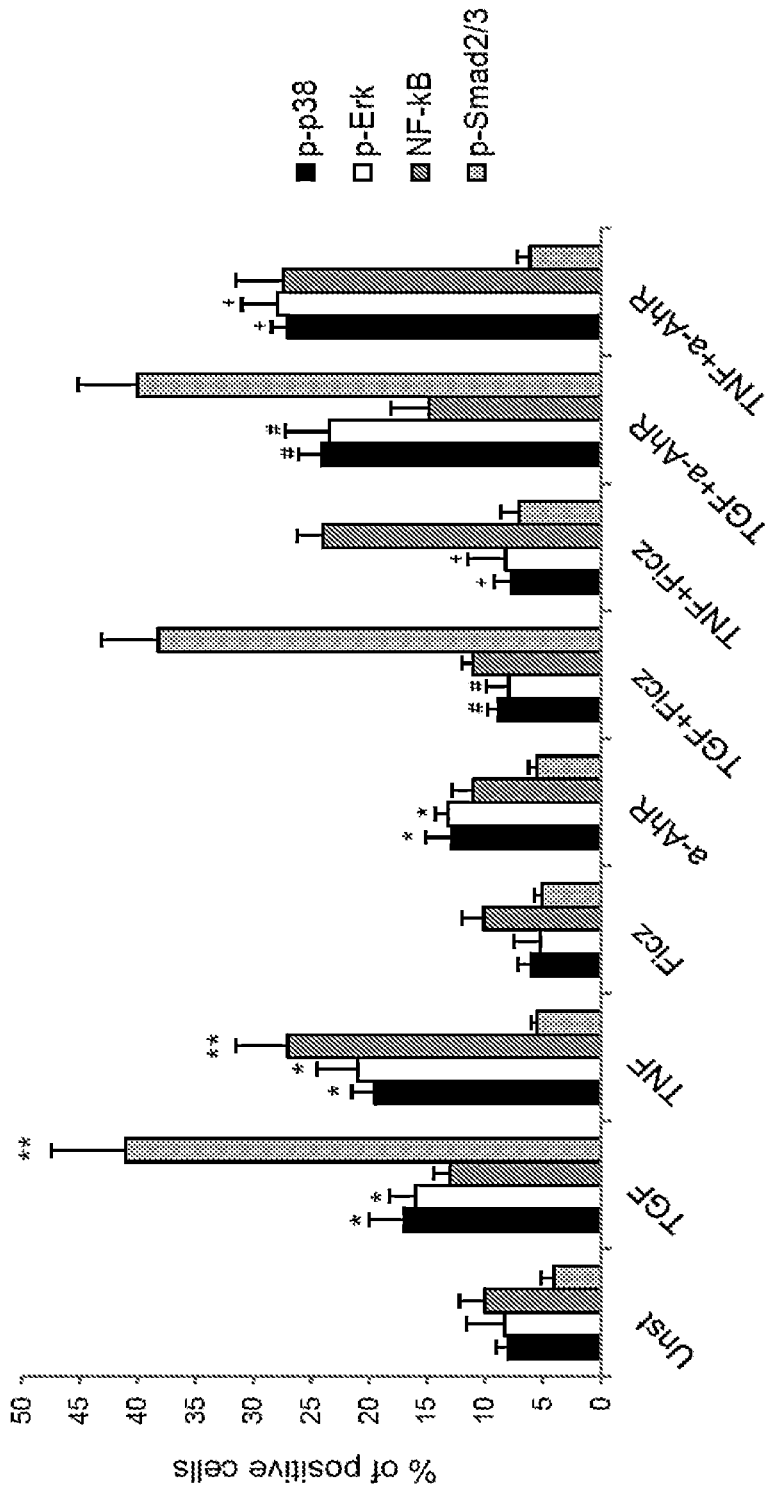
FIG. 29B shows percentages of p-p38+, p-ERK1/2+, p-NF-kBp65+, or p-Smad2/3+ fibroblasts isolated from 3 CD patients stimulated either with TGF-β (1 ng/mL) or TNF-α (15 ng/mL) in the presence or absence of Ficz (final concentration 200 nM) or CH223191 (a-AhR, final concentration 10 μM) for 24 h. Data indicate the mean±SD of 3 experiments. * $p<0.04$ vs. unstimulated; ** $p<0.001$ vs. unstimulated; # $p<0.03$ vs. TGF-β; + $p<0.02$ vs. TNF-α. Taken together, these data demonstrate that AhR activation leads to inactivation of p38 and ERK1/2 in Crohn's disease (CD) fibroblasts.

In unstimulated conditions, the fractions of cells expressing p-p38 or p-ERK1/2 were not affected by Ficz while being significantly increased by CH223191 (FIGS. 29A-29B). TGF-β1 and TNF-α significantly increase the percentages of fibroblasts expressing p-p38 and p-ERK1/2, and this effect was either decreased or increased by Ficz or CH223191, respectively (FIGS. 29A-29B). TGF-β1 and TNF-α also enhanced the fractions of cells expressing p-Smad2/3 or NF-kB/p65 respectively, but neither Ficz nor CH223191 changed such percentages (FIGS. 29A-29B).

AhR Controls TNBS-Induced Intestinal Fibrosis in Mice

Figure 30:
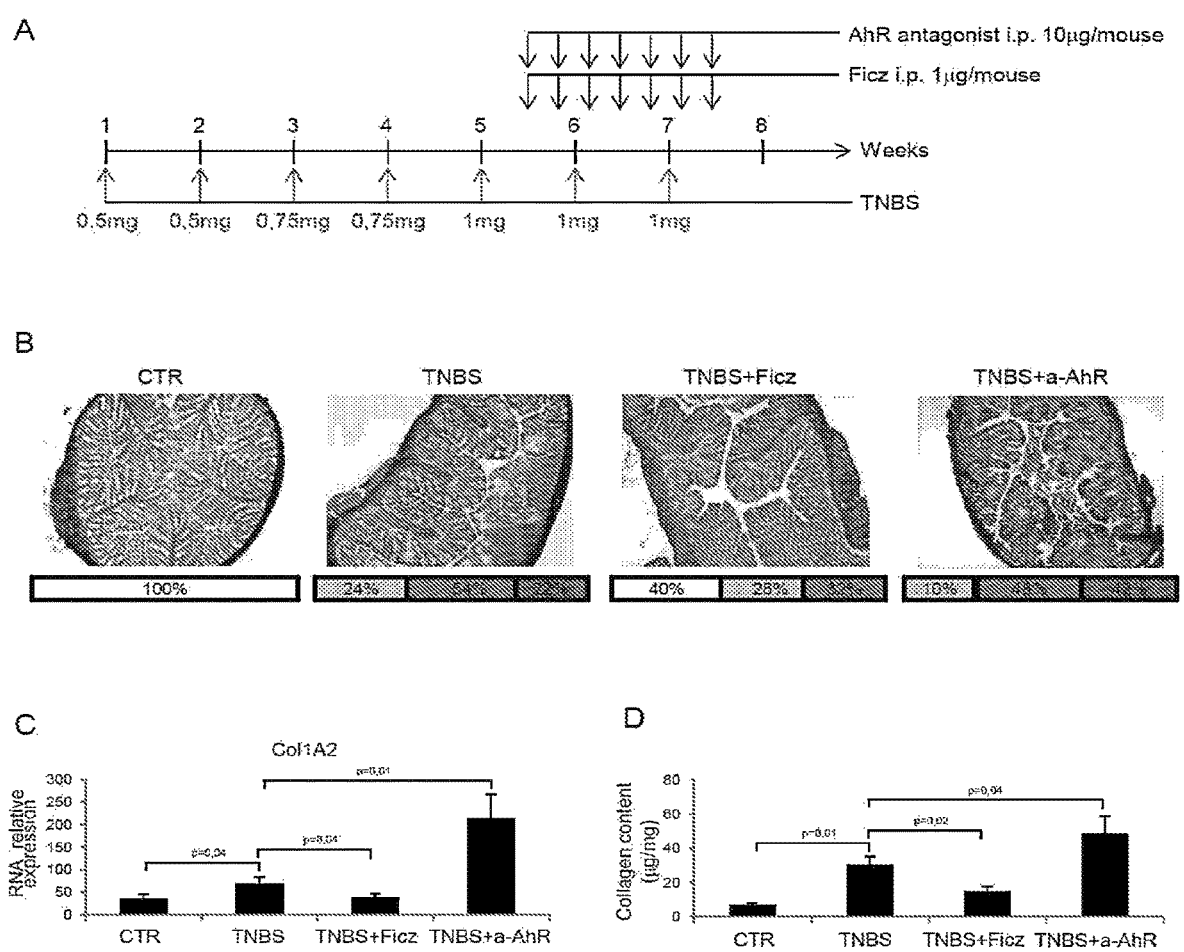
FIG. 30A shows a schematic view of TNBS-induced intestinal fibrosis model. Balb/c mice were given weekly TNBS treatments and Ficz or CH223191 (a-AhR) were administered starting after the fifth TNBS administration.
FIG. 30B shows representative colon cross-sections of control (CTR) mice and TNBS-treated mice receiving Ficz or CH223191 (a-AhR) stained with Masson's trichrome. Percentages of animals harboring mild, moderate, and severe fibrosis are also indicated.
FIG. 30C shows relative RNA expression data for Col1A2 in colonic samples taken from CTR mice and TNBS-treated mice injected with Ficz or CH223191 (a-AhR) analyzed by real-time PCR.
FIG. 30D shows total collagen content data (μg/mg) analyzed by colorimetric assay. Data indicate mean+/−SD of 3 separate experiments (n=12 mice total per group). Taken together, these data demonstrate that Ficz-treated mice are largely protected from TNBS-induced intestinal fibrosis.

To translate these data in vivo, we used an experimental model of intestinal fibrosis induced in Balb/c mice by repeated, rectal administration of low-doses of TNBS. To determine whether AhR activation interferes with collagen synthesis and fibrosis development, mice were given intraperitoneally either Ficz or CH223191 after the fifth week of TNBS administration (FIGS. 30A-30B). This time point was selected on the basis of previous studies showing that deposition of collagen begins at week 4 after the first TNBS administration. Extent and severity of inflammation and fibrosis were assessed in animals sacrificed on week 8. As expected, mice treated with repeated doses of TNBS exhibited minimal intestinal inflammation but marked thickening of the colon wall. Masson's trichrome staining of colonic sections and collagen RNA and protein analysis using whole colonic samples confirmed the increased collagen induction in TNBS-treated mice as compared to controls. Mice given Ficz exhibited a significant reduction of collagen expression while those receiving CH223191 produced more collagen as compared to TNBS-treated mice (FIGS. 30B-30C).

Discussion

This study investigated the role of AhR in the control of intestinal fibrosis. AhR was constitutively expressed in intestinal fibroblasts isolated from FS of CD patients as well as in intestinal fibroblasts of UC patients and normal controls. Although treatment of CD fibroblasts with Ficz did not modify the basal expression of collagen, inhibition of AhR with CH223191 led to increased collagen production, suggesting that constitutive AhR activation in these cells types is essential to keep collagen synthesis in check. Fibroblasts isolated from sites of FS in CD have enhanced capacity to respond to pro-fibrotic cytokines by producing collagen. Since studies in other systems have shown that AhR negatively regulates intracellular pathways activated by pro-fibrotic cytokines, it was next evaluated whether AhR activation is involved in TGF-β and TNF-α induced collagen production. CD fibroblasts displayed a different capacity to synthesize collagen when treated with Ficz or CH223191. In particular, Ficz dose-dependently reduced collagen RNA and protein expression while inhibition of AhR was followed by enhanced collagen production in response to TGF-β and TNF-α. Interestingly however, even at the greatest doses used in our system, Ficz did not completely abolish cytokine-induced collagen synthesis, raising the possibility that AhR does not control all the cytokine-driven intracellular pathways that lead to collagen production. Indeed, analysis of such signals revealed that Ficz abrogated activation of both p38 and ERK1/2 without affecting activation of Smad2/3 and NF-kB in fibroblasts stimulated with TGF-β or TNF-α, respectively. The fact that Ficz-mediated abrogation of p38 and ERK1/2 activation was accompanied by a 60% reduction of cytokine-driven collagen synthesis advocates a major role for MAP kinases in the control of collagen production in CD fibroblasts. The lack of effect of both Ficz and CH223191 on Smad2/3 and NF-kB activation in response to TGF-β or TNF-α is noteworthy, as these findings indicate that AhR activation does not induce a state of global unresponsiveness in intestinal fibroblasts, perhaps explaining why Ficz or CH223191 did not affect proliferation and survival of these cells.

The AhR-mediated negative regulation of collagen production was supported by in vivo studies in mice showing that Ficz was effective for minimizing fibrosis associated with chronic long-term inflammation. In contrast, mice receiving CH223191 exhibited a more intense collagen deposition as compared to control mice. In these studies, treatment with both Ficz and CH223191 started at a time point (week 5) that is characterized by pathological accumulation of collagen in the colon of TNBS-treated mice. Therefore, it is unlikely that the AhR-mediated inhibition of collagen production is secondary to suppression of the ongoing colitis.

In conclusion, these results show that AhR activation negatively controls collagen synthesis in the gut. These novel findings suggest that AhR-related compounds could help prevent and/or revert FS in patients with CD.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A compound represented by:

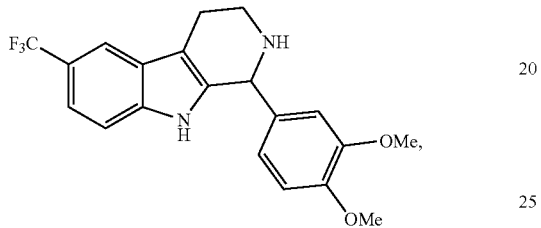

or a pharmaceutically acceptable salt thereof.

2. A pharmaceutical composition comprising a compound according to claim 1, or a pharmaceutically acceptable salt thereof; and a pharmaceutically acceptable carrier.

3. A method of treating or reducing fibrostenosis or intestinal fibrosis in a subject, the method comprising administering to a subject in need thereof a therapeutically effective amount of a compound according to claim 1, or a pharmaceutically acceptable salt thereof.

* * * * *